United States Patent
Stanton, IV et al.

(10) Patent No.: US 10,669,519 B2
(45) Date of Patent: Jun. 2, 2020

(54) CUSTOMIZABLE METHODS AND SYSTEMS OF GROWING AND HARVESTING CELLS IN A HOLLOW FIBER BIOREACTOR SYSTEM

(71) Applicant: Terumo BCT, Inc., Lakewood, CO (US)

(72) Inventors: Edward Allan Stanton, IV, Lakewood, CO (US); Glen Delbert Antwiler, Lakewood, CO (US); Patrick J. Howley, Highlands Ranch, CO (US); Michael E. Kinzie, Lafayette, CO (US); Jon A. Dodd, Littleton, CO (US); Casey V. Medina, Westminster, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 15/610,224

(22) Filed: May 31, 2017

(65) Prior Publication Data
US 2017/0267966 A1 Sep. 21, 2017

Related U.S. Application Data

(62) Division of application No. 13/269,351, filed on Oct. 7, 2011, now Pat. No. 9,677,042.
(Continued)

(51) Int. Cl.
*G06F 8/38* (2018.01)
*C12M 1/34* (2006.01)
(Continued)

(52) U.S. Cl.
CPC ............ *C12M 41/44* (2013.01); *C12M 23/42* (2013.01); *C12M 23/44* (2013.01); *C12M 25/10* (2013.01);
(Continued)

(58) Field of Classification Search
CPC . G06F 8/38; G06F 8/34; C12M 23/42; C12M 25/10; C12M 25/12; C12M 41/44; C12M 41/48; C12M 29/20; C12M 29/16
See application file for complete search history.

(56) References Cited

U.S. PATENT DOCUMENTS 3,821,087 A 6/1974 Knazek et al.
3,883,393 A 5/1975 Knazek et al.
(Continued)

FOREIGN PATENT DOCUMENTS

EP 0220650 A2 5/1987
EP 0201086 EP 1/1992
(Continued)

OTHER PUBLICATIONS

Biovest International, "AutovaxIDTM: advanced hollow fibre bioreactors with automated lactate control yield higher tensity monoclonal antibody production", VWRbioMarke, No. 21, Sep. 2008, pp. 10-11.
(Continued)

*Primary Examiner* — Shogo Sasaki
(74) *Attorney, Agent, or Firm* — Terumo BCT, Inc. IP Law Department

(57) ABSTRACT

Embodiments described herein generally relate to methods and systems for customizing protocols for use with a cell expansion system. Through a user interface, a user may create a custom task for loading, growing and/or harvesting cells. A custom task may comprise one or more steps, in which a user may add or omit steps, as desired. Data may be entered for settings associated with a custom task, in which embodiments provide for such data to be entered each time the custom task is performed. In another embodiment, the settings for a custom task may be configured, in which such settings may be stored and retrieved upon selection of the custom task. Customization and configuration of a custom
(Continued)

task may occur using a diagram view of the cell expansion system, in which process settings are associated with graphical user interface elements.

14 Claims, 45 Drawing Sheets

Related U.S. Application Data

(60) Provisional application No. 61/391,152, filed on Oct. 8, 2010, provisional application No. 61/434,726, filed on Jan. 20, 2011.

(51) Int. Cl.
    *C12M 3/00* (2006.01)
    *C12M 1/12* (2006.01)
    *C12M 1/00* (2006.01)
    *C12M 1/36* (2006.01)
    *G06F 8/34* (2018.01)

(52) U.S. Cl.
    CPC ............ *C12M 25/12* (2013.01); *C12M 29/16* (2013.01); *C12M 29/20* (2013.01); *C12M 41/48* (2013.01); *G06F 8/38* (2013.01)

(56) References Cited

U.S. PATENT DOCUMENTS

| | | |
|---|---|---|
| 3,896,061 A | 7/1975 | Tanzawa et al. |
| 3,997,396 A | 12/1976 | Delente |
| 4,184,922 A | 1/1980 | Knazek et al. |
| 4,200,689 A | 4/1980 | Knazek et al. |
| 4,220,725 A | 9/1980 | Knazek et al. |
| 4,391,912 A | 7/1983 | Yoshida et al. |
| 4,439,322 A | 3/1984 | Sonoda et al. |
| 4,440,853 A | 4/1984 | Michaels et al. |
| 4,618,586 A | 10/1986 | Walker |
| 4,629,686 A | 12/1986 | Gruenberg |
| 4,647,539 A | 3/1987 | Bach |
| 4,650,766 A | 3/1987 | Harm et al. |
| 4,657,866 A | 4/1987 | Kumar |
| 4,722,902 A | 2/1988 | Harm et al. |
| 4,789,658 A | 12/1988 | Yoshimoto et al. |
| 4,804,628 A | 2/1989 | Cracauer et al. |
| 4,885,087 A | 12/1989 | Kopf |
| 4,889,812 A | 12/1989 | Guinn et al. |
| 4,894,342 A | 1/1990 | Guinn et al. |
| 4,910,139 A | 3/1990 | Chang et al. |
| 4,918,019 A | 4/1990 | Guinn |
| 4,973,558 A | 11/1990 | Wilson et al. |
| 4,999,298 A | 3/1991 | Wolfe et al. |
| 5,079,168 A | 1/1992 | Amiot |
| 5,081,035 A | 1/1992 | Halberstadt |
| 5,126,238 A | 6/1992 | Gebhard et al. |
| 5,156,844 A | 10/1992 | Aebischer et al. |
| 5,162,225 A | 11/1992 | Sager et al. |
| 5,192,553 A | 3/1993 | Boyse et al. |
| 5,202,254 A | 4/1993 | Amiot et al. |
| 5,252,216 A | 10/1993 | Folena-Wasserman et al. |
| 5,330,915 A | 7/1994 | Wilson et al. |
| 5,397,706 A | 3/1995 | Correa et al. |
| 5,399,493 A | 3/1995 | Emerson et al. |
| 5,416,022 A | 5/1995 | Amiot |
| 5,433,909 A | 7/1995 | Martakos et al. |
| 5,437,994 A | 8/1995 | Emerson et al. |
| 5,453,357 A | 9/1995 | Hogan |
| 5,459,069 A | 10/1995 | Palsson et al. |
| 5,460,964 A | 10/1995 | McGlave et al. |
| 5,486,389 A | 1/1996 | Gerber |
| 5,510,257 A | 4/1996 | Sirkar et al. |
| 5,541,105 A | 7/1996 | Melink et al. |
| 5,564,183 A | 10/1996 | Satou et al. |
| 5,581,687 A | 12/1996 | Lyle et al. |
| 5,605,822 A | 2/1997 | Emerson et al. |
| 5,622,857 A | 4/1997 | Goffe |
| 5,627,070 A | 5/1997 | Gruenberg |
| 5,631,006 A | 5/1997 | Melink et al. |
| 5,635,386 A | 6/1997 | Palsson et al. |
| 5,635,387 A | 6/1997 | Fei et al. |
| 5,646,043 A | 7/1997 | Emerson et al. |
| 5,653,887 A | 8/1997 | Wahl et al. |
| 5,656,421 A | 8/1997 | Gebhard et al. |
| 5,656,479 A | 8/1997 | Petitte et al. |
| 5,670,147 A | 9/1997 | Emerson et al. |
| 5,670,351 A | 9/1997 | Emerson et al. |
| 5,670,372 A | 9/1997 | Hogan |
| 5,677,136 A | 10/1997 | Simmons et al. |
| 5,677,355 A | 10/1997 | Shalaby et al. |
| 5,688,687 A | 11/1997 | Palsson et al. |
| 5,712,154 A | 1/1998 | Mullon et al. |
| 5,716,827 A | 2/1998 | Tsukamoto et al. |
| 5,736,396 A | 4/1998 | Bruder et al. |
| 5,750,397 A | 5/1998 | Tsukamoto et al. |
| 5,759,793 A | 6/1998 | Schwartz et al. |
| 5,763,194 A | 6/1998 | Slowiaczek et al. |
| 5,763,261 A | 6/1998 | Gruenberg |
| 5,763,266 A | 6/1998 | Palsson et al. |
| 5,766,948 A | 6/1998 | Gage et al. |
| 5,766,951 A | 6/1998 | Brown |
| 5,811,094 A | 9/1998 | Caplan et al. |
| 5,827,735 A | 10/1998 | Young et al. |
| 5,827,740 A | 10/1998 | Pittenger |
| 5,837,539 A | 11/1998 | Caplan et al. |
| 5,837,670 A | 11/1998 | Hartshorn |
| 5,843,780 A | 12/1998 | Thomson |
| 5,849,553 A | 12/1998 | Anderson et al. |
| 5,851,832 A | 12/1998 | Weiss et al. |
| 5,874,301 A | 2/1999 | Keller et al. |
| 5,882,918 A | 3/1999 | Goffe |
| 5,888,807 A | 3/1999 | Palsson et al. |
| 5,898,040 A | 4/1999 | Shalaby et al. |
| 5,908,782 A | 6/1999 | Marshak et al. |
| 5,914,268 A | 6/1999 | Keller et al. |
| 5,958,763 A | 9/1999 | Goffe |
| 5,968,829 A | 10/1999 | Carpenter |
| 5,981,211 A | 11/1999 | Hu et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,015,554 A | 1/2000 | Galy |
| 6,029,101 A | 2/2000 | Yoshida et al. |
| 6,037,174 A | 3/2000 | Smith et al. |
| 6,040,180 A | 3/2000 | Johe |
| 6,048,721 A | 4/2000 | Armstrong et al. |
| 6,077,708 A | 6/2000 | Collins et al. |
| 6,080,581 A | 6/2000 | Anderson et al. |
| 6,096,532 A | 8/2000 | Armstrong et al. |
| 6,110,739 A | 8/2000 | Keller et al. |
| 6,190,910 B1 | 2/2001 | Kusakabe et al. |
| 6,197,575 B1 | 3/2001 | Griffith et al. |
| 6,200,806 B1 | 3/2001 | Thomson |
| 6,224,860 B1 | 5/2001 | Brown |
| 6,228,635 B1 | 5/2001 | Armstrong et al. |
| 6,238,908 B1 | 5/2001 | Armstrong et al. |
| 6,306,169 B1 | 10/2001 | Lee et al. |
| 6,326,198 B1 | 12/2001 | Emerson et al. |
| 6,372,210 B2 | 4/2002 | Brown |
| 6,432,711 B1 | 8/2002 | Dinsmore et al. |
| 6,436,701 B1 | 8/2002 | Evans et al. |
| 6,500,668 B2 | 12/2002 | Samarut et al. |
| 6,530,956 B1 | 3/2003 | Mansmann |
| 6,566,126 B2 | 5/2003 | Cadwell |
| 6,582,955 B2 | 6/2003 | Martinez et al. |
| 6,593,123 B1 | 7/2003 | Wright et al. |
| 6,616,912 B2 | 9/2003 | Eddleman et al. |
| 6,617,159 B1 | 9/2003 | Cancedda et al. |
| 6,617,161 B2 | 9/2003 | Luyten et al. |
| 6,629,003 B1* | 9/2003 | Frizzell ............ G05B 19/41865 700/17 |
| 6,642,019 B1 | 11/2003 | Anderson et al. |
| 6,667,034 B2 | 12/2003 | Palsson et al. |

(56) References Cited

U.S. PATENT DOCUMENTS

| | | |
|---|---|---|
| 6,680,166 B1 | 1/2004 | Mullon et al. |
| 6,689,324 B2 * | 2/2004 | Inoue ............... B01J 19/0046 422/105 |
| 6,690,981 B1 * | 2/2004 | Kawachi ............... G05B 15/02 700/83 |
| 6,703,279 B2 | 3/2004 | Lee |
| 6,737,072 B1 | 3/2004 | Angele et al. |
| 6,835,566 B2 | 12/2004 | Smith et al. |
| 6,844,187 B1 | 1/2005 | Weschler et al. |
| 6,875,607 B1 | 4/2005 | Reubinoff et al. |
| 6,911,201 B1 | 6/2005 | Merchav et al. |
| 6,933,144 B2 | 8/2005 | Cadwell |
| 6,943,008 B1 | 9/2005 | Ma |
| 6,944,522 B2 * | 9/2005 | Karmiy ............... G05B 19/0426 210/650 |
| 6,969,308 B2 | 11/2005 | Doi et al. |
| 6,979,308 B1 | 12/2005 | McDonald et al. |
| 7,015,037 B1 | 3/2006 | Furcht et al. |
| 7,029,913 B2 | 4/2006 | Thomson |
| 7,033,823 B2 | 4/2006 | Chang |
| 7,037,721 B1 | 5/2006 | Wille, Jr. |
| 7,041,493 B2 | 5/2006 | Rao |
| 7,109,032 B2 | 9/2006 | Cancedda et al. |
| 7,112,437 B2 | 9/2006 | Pera |
| 7,112,441 B2 | 9/2006 | Uemura et al. |
| 7,145,057 B2 | 12/2006 | Van de Lavoir et al. |
| 7,153,684 B1 | 12/2006 | Hogan |
| 7,169,610 B2 | 1/2007 | Brown |
| 7,172,696 B1 | 2/2007 | Martinez et al. |
| 7,270,996 B2 | 9/2007 | Cannon et al. |
| 7,294,508 B2 | 11/2007 | Parikh et al. |
| 7,531,351 B2 | 5/2009 | Marx et al. |
| 7,534,609 B2 | 5/2009 | Merchav et al. |
| 7,678,573 B2 | 3/2010 | Merchav et al. |
| 7,682,822 B2 | 3/2010 | Noll et al. |
| 7,718,430 B2 | 5/2010 | Antwiler |
| 7,838,289 B2 | 11/2010 | Furcht et al. |
| 8,309,347 B2 | 11/2012 | Antwiler |
| 8,321,145 B2 | 11/2012 | Antwiler |
| 8,383,397 B2 | 2/2013 | Wojciechowski et al. |
| 8,524,496 B2 | 9/2013 | Meiron et al. |
| 8,529,888 B2 | 9/2013 | Meiron et al. |
| 8,540,499 B2 | 9/2013 | Page et al. |
| 8,785,181 B2 | 7/2014 | Antwiler |
| 9,260,698 B2 | 2/2016 | Antwiler |
| 9,441,195 B2 | 9/2016 | Wojciechowski et al. |
| 9,534,198 B2 | 1/2017 | Page et al. |
| 9,677,042 B2 | 6/2017 | Stanton, IV et al. |
| 9,725,689 B2 | 8/2017 | Stanton, IV et al. |
| 2001/0044413 A1 | 11/2001 | Pierce et al. |
| 2002/0164794 A1 | 11/2002 | Wernet |
| 2003/0037836 A1 | 2/2003 | Blatt et al. |
| 2003/0059414 A1 | 3/2003 | Ho et al. |
| 2003/0069650 A1 | 4/2003 | Karmiy et al. |
| 2003/0181269 A1 | 9/2003 | Griffin |
| 2003/0224510 A1 | 12/2003 | Yamaguchi et al. |
| 2004/0032430 A1 | 2/2004 | Yung et al. |
| 2005/0003530 A1 | 1/2005 | Gerlach |
| 2005/0013804 A1 | 1/2005 | Kato et al. |
| 2005/0028218 A1 | 2/2005 | Gerlach |
| 2005/0153442 A1 | 7/2005 | Katz et al. |
| 2006/0147246 A1 | 7/2006 | Richards |
| 2006/0205071 A1 | 9/2006 | Hasson et al. |
| 2006/0233834 A1 | 10/2006 | Guehenneux et al. |
| 2007/0122904 A1 | 5/2007 | Nordon |
| 2007/0160583 A1 | 7/2007 | Lange et al. |
| 2007/0192715 A1 | 8/2007 | Kataria et al. |
| 2007/0269486 A1 | 11/2007 | Parker et al. |
| 2007/0298497 A1 | 12/2007 | Antwiler |
| 2008/0206733 A1 | 8/2008 | Tanaka et al. |
| 2008/0213894 A1 | 9/2008 | Antwiler |
| 2008/0220522 A1 | 9/2008 | Antwiler |
| 2008/0220523 A1 | 9/2008 | Antwiler |
| 2008/0227190 A1 | 9/2008 | Antwiler |
| 2008/0248572 A1 | 10/2008 | Antwiler |
| 2008/0254533 A1 | 10/2008 | Antwiler |
| 2008/0268538 A1 | 10/2008 | Nordon et al. |
| 2009/0004738 A1 | 1/2009 | Merchav et al. |
| 2009/0104653 A1 | 4/2009 | Paldus et al. |
| 2009/0191631 A1 | 7/2009 | Bornemann |
| 2009/0196901 A1 | 8/2009 | Guilak et al. |
| 2009/0215022 A1 | 8/2009 | Page et al. |
| 2009/0269841 A1 | 10/2009 | Wojciechowski et al. |
| 2010/0042260 A1 | 2/2010 | Antwiler |
| 2010/0090971 A1 | 4/2010 | Choi et al. |
| 2010/0144037 A1 | 6/2010 | Antwiler |
| 2010/0209403 A1 | 8/2010 | Meiron et al. |
| 2010/0233130 A1 | 9/2010 | Meretzki |
| 2010/0267134 A1 | 10/2010 | Pera et al. |
| 2011/0060463 A1 | 3/2011 | Selker et al. |
| 2011/0129447 A1 | 6/2011 | Meretzki et al. |
| 2011/0129486 A1 | 6/2011 | Meiron |
| 2011/0171182 A1 | 7/2011 | Abelman |
| 2011/0212493 A1 | 9/2011 | Hirschel et al. |
| 2011/0256108 A1 | 10/2011 | Meiron et al. |
| 2011/0256160 A1 | 10/2011 | Meiron et al. |
| 2011/0293583 A1 | 12/2011 | Aberman |
| 2012/0086657 A1 | 4/2012 | Stanton, IV et al. |
| 2012/0089930 A1 | 4/2012 | Stanton, IV et al. |
| 2012/0122220 A1 | 5/2012 | Merchav et al. |
| 2012/0308531 A1 | 12/2012 | Pinxteren et al. |
| 2013/0004465 A1 | 1/2013 | Aberman |
| 2013/0039892 A1 | 2/2013 | Aberman |
| 2013/0058907 A1 | 3/2013 | Wojciechowski et al. |
| 2013/0259843 A1 | 10/2013 | Duda et al. |
| 2013/0323213 A1 | 12/2013 | Meiron et al. |
| 2013/0337558 A1 | 12/2013 | Meiron et al. |
| 2014/0017209 A1 | 1/2014 | Aberman et al. |
| 2014/0030805 A1 | 1/2014 | Kasuto et al. |
| 2014/0242039 A1 | 8/2014 | Meiron et al. |
| 2015/0024492 A1 | 1/2015 | Antwiler |
| 2015/0111252 A1 | 4/2015 | Hirschel et al. |
| 2015/0125138 A1 | 5/2015 | Kamieli et al. |
| 2015/0175950 A1 | 6/2015 | Hirschel et al. |
| 2015/0225685 A1 | 8/2015 | Hirschel et al. |
| 2015/0259749 A1 | 9/2015 | Santos et al. |
| 2016/0362650 A1 | 12/2016 | Wojciechowski et al. |
| 2016/0362652 A1 | 12/2016 | Page et al. |
| 2017/0107488 A1 | 4/2017 | Petcavich |
| 2017/0335270 A1 | 11/2017 | Stanton, IV et al. |

FOREIGN PATENT DOCUMENTS

| | | |
|---|---|---|
| EP | 0224734 B1 | 3/1992 |
| EP | 1367119 A2 | 12/2003 |
| EP | 1147176 B1 | 12/2009 |
| EP | 2208782 A2 | 7/2010 |
| EP | 2027247 B1 | 1/2011 |
| EP | 2311938 A1 | 4/2011 |
| EP | 2366775 A1 | 9/2011 |
| EP | 2200622 B1 | 8/2012 |
| EP | 2548951 A1 | 1/2013 |
| EP | 2591789 A2 | 5/2013 |
| EP | 2626417 A1 | 8/2013 |
| EP | 2641606 A1 | 9/2013 |
| JP | H02245177 A | 9/1990 |
| JP | H03047074 A | 2/1991 |
| JP | 2003510068 A | 3/2003 |
| JP | 2005278564 A | 10/2005 |
| JP | 2005333945 A | 12/2005 |
| JP | 2007000038 A | 1/2007 |
| WO | 86/02379 A1 | 4/1986 |
| WO | 88/01643 A1 | 3/1988 |
| WO | 98/53046 A2 | 11/1988 |
| WO | 90/02171 A1 | 3/1990 |
| WO | 91/07485 A1 | 5/1991 |
| WO | 91/10425 A1 | 7/1991 |
| WO | 91/18972 A1 | 12/1991 |
| WO | 92/10564 A1 | 6/1992 |
| WO | 95/04813 A1 | 2/1995 |
| WO | 95/13088 A1 | 5/1995 |
| WO | 95/21911 A1 | 8/1995 |
| WO | 9/27041 A1 | 10/1995 |
| WO | 96/39487 A1 | 12/1996 |

(56) References Cited

FOREIGN PATENT DOCUMENTS

| | | | |
|---|---|---|---|
| WO | 97/16527 | A1 | 5/1997 |
| WO | 98/50526 | A1 | 11/1998 |
| WO | 99/01159 | A1 | 1/1999 |
| WO | 00/75275 | A1 | 12/2000 |
| WO | 01/23520 | A1 | 4/2001 |
| WO | 02/28996 | A1 | 4/2002 |
| WO | 03/024587 | A1 | 3/2003 |
| WO | 03/070922 | A1 | 8/2003 |
| WO | 03/105663 | A2 | 12/2003 |
| WO | 2004/090112 | A2 | 10/2004 |
| WO | 2005/007799 | A2 | 1/2005 |
| WO | 2005/087915 | A2 | 9/2005 |
| WO | 2006/019357 | A1 | 2/2006 |
| WO | 2006/026835 | A1 | 3/2006 |
| WO | 07/012144 | A1 | 2/2007 |
| WO | 2007/136821 | A1 | 11/2007 |
| WO | 2007/139742 | A1 | 12/2007 |
| WO | 2007/139746 | A1 | 12/2007 |
| WO | 2007/139747 | A1 | 12/2007 |
| WO | 2007/139748 | A1 | 12/2007 |
| WO | 2009/144720 | A1 | 12/2009 |
| WO | 2010/026573 | A1 | 3/2010 |
| WO | 2010/026574 | A2 | 3/2010 |
| WO | 2010/026575 | A2 | 3/2010 |
| WO | 10/034468 | A1 | 4/2010 |
| WO | 10/149597 | A2 | 12/2010 |
| WO | 2011/132087 | A1 | 10/2011 |
| WO | 2011/147967 | A1 | 12/2011 |
| WO | 2012/127320 | A1 | 9/2012 |
| WO | 2012/140519 | A2 | 10/2012 |
| WO | 2012/171026 | A2 | 12/2012 |
| WO | 2012/171030 | A2 | 12/2012 |
| WO | 2014/037862 | A1 | 3/2014 |
| WO | 2014/037863 | A1 | 3/2014 |
| WO | 2014/068508 | A2 | 5/2014 |
| WO | 2014/128634 | A1 | 8/2014 |
| WO | 2014/141111 | A1 | 9/2014 |
| WO | 2015/004609 | A2 | 1/2015 |
| WO | 2017/066663 | A1 | 4/2017 |

OTHER PUBLICATIONS

Chang et al., "Membrane Bioreactors: Present and Prospects", Advances in Biochemical Engineering, 1991, vol. 44, pp. 27-64.
Chang, Ho Nam, "Membrane Bioreactors: Engineering Aspects", Biotech. Adv., 1987, vol. 5, pp. 129-145.
Clausen et al., "Lactate as an Indicator of Terminating Time in Insect Cell Culture Baculovirus Expression Vector Systems", Biotechnology Techniques, vol. 10, No. 10, Oct. 1996, pp. 721-726.
Eddington, Stephen M., "New Horizons for Stem-Cell Bioreactors", Biotechnology, Oct. 1992, vol. 10, pp. 1099-1106.
Gastens et al., "Good Manufacturing Practice-Compliant Expansion of Marrow-Derived Stem and Progenitor Cells for Cell Therapy", Cell Transplantation, 2007, vol. 16, pp. 685-696.
Gerlach, J.C. et al., "Comparison of hollow fibre membranes for hepatocyte immobilization in bioreactors," The International Journal of Artificial Organs, 1996, Vol. 19 No. 10, pp. 610-616.
Gloeckner et al., "New Miniaturized Hollow-Fiber Bioreacter for in Vivo Like Cell Culture, Cell Expansion, and Production of Cell-Derived Products", Biotechnol. Prog., Aug. 21, 2001, vol. 17, No. 5, pp. 828-831.
Gramer et al., "Screening Tool for Hollow-Fiber Bioreactor Process Development", Biotechnol. Prog., 1998, vol. 14, pp. 203-209.
Grayson et al., "Effects of Hypoxia on Human Mesenchymal Stem Cell Expansion and Plasticity in 3D Constructs", J. Cellular Physiology, 2006, 207:331-339.
Hirschel et al., "An Automated Hollow Fiber System for the Large Scale Manufacture of Mammalian Cell Secreted Product", Large Scale Cell Culture Technology, ed. Bjorn K. Lydersen, Hanser Publishers, 1987, pp. 113-144.

Lloyd, J.R. et al., "Hollow-Fibre bioreactors compared to batch and chemostat culture for the production of a recombinant toxoid by a marine Vibrio," Appl. Microbiol Biotechnol, Aug. 1997, vol. 48, pp. 155-161.
Nielsen, Lars Keld, "Bioreactors for Hematopoietic Cell Culture", Annu. Rev. Biomed. Eng., 1999, vol. 1, pp. 129-152.
Neumann, Detlef et al., "Bioreaktorsteurung mit grafischer Bedienoberflache," ATP Automatisierungstechnische Praxis, Mar. 1995, pp. 16-23, vol. 37, No. 3, Munchen, DE. (English language translation included).
Ozturk et al., "Real-Time Monitoring and Control of Glucose and Lactate Concentrations in a Mammalian Cell Perfusion Reactor", Biotechnology and Bioengineering, vol. 53, No. 4, Feb. 20, 1997, pp. 372-378.
PCT/US2011/055451, "International Search Report and Written Opinion," dated Jun. 21, 2012.
PCT/US2011/055453, "International Search Report and Written Opinion," dated Jun. 21, 2012.
Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.
Sauer, I. et al., "Extracorporeal liver support based on primary human liver cells and albumin dialysis—treatment of patient with primary graft non function," Journal of Hepatology, Oct. 2003, vol. 39 No. 4, pp. 649-653.
Wang et al., "Influence of Oxygen on the Proliferation and Metabolism of Adipose Derived Adult Stem Cells", J. Cellular Physiology, 2005, 204:184-161.
Zhao et al., "Effects of Oxygen Transport on 3-D human Mesenchymal Stem Cell Metabolic Activity in Perfusion and Static Cultures: Experiments and Mathematical Model", Biotechnol. Prog, 2005, 27, 1269-1280.
Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 182-493.
Notice of Allowance and Fee(s) Due, U.S. Appl. No. 13/269,323, dated Apr. 7, 2016.
Notice of Allowance and Fee(s) Due, U.S. Appl. No. 13/269,323, dated Dec. 9, 2016.
Office Action, U.S. Appl. No. 13/269,323, dated Aug. 20, 2015.
Official Communication, European Patent Application No. 11773364.2, dated Sep. 21, 2016.
Official Communication, European Patent Application No. 11773365.9, dated Sep. 21, 2016.
Official Communication, European Patent Application No. 11773364.2, dated Jul. 28, 2017.
Official Communication, European Patent Application No. 11773365.9, dated Jul. 28, 2017.
Office Action, U.S. Appl. No. 13/269,351, dated Sep. 9, 2015.
Office Action, U.S. Appl. No. 13/269,351, dated Feb. 11, 2016.
Notice of Allowance and Fee(s) Due, U.S. Appl. No. 13/269,351, dated Oct. 5, 2016.
Notice of Allowance and Fee(s) Due, U.S. Appl. No. 13/269,351, dated Feb. 13, 2017.
Notice of Allowance and Fee(s) Due, U.S. Appl. No. 15/670,931, dated Nov. 8, 2018.
Communication under Rule 71(3) EPC, European Patent Application No. 11773364.2, dated Aug. 17, 2018.
Communication under Rule 71(3) EPC, European Patent Application No. 11773364.2, dated Jan. 2, 2019.
Communication under Rule 71(3) EPC, European Patent Application No. 11773365.9, dated Aug. 28, 2018.
Communication under Rule 71(3) EPC, European Patent Application No. 11773365.9, dated Jan. 18, 2019.
Communication under Rule 71(3) EPC, European Patent Application No. 11773364.2, dated Jun. 4, 2019
Corrected Notice of Allowability, U.S. Appl. No. 15/670,931, dated Jun. 26, 2019.
Notice of Allowance and Fee(s) Due, U.S. Appl. No. 15/670,931, dated Apr. 17, 2019.

(56) References Cited

OTHER PUBLICATIONS

Campagnoli Cesare, et al.: "Identification of mesenchymal stem/progenitor cells in human first-trimester fetal blood, liver, and bone marrow," Blood, American Society of Hematology, US, vol. 98, No, 8, Oct. 15, 2001 (Oct. 15, 2001), pp. 2396-2402.
Colter, David C., et al., "Rapid expansion of recycling stern cells in cultures of plastic-adherent cells from human bone marrow," PNAS, Mar. 28, 2000, vol, 97, No. 7, pp. 3213-3218.
Deans, Robert J., et al., "Mesenchymal stem cells: Biology and potential clinical uses," Experimental Hematology 28 (2000), pp. 875-884.
De Kreuk, Arne M., et al., "A Single-Step Colony-Forming Unit Assay for Unseparated Mobilized Peripheral Blood, Cord Blood, and Bone Marrow," Journal of Hematotherapy & Stem Cell Research, Mary Ann Liebert, Inc., 2001, vol. 10, pp. 795-806.
Deppisch, Reinhold, et al., "Microdomain structure of polymeric surfaces— Potential for improving blood treatment procedures," Nephrol Dial Transplant, 1998, vol. 13, pp. 1354-1359.
Humes, HD, et al., "The future of hemodialysis membranes," Kidney International, 2006, vol. 69, pp. 1115-1119.
Javazon, Elisabeth H., et al., "Rat Marrow Stromal Cells are More Sensitive to Plating Density and Expand More Rapidly from Single-Cell-Derived Colonies than Human Marrow Stromal Cells," Stem Cells, 2001, vol. 19, pp. 219-225.
Lin, Wen-Ching, et al., "Blood compatibility of thermoplastic polyurethane membrane immobilized with water soluble chitosan/dextran sulfate," Colloids and Surfaces B: Biointerfaces, 2005, vol. 44, pp. 82-92.
Martin, Ivan, et al., "Selective differentiation of mammalian bone marrow stromal cells cultured on three-dimensional polymer foams," Engineering Skeletal Tissues from Bone Marrow, John Wiley & Sons, Inc., 2001, pp. 229-235.
Sekiya, Ichiro, et al., "Expansion of Human Adult Stem Cells from Bone Marrow Stroma: Conditions that Maximize the Yields of Early Progenitors and Evaluate Their Quality," Stem Cells, 2002, vol. 20, pp. 530-541.
Sotiropoulou, Panagiota A., et al., "Characterization of the Optimal Culture Conditions for Clinical Scale Production of Human Mesenchymal Stem Cells," Stem Cells, 2006, vol. 24, pp. 462-471.
Tsai, Ming-Song, et al., "Isolation of human multipotent mesenchymal stem cells from second-trimester amniotic fluid using a novel two-stage culture protocol,"Human Reproduction, 2004, vol. 19, No. 6. pp. 1450-1456.
Antwiler, et al., "Bioreactor Design and Implementation," Methods in Bioengineering: Stem Cell Bioengineering, Parekkadan and Yarmush, eds., Artech House, Chapter 4, pp. 49-62 (2009).
Brambrink, et al., "Sequential Expression of Pluripotency Markers during Direct Reprogramming of Mouse Somatic Cells," Cell Stem Cell, 2:151-159 (2008).
Chua, et al., "Stable immobilization of rat hepatocyte spheroids on galactosylated nanofiber scaffold," Biomaterials, 26:2537-2547 (2004).
Communication under Rule 71(3) EPC, European Patent Application No. 11773364.2, Oct. 31, 2019.
Drobinskaya, et al., "Scalable Selection of Hepatocyte—and Hepatocyte Precursor-Like Cells from Culture of Differentiating Transgenically Modified Murine Embryonic Stem Cells," Stem Cells, 26:2245-2256 (2008).
Dvir-Ginzberg, et al., "Induced differentiation and maturation of newborn liver cells into functional hepatic tissue in macroporous alginate scaffolds," FASEB J., 22:1440-1449 (2008).
Guan, et al., "Pluripotency of spermatogonial stem cells from adult mouse testis," Nature, 440:1199-1203 (2006).
Hanna, et al., "Direct Reprogramming of Terminally Differentiated Mature B Lymphocytes to Pluripotency," Cell, 133:250-264 (2008).
Hoenich, et al., "A Microdomain-Structured Synthetic High-Flux Hollow-Fiber Membrane for Renal Replacement Therapy," ASAIO J., 46:70-75 (2000).
Jaenisch, et al., "Stem Cells, the Molecular Circuitry of Pluripotency and Nuclear Reprogramming," Cell, 132:567-582 (2008).
Jahagirdar, B. N., et al., "Novel therapies for chronic myelogenous leukemia," Experimental Hematology, 29:543-556 (2001).
Jiang, Y., et al., "Multipotent progenitor cells can be isolated from postnatal murine bone marrow, muscle, and brain," Experimental Hematology, 30896-904 (2002).
Jiang, Y., et al., "Pluripotency of mesenchymal stem cells derived from adult marrow," Nature, 418:41-49. (2002).
Kirouac, et al., "The Systematic Production of Cells for Cell Therapies," Cell Stem Cell, 3:369-381 (2008).
Matsumoto, et al., "Hepatic Differentiation of Mouse Embryonic Stem Cells in a Three-Dimensional Culture System Using Polyurethane Foam," Journal of Bioscience and Bioengineering, 105:350-354 (2008).
McNiece, et al., "Ex-vivo expansion of hematopoietic progenitor cells: preliminary results in breast cancer," Hematol cell Ther, 41:82-86 (1999).
McNiece, et al., "Increased expansion and differentiation of cord blood products using a two-step expansion culture," Experimental Hematology, 28:1181-1186 (2000).
Mesquita, Fernanda C., et al., "Laminin as a Potent Substrate for Large-Scale Expansion of Human Induced Pluripotent Stem Cells in a Closed Cell Expansion System," Hindawi, Stem Cells International, vol. 2019, Article ID 9704945, Jan. 22, 2019, pp. 1-9.
Miyazawa, et al., "Hepatocyte dynamics in a three-dimensional rotating Bioreactor," Journal of Gastroenterology and Hepatology, 22:1959-1964 (2007).
Ohashi, et al., "Engineering functional two—and three-dimensional liver systems in vivo using hepatic tissue sheets," Nature Medicine, 13:880-885 (2007).
Okita, et al., "Generation of germline-competent induced pluripotent stem cells," Nature, 448:313-318 (2007).
Reyes, M. and C. M. Verfaillie, "Characterization of Multipotent Adult Progenitor Cells, a Subpopulation of Mesenchymal Stem Cells" Ann NY Acad Sci, 938:231-235 (2001).
Sheu, Jonathan, et al., "Large-scale production of lentiviral vector in a closed system hollow fiber bioreactor," Nature, Molecular Therapy - Methods & Clinical Development, 2, Article number: 15020 (2015), doi:10.1038/mtm.2015.20, Jun. 17, 2015, <http://www.nature.com/articles/mtm201520>, pp. 1-18.
Takahashi, et al., "Induction of Pluripotent Stem Cells from Mouse Embryonic and Adult Fibroblast Cultures by Defined Factors," Cell, 126:663-676 (2006).
Takahashi, et al., "Induction of Pluripotent Stem Cells from Adult Human Fibroblasts by Defined Factors," Cell, 131:861-872 (2007).
Turner, at al., "Human Hepatoblast Phenotype Maintained by Hyaluronan Hydrogels," Journal of Biomedical Materials Research Part B: Applied Biomaterials, Wiley InterScience (www.interscience.wiley.com), 82B:156-168 (2006).
Verfaillie, C. M., "Adult stem cells: assessing the case for pluripotency," Trends Cell Biol 12:502-508 (2002).
Voss, Harald, "Bioreactors," Ullmann's Encyclopedia of Industrial Chemistry: Fifth ed., B. Elvers, S. Hawkins and G. Schulz Eds, VCH Publishers, 1992, vol. B4, pp. 381-433.
Wernig, et al., "Neurons derived from reprogrammed fibroblasts functionally integrate into the fetal brain and improve symptoms of rats with Parkinson's disease," PNAS, 105:5856-5861 (2008).
Wilmut, et al., "Viable offspring derived from fetal and adult mammalian cells," Nature, 385:810-813 (1997).
Yamanaka, S. "Strategies and New Developments in the Generation of Patient-Specific Pluripotent Stem Cells," Cell Stem Cell, 1:39-49 (2007).
Ying, et al., "Changing potency by spontaneous fusion," Nature, 416:545-548 (2002).
Zandstra, et al., "Expansion of Hematopoietic Progenitor Cell Populations in Stirred Suspension Bioreactors of Normal Human Bone Marrow Cells," Biotechnol, 12:909-914 (1994).

\* cited by examiner

Configure Confirmation: Task A

| Number of Steps: # | Step 1 | Step 2 | Step # |
|---|---|---|---|
| IC Inlet | Wash | Reagent | Wash |
| IC Inlet Rate (mL/min) | 100 | 50 | 50 |
| IC Inlet Rate (mL/min) | -17 | 300 | 300 |
| EC Inlet | Wash | None | None |
| EC Inlet Rate (mL/min) | 148 | 0.00 | 0.00 |
| EC Circulation Rate | -1.7 | 30 | 30 |
| Outlet | IC & EC Waste | EC Waste | EC Waste |
| Rocker | In Motion.... | In Motion.... | In Motion.... |
| Stop Condition | Exchange.... | Empty Bag | IC Volume.... |
| Estimated Fluid Needed (L) | Wash: 1.4 | Unknown | Wash: 0.1 |
| Omit or Include Step | Include | Include | Include |
| Other | ### | ### | ### |

Reset 1-05-2011 2:17 PM Idle

FIG. 11

Configure Confirmation: Custom Task 1

Number of Steps: #

| | Custom: Step 1 | Custom: Step 2 |
|---|---|---|
| IC Inlet | None | Reagent |
| IC Inlet Rate (mL/min) | 0 | 10 |
| IC Inlet Rate (mL/min) | 0 | 100 |
| EC Inlet | None | None |
| EC Inlet Rate (mL/min) | 0 | 0 |
| EC Circulation Rate | 0 | 30 |
| Outlet | EC Waste | EC Waste |
| Rocker | Stationary (0°) | Stationary (0°) |
| Stop Condition | Manual | IC Volume (10 mL) |
| Estimated Fluid Needed (L) | 0 | 0 |
| Other | ### | ### |

1-05-2011  2:17 PM  Idle

FIG. 12C

CUSTOMIZABLE METHODS AND SYSTEMS OF GROWING AND HARVESTING CELLS IN A HOLLOW FIBER BIOREACTOR SYSTEM

CROSS-REFERENCE TO RELATED APPLICATIONS

This application is a divisional application of, and claims priority to, U.S. patent application Ser. No. 13/269,351, entitled, "Customizable Methods and Systems of Growing and Harvesting Cells in a Hollow Fiber Bioreactor System," filed on Oct. 7, 2011, and issued as U.S. Pat. No. 9,677,042 on Jun. 13, 2017, which claims the benefit of U.S. Provisional Application Ser. No. 61/391,152, filed on Oct. 8, 2010, and entitled, "Methods of Growing and Harvesting Cells in a Hollow Fiber Bioreactor System" and of U.S. Provisional Application Ser. No. 61/434,726, filed on Jan. 20, 2011, and entitled, "Methods of Growing and Harvesting Cells in a Hollow Fiber Bioreactor System." The disclosures of the above-identified applications are hereby incorporated by reference in their entireties as if set forth herein in full for all that they teach and for all purposes.

FIELD

Embodiments of the present disclosure relate to cell growth in cell expansion systems.

BACKGROUND

The use of stem cells in a variety of medical treatments and therapies is receiving growing attention. Cell expansion systems can be used to grow stem cells, as well as other types of cells, such as bone marrow cells which may include stem cells. Stem cells which are expanded from donor cells can be used to repair or replace damaged or defective tissues and are considered for treating a wide range of diseases. Cell expansion systems (CESs) are used to expand cells and may be used to expand donor stem cells from bone marrow. Stem cells may be grown in hollow fiber bioreactors in a cell expansion system.

SUMMARY

Embodiments of the present disclosure generally relate to providing processor-implemented methods and systems for customizing protocols or tasks for use with a cell expansion system. Aspects of particular embodiments provide for a user interface (UI) and the use of graphical user interface (GUI) elements for creating a custom or user-defined protocol or task. In embodiments, steps may be added and/or omitted from a custom or user-defined task. Further embodiments provide for a custom or user-defined task to be configured. In embodiments, UI or GUI elements associated with settings for particular steps of a custom protocol or task used with the cell expansion system are rendered and displayed in diagram windows on a display device. Such UI or GUI elements may be selected to configure one or more settings. In embodiments, configured settings for a custom or user-defined task are stored and available for subsequent retrieval in performing actions related to the task.

The disclosure relates to a processor-implemented method for customizing a task for use with a cell expansion system. The method includes the steps of providing a cell expansion system; providing a bioreactor in the cell expansion system; providing a user interface for customizing a first custom task; receiving, through the user interface, a first selection of the first custom task, wherein the first custom task comprises a first step; providing a first setting for the first step in a table view; receiving a second selection to add a second step to the first custom task; providing a second setting for the second step in the table view; receiving a third selection to configure the first step of the first custom task; determining the first setting is configurable; and providing a diagram view of the cell expansion system, comprising: associating the diagram view with the first step, providing the first setting as a first graphical user interface element, and, in response to determining the first setting is configurable, enabling the first graphical user interface element for selection.

In at least one embodiment, the receiving a second selection to add a second step includes receiving a type of step to add, in which the type of step comprises one or more from the group consisting of: wash out lines, wash out lines through membrane, wash rapidly, harvest cells, add bolus, and custom. In at least one embodiment, receiving a first selection of a first custom task comprises: receiving a touch event on a display area of the user interface of the cell expansion system, determining a location of the touch event, mapping the location of the touch event to the first graphical user interface element, and determining the first graphical user interface element is associated with the first setting. In at least one embodiment, the touch event is received on a touch screen. In at least one embodiment, displaying the diagram view of the cell expansion system further comprises: depicting an intracapillary side of the bioreactor, and depicting an extracapillary side of the bioreactor.

In at least one embodiment, the method further includes determining whether the first setting is associated with a numeric value; and, if the first setting is associated with the numeric value, providing a data entry pad in the diagram view to receive the numeric value. In at least one embodiment, the method further includes if the first setting is not associated with the numeric value, determining if the first setting is associated with a menu of selection options; and, if the first setting is associated with the menu of selection options, providing the menu of selection options in the diagram view. In at least one embodiment, the method further comprises: receiving data for configuring the first setting, storing the data received for configuring the first setting, receiving an indication to execute the first custom task, and executing the first custom task with the data received for configuring the first setting.

In at least one embodiment, the first setting comprises one or more from the group consisting of: intracapillary inlet, intracapillary inlet rate, intracapillary circulation rate, extracapillary inlet, extracapillary inlet rate, extracapillary circulation rate, rocker, and stop condition. In at least one embodiment, the enabling of the first graphical user interface element for selection comprises: associating a first visual indicia with the first graphical user interface element, and, in response to determining the first setting is configurable, associating a second visual indicia with the first graphical user interface element.

The disclosure also relates to a cell expansion system. The cell expansion system comprises: a cell expansion system, including a bioreactor; a processor coupled to the cell expansion system; a display device, in communication with the processor, operable to display data; and a memory, in communication with and readable by the processor, and containing a series of instructions that, when executed by the processor, cause the processor to: receive a first selection of a task; provide a task type, wherein the task type comprises one or more from the group consisting of: a predetermined task type and a user-defined type; receive a second selection of a first user-defined task, wherein the first user-defined task comprises a first process; provide one or more settings for the first process in a table view; provide first data associated with at least a first setting of the one or more settings for the first process; receive an indication to add a second process to the first user-defined task; add the second process to the first user-defined task; receive an indication to modify the first process; display a diagram view associated with the first process, wherein the displaying comprises: associate the diagram view with the first process, provide the first setting as a first graphical user interface element, and, in response to determining the first setting may be modified, enabling the first graphical user interface element for selection; receive second data associated with the first setting; receive an indication to execute the first user-defined task; and execute the first user-defined task, comprising: execute the first user-defined task using the received second data associated with the first setting.

In at least one embodiment, the system further comprises after executing the first user-defined task, receive a second indication to execute the first user-defined task; and execute the first user-defined task using the first data associated with the at least a first setting. In at least one embodiment, the system comprises: in response to receiving the indication to add the second process, retrieve a type of process to add; provide a selection window of the type of process to add; and receive a third selection of the type of process to add. In at least one embodiment, the type of process to add comprises one or more from the group consisting of: wash out lines, wash out lines through membrane, wash rapidly, harvest cells, add bolus, and custom. In at least one embodiment, the system comprises: receive a fourth selection to configure the first user-defined task; display a diagram view comprising the first and second processes; receive a fifth selection to configure the second process; configure the second process; and store the configuration of the first user-defined task. In at least one embodiment, the system comprises after adding the second process to the first user-defined task, receive an indication to omit the second process from the first user-defined task; and omit the second process from the first user-defined task. In at least one embodiment, the displaying the diagram view comprises depicting an intracapillary side of the bioreactor of the cell expansion system; and depicting an extracapillary side of the bioreactor.

The disclosure further provides for a non-transitory processor-readable storage medium storing executable instructions which when executed by a processor perform a method of customizing a task used with a cell expansion system. The method includes the steps of receiving an indication to create a first custom task for use with the cell expansion system, wherein the cell expansion system comprises a bioreactor; receiving a first selection of the first custom task, wherein the first custom task comprises a first process; providing a setting associated with the first process; receiving a second selection to add a second process to the first custom task; in response to receiving the second selection, retrieving a type of process to add; providing a selection window comprising the types of processes to add, wherein the types of processes to add comprise one or more from the group consisting of: wash out lines, wash out lines through membrane, wash rapidly, harvest cells, add bolus, and custom; receiving a third selection of the type of process to add; adding the selected type of process as the second process to the first custom task; receiving data associated with a first setting of the first process; and executing the first custom task with the data received for the first setting of the first process.

In at least one embodiment, the method includes receiving an indication to configure the first custom task; receiving a numeric value for configuring a second setting of the first process; and storing the numeric value in association with the first custom task. In at least one embodiment, the method includes: based on the numeric value received for the second setting, determining to calculate a second numeric value for a third setting of the first process; automatically calculating the second numeric value; providing the second numeric value for the third setting of the first process; and storing the second numeric value in association with the first custom task.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items.

FIG. 11 illustrates an example UI for configuring settings of a protocol used with the cell expansion system in accordance with embodiments of the present disclosure.

FIG. 12C illustrates an example UI for configuring a custom or user-defined task with multiple steps for use with the cell expansion system in accordance with embodiments of the present disclosure.

DETAILED DESCRIPTION

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will understand other embodiments, including improvements, that are within the spirit and scope of the present disclosure.

Embodiments of the present disclosure are generally directed to sterile methods for loading, growing, and harvesting cells in a hollow fiber cell growth chamber of a closed cell expansion system. In further embodiments, sterile methods are provided for loading, growing, and harvesting adherent cells, in particular mesenchymal stem cells, in the hollow fiber cell growth chamber of the closed cell expansion system. A closed system means that the contents of the system are not directly exposed to the atmosphere.

Figure 1:
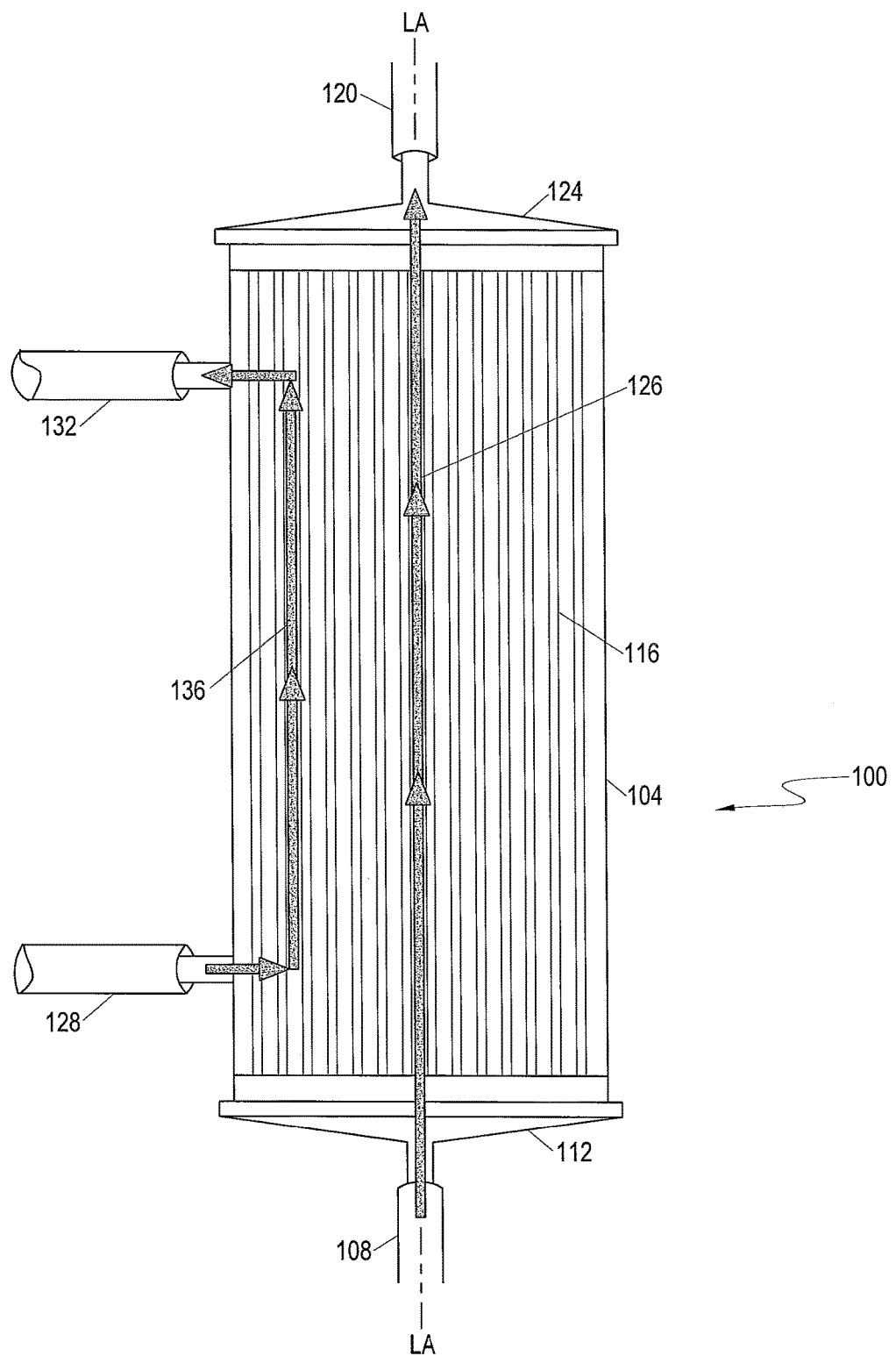
FIG. 1 illustrates a perspective view of a hollow fiber bioreactor in accordance with embodiments of the present disclosure.

With reference now to FIG. 1, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132. It should be noted that like elements are represented by like numerals in all of the Figures.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber via the EC inlet port 128 is in contact with the outside of the hollow fibers 116. Small molecules (e.g., ions, water, oxygen, lactate, etc.) can diffuse through the hollow fibers from the interior or IC space of the hollow fiber to the exterior or EC space, or from the EC space to the IC space. Large molecular weight molecules such as growth factors are typically too large to pass through the hollow fiber membrane, and remain in the IC space of the hollow fibers. The media may be replaced as needed. Media may also be circulated through an oxygenator 232 (FIG. 2) to exchange gasses as needed. Cells can be contained within the first circulation path 202 and/or second circulation path 204 as described below, and can be on either the IC side and/or EC side of the membrane.

The material used to make the hollow fiber membrane may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, or by exposing the surface to radiation. A gamma irradiated polysulfone-based membrane for cell expansion is described in WO 2010/034466. Gamma treating the membrane surface allows for attachment of adherent cells without additionally coating the membrane with fibronectin or the like. Bioreactors made of gamma treated membranes can be reused.

Figure 2:
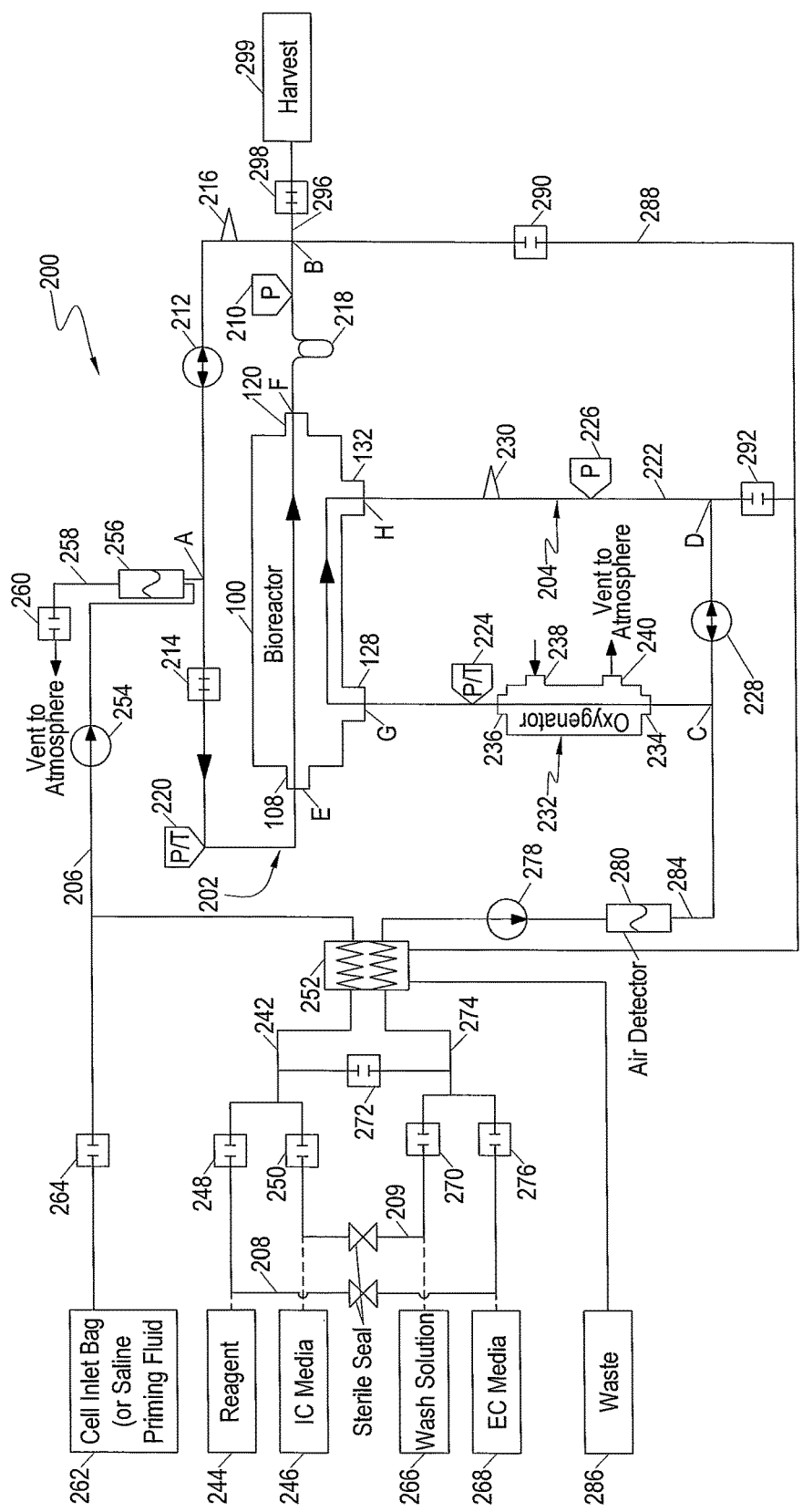
FIG. 2 depicts a schematic of one embodiment of a cell expansion system.

Referring now to FIG. 2, a schematic of one possible embodiment of a cell expansion system (CES) which may be used with the present disclosure is shown. In this embodiment and in all the examples or protocols below, the cells are grown in the IC space. CES 200 includes first fluid circulation path 202 (also referred to as the "intracapillary loop" or "IC loop") and second fluid circulation path 204 (also referred to as the "extracapillary loop" or "EC loop"). First fluid flow path 206 is fluidly associated with cell growth chamber 100 to form first fluid circulation path 202. Fluid flows into cell growth chamber 100 through IC inlet port 108, through hollow fibers in cell growth chamber 100, and exits via IC outlet port 120. Pressure gauge 210 measures the pressure of media leaving cell growth chamber 100. Media flows through IC circulation pump 212 which can be used to control the rate of media flow. IC circulation pump 212 may pump the fluid in a first direction or second direction opposite the first direction. Exit port 120 can be used as an inlet in the reverse direction. Media entering the IC loop may enter through valve 214. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES and modifications to the schematic shown are within the scope of the one or more present embodiments.

With regard to the IC loop, samples of media can be obtained from sample port 216 or sample coil 218 during operation. Pressure/temperature gauge 220 disposed in first fluid circulation path 202 allows detection of media pressure and temperature during operation. Media then returns to IC inlet port 108 to complete fluid circulation path 202. Cells grown/expanded in cell growth chamber 100 can be flushed out of cell growth chamber 100 into harvest bag 299 through valve 298 or redistributed within the hollow fibers for further growth. This will be described in more detail below. In this example, cells are grown in the IC space.

Fluid in second fluid circulation path 204 enters cell growth chamber 100 via EC inlet port 128, and leaves cell growth chamber 100 via EC outlet port 132. Media in the EC loop is in contact with the outside of the hollow fibers in the cell growth chamber 100, thereby allowing diffusion of small molecules into and out of the hollow fibers.

Pressure/temperature gauge 224 disposed in the second fluid circulation path 204 allows the pressure and temperature of media to be measured before the media enters the EC space of the cell growth chamber 100. Pressure gauge 226 allows the pressure of media in the second fluid circulation path 204 to be measured after it leaves the cell growth chamber 100. With regard to the EC loop, samples of media can be obtained from sample port 230 or a sample coil (not shown) during operation.

After leaving EC outlet port 132 of cell growth chamber 100, fluid in second fluid circulation path 204 passes through EC circulation pump 228 to oxygenator 232. EC circulation pump 228 may also pump the fluid in opposing directions. Second fluid flow path 222 is fluidly associated with oxygenator 232 via oxygenator inlet port 234 and oxygenator outlet port 236. In operation, fluid media flows into oxygenator 232 via oxygenator inlet port 234, and exits oxygenator 232 via oxygenator outlet port 236. Oxygenator 232 adds oxygen to and removes bubbles from media in the CES. In various embodiments, media in second fluid circulation path 204 is in equilibrium with gas entering oxygenator 232. The oxygenator 232 can be any appropriately sized oxygenator or gas transfer device known in the art. Air or gas flows into oxygenator 232 via filter 238 and out of oxygenator or gas transfer device 232 through filter 240. Filters 238 and 240 reduce or prevent contamination of oxygenator 232 and associated media. Air or gas purged from the CES 200 during portions of a priming sequence can vent to the atmosphere via the oxygenator 232.

In the configuration depicted for CES 200, fluid media in first fluid circulation path 202 and second fluid circulation path 204 flows through cell growth chamber 100 in the same direction (a co-current configuration). The CES 200 can also be configured to flow in a counter-current conformation.

In accordance with at least one embodiment, media, such as cells (from bag 262), and fluid media from bag 246 can be introduced to first fluid circulation path 202 via first fluid flow path 206. Fluid containers, or media bags, 244 (e.g., Reagent) and 246 (e.g., IC Media) may be fluidly associated with either first fluid inlet path 242 via valves 248 and 250, respectively or second fluid inlet path 274 via valves 270 and 276. First and second sterile sealable input priming paths 208 and 209 are provided. Air removal chamber (ARC) 256 is fluidly associated with first circulation path 202. The air removal chamber 256 may include one or more ultrasonic sensors including an upper sensor 1268 and lower sensor 1264 to detect air, a lack of fluid, and/or a gas/fluid interface, e.g., an air/fluid interface, at certain measuring positions within the air removal chamber 256 (see FIG. 6). For example, ultrasonic sensors may be used near the bottom and/or near the top of the air removal chamber 256 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 200 during portions of the priming sequence or other protocols can vent to the atmosphere out air valve 260 via line 258 that is fluidly associated with air removal chamber 256.

Fluid container 262 (e.g., Cell Inlet Bag (or Saline Priming Fluid for priming air out of the system)) is fluidly associated with the first fluid circulation path 202 via valve 264.

EC media (from bag 268) or wash solution (from bag 266) may be added to either the first or second fluid flow path. Fluid container 266 may be fluidly associated with valve 270 that is fluidly associated with first fluid circulation path 202 via distribution valve 272 and first fluid inlet path 242. Alternatively, fluid container 266 can be fluidly associated with second fluid circulation path 204 via second fluid inlet path 274 and second fluid flow path 284 by opening valve 270 and closing distribution valve 272. Likewise, fluid container 268 is fluidly associated with valve 276 that may be fluidly associated with first fluid circulation path 202 via first fluid inlet path 242 and distribution valve 272. Alternatively, fluid container 268 may be fluidly associated with second fluid inlet path 274 by opening valve 276 and closing valve distribution 272.

An optional heat exchanger 252 may be provided for media reagent or wash solution introduction.

In the IC loop, fluid is initially advanced by the IC inlet pump 254. In the EC loop, fluid is initially advanced by the EC inlet pump 278. An air detector 280, such as an ultrasonic sensor, may also be associated with the EC inlet path 284.

In at least one embodiment, first and second fluid circulation paths 202 and 204 are connected to waste line 288. When valve 290 is opened, IC media can flow through waste line 288 and to waste bag 286. Likewise, when valve 292 is opened, EC media can flow through waste line 288 to waste bag 286.

Cells can be harvested via cell harvest path 296. Here, cells from cell growth chamber 100 can be harvested by pumping the IC media containing the cells through cell harvest path 296 and valve 298 to cell harvest bag 299.

Various components of the CES 200 can be contained or housed within an incubator machine or housing 304 (FIG. 3), wherein the incubator maintains cells and media at a desirable temperature.

Figure 3:
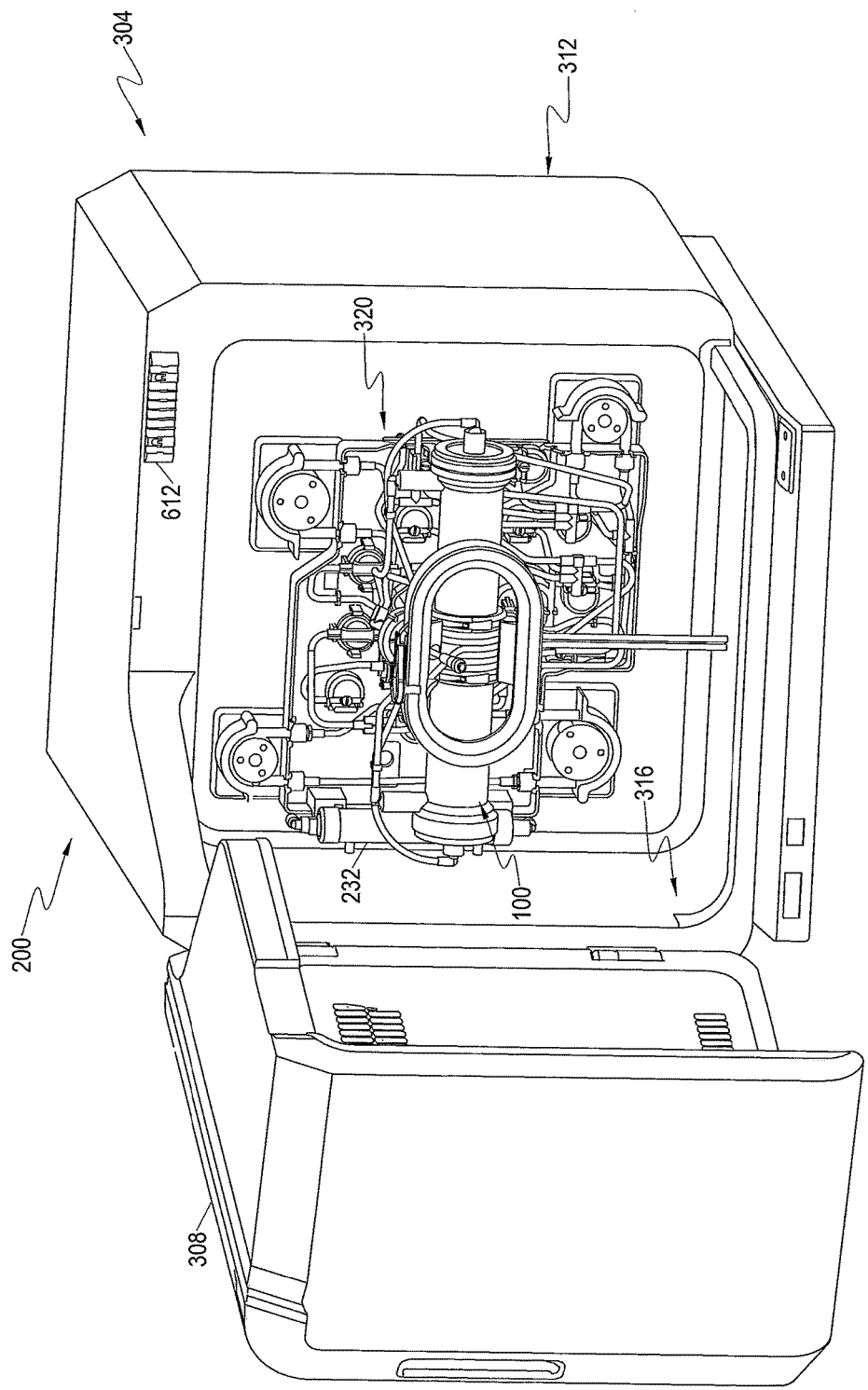
FIG. 3 illustrates a perspective view of the cell expansion system with a pre-mounted fluid conveyance device in accordance with embodiments of the present disclosure.

With reference now to FIG. 3, an embodiment of a CES 200 is shown. The CES 200 includes a cell expansion housing or machine 304 that comprises a hatch or closable door 308 for engagement with a back portion 312 of the cell expansion machine 200. An interior space 316 within the cell expansion machine 304 includes features adapted for receiving and engaging a premounted fluid conveyance assembly 320. The premounted fluid conveyance assembly 320 is detachably-attachable to the cell expansion machine 200 to facilitate relatively quick exchange of a new or unused premounted fluid conveyance assembly 320 at a cell expansion machine 200 for a used premounted fluid conveyance assembly 320 at the same cell expansion machine 200. Advantageously, a single cell expansion machine 304 can be operated to grow or expand a first set of cells using a first premounted fluid conveyance assembly 320, and thereafter, used to grow or expand a second set of cells using a second premounted fluid conveyance assembly 320 without needing to be sanitized between interchanging the first premounted fluid conveyance assembly 320 for the second premounted fluid conveyance assembly 320. The premounted fluid conveyance assembly includes the bioreactor 100 and the oxygenator 232. Tubing guide slots are shown as 612 for receiving various media tubing connected to premounted fluid conveyance assembly 320.

Figure 4:
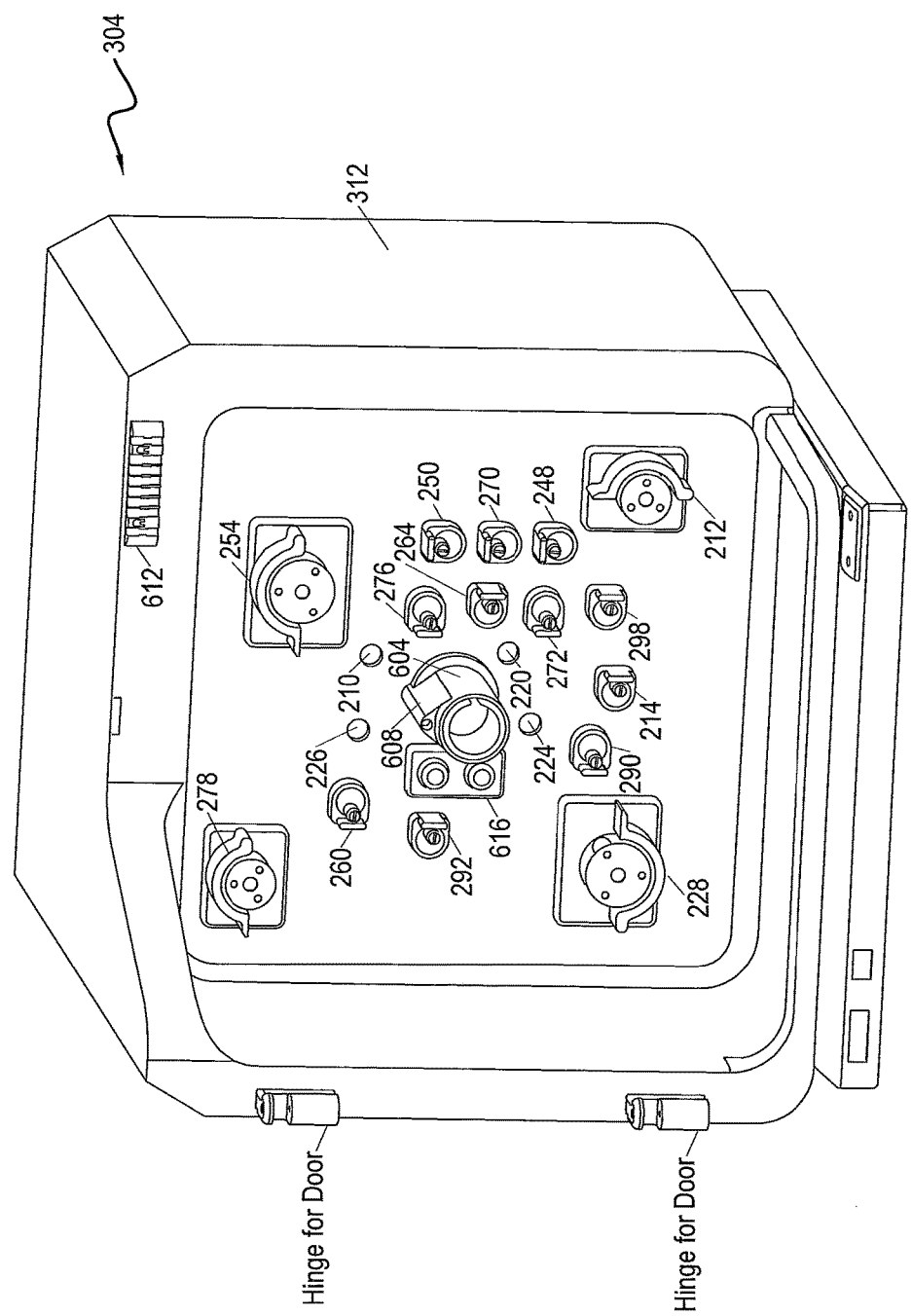
FIG. 4 depicts a perspective view of the housing of the cell expansion system in accordance with embodiments of the present disclosure.

Referring now to FIG. 4, the back portion 312 of a cell expansion machine 304 is shown prior to detachably-attaching a premounted fluid conveyance assembly 320. For clarity, the closable door 308 (shown in FIG. 3) is omitted from FIG. 4. The back portion 312 of the cell expansion machine 304 includes a number of different structures for working in combination with elements of a premounted fluid conveyance assembly 320. More particularly, the back portion 312 of the cell expansion machine 304 includes a plurality of peristaltic pumps for cooperating with pump loops 404 (FIG. 5), including the IC circulation pump 212, the EC circulation pump 228, the IC inlet pump 254, and the EC inlet pump 278. In addition, the back portion 312 of the cell expansion machine 104 includes a plurality of valves, including the IC circulation valve 214, the reagent valve 248, the IC media valve 250, the air removal valve 260, the cell inlet valve 264, the wash valve 270, the distribution valve 272, the EC media valve 276, the IC waste valve 290, the EC waste valve 292, and the harvest valve 298. Several sensors are also associated with the back portion 312 of the cell expansion machine 304, including the IC outlet pressure sensor 210, the combination IC inlet pressure and temperature sensors 220, the combination EC inlet pressure and temperature sensors 224, and the EC outlet pressure sensor 226. Also shown is the optical sensor 616 for the air removal chamber 256.

Referring still to FIG. 4, a shaft or rocker control 604 for rotating the bioreactor 100 is shown. Shaped fitting 608 associated with the shaft 604 allows for proper alignment of a shaft access aperture 324 (FIG. 5) of the tubing-organizer 300 of the premounted conveyance assembly with the back portion 312 of the cell expansion machine 304. Rotation of rocker control 604 imparts rotational movement to shaft fitting 508 (FIG. 5) and bioreactor 100. Thus, when an operator of the CES 200 attaches a new or unused premounted fluid conveyance assembly 320 to the cell expansion machine 304, the alignment is a relatively simple matter of properly orienting the shaft access aperture 324 of the premounted fluid conveyance assembly 320 with the shaped fitting 608.

Figure 5:
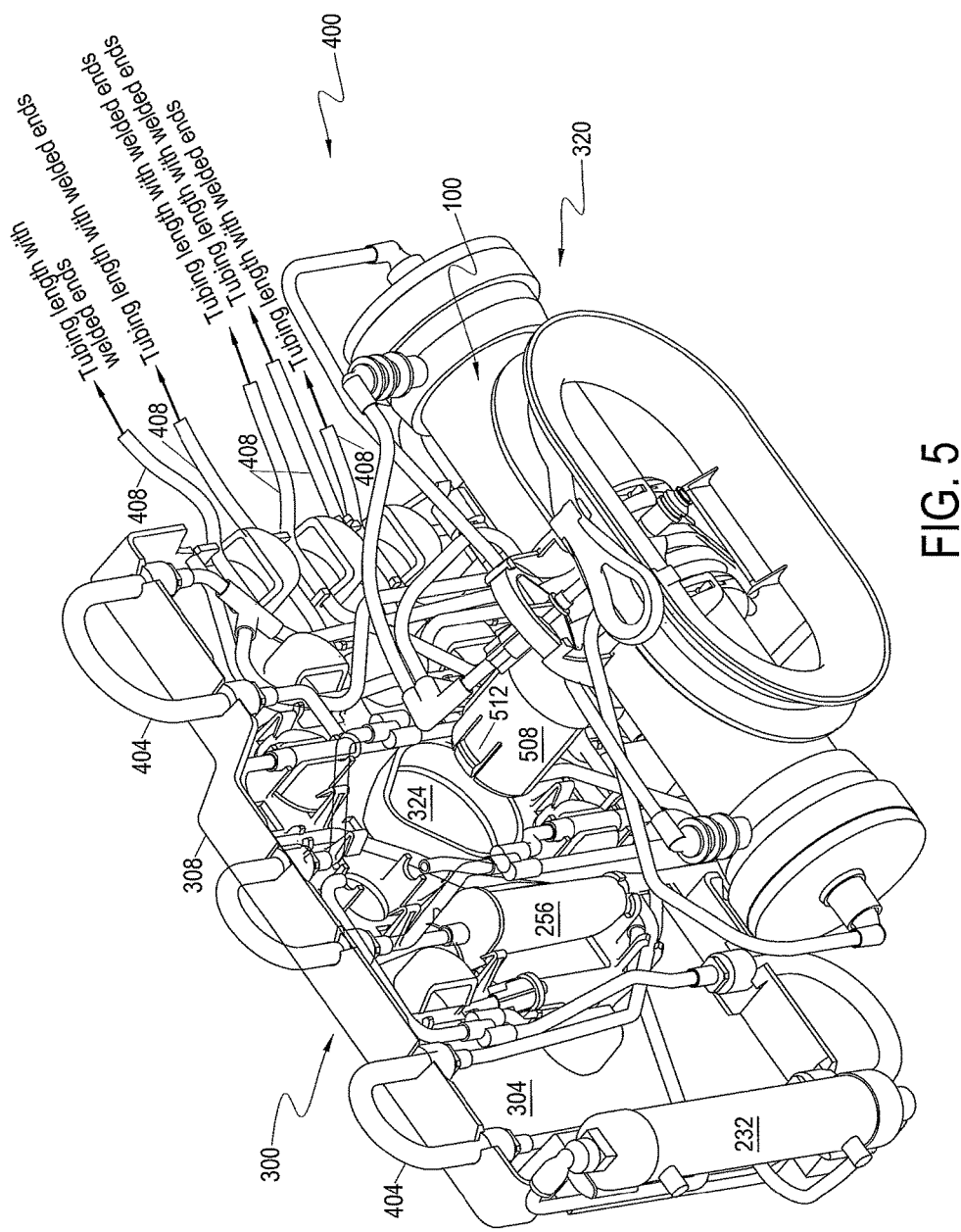
FIG. 5 illustrates a perspective view of the pre-mounted fluid conveyance device in accordance with embodiments of the present disclosure.

Referring now to FIG. 5, a perspective view of a detachably-attachable premounted fluid conveyance assembly 320 is shown. The premounted fluid conveyance assembly 320 is detachably-attachable to the cell expansion housing 304 to facilitate relatively quick exchange of a new or unused premounted fluid conveyance assembly 320 at a cell expansion machine 304 for a used premounted fluid conveyance assembly 320 at the same cell expansion machine 304. As shown in FIG. 5, the bioreactor 100 is attached to a bioreactor coupling that includes a shaft fitting 508. The shaped fitting 508 includes one or more shaft fastening mechanisms, such as a biased arm or spring member 512 for engaging a shaft (shown in FIG. 4) of the cell expansion machine 304.

Referring still to FIG. 5, the premounted fluid conveyance assembly 320 typically includes tubing 408 and various tubing fittings 412 to provide the fluid paths shown in FIG. 2. Pump loops 404 are also provided for the pump. Although the various media are typically provided at the site where the cell expansion machine 304 is located, the premounted fluid conveyance assembly 320 typically includes sufficient tubing length to extend to the exterior of the cell expansion machine 304 and to enable welded connections to tubing associated with the media bags.

Figure 6:
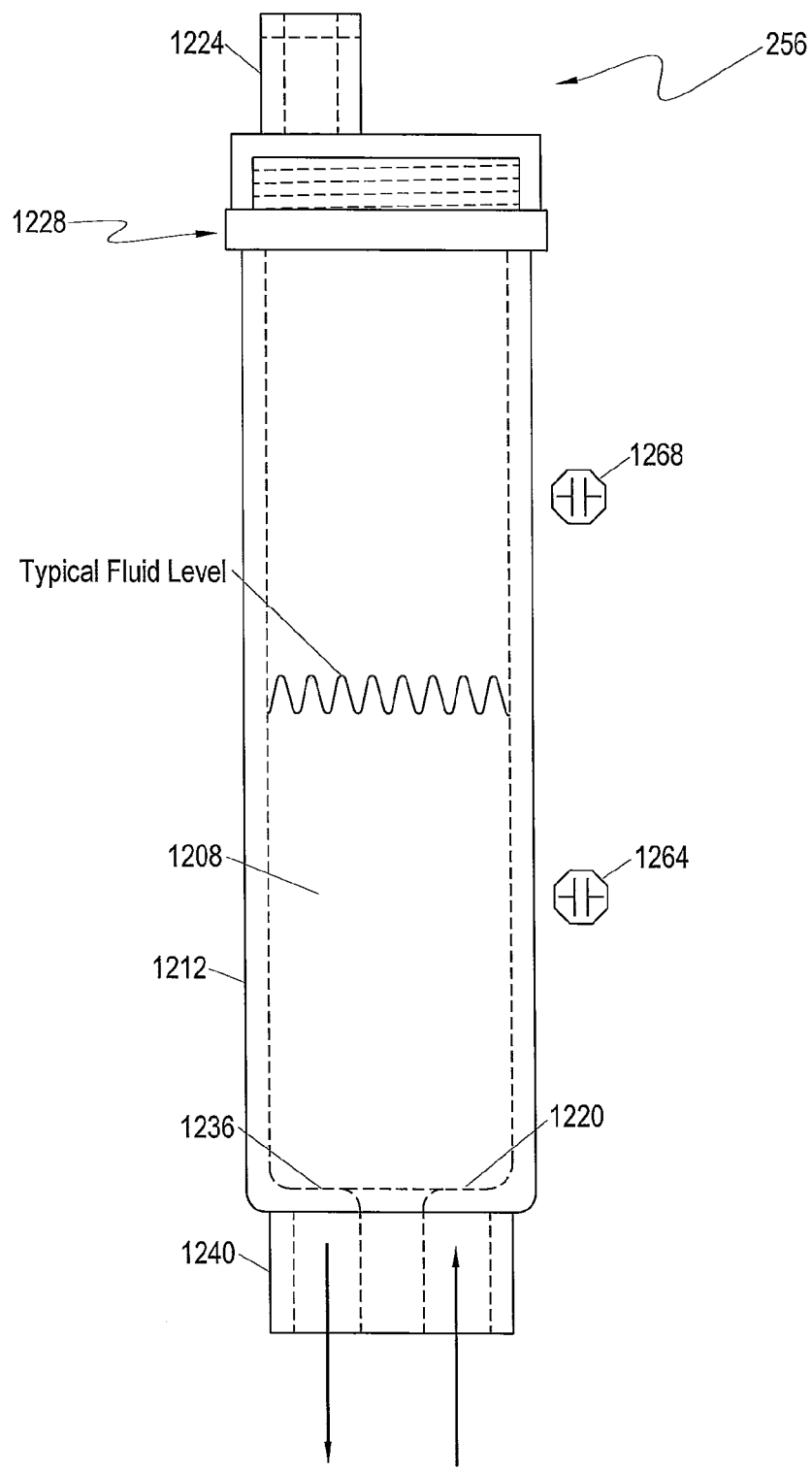
FIG. 6 depicts a perspective view of the air removal chamber in accordance with embodiments of the present disclosure.

The air removal chamber or ARC will now be described with respect with FIG. 6. In accordance with at least one embodiment, the air removal chamber 256 is mounted in a substantially vertical orientation on the premounted fluid conveyance assembly 320, such that air or gas bubbles within the fluid rise upward away from the bottom 1212 toward the vent aperture 1224 preferably located at the top 1228 along the vertical direction of the air removal chamber 256, or at least vertically above the fluid entrance aperture 1220 and fluid exit aperture 1236.

Referring again to FIG. 6 in at least one embodiment a plurality of fluid level sensors is used in combination with the air removal chamber 256. In at least one embodiment, the sensors are located on the cell expansion machine 304 at 616. More particularly, while the air removal chamber 256 is connected to a premounted fluid conveyance assembly 320 that can be detachably-attached to the cell expansion machine 304, the fluid level sensors for the air removal chamber 256 form part of the cell expansion machine 304.

In accordance with at least one embodiment, at least two sensors are used with the air removal chamber 256 to provide "high" and "low" fluid level sensing capability. Accordingly, operating protocol for the CES 100 includes monitoring the fluid level within the air removal chamber 256 and adjusting the pumping rate of the peristaltic pumps as necessary to maintain an appropriate fluid level within the fluid containment chamber 1208 of the air removal chamber. This operating protocol may include increasing or decreasing the pumping rates associated with pumps on either one or both the upstream and downstream sides of the air removal chamber 256. The ARC as described below also functions as a stop indication for various protocols.

In at least one embodiment, a first fluid level sensor 1264 (or low level fluid sensor) is situated to detect a fluid level in the air removal chamber 256 at a level of approximately ¼ full, and a second fluid level sensor 1268 (or high level fluid sensor) is situated to detect a fluid level in the air removal chamber 256 at a level of approximately ¾ full. The position of the fluid level sensors 1264 and 1268 allow the fluid level within the air removal chamber 256 to be adjusted to ensure that air does not pass though the fluid exit aperture 1236 and enter the fluid exit tube 1240 at the bottom 1212 of the air removal chamber 256 because of too low a fluid level, and that fluid does not exit through vent aperture 1224 located at the top 1228 of the air removal chamber 256 because of too high a fluid level.

As will be recognized by those of skill in the art, any number of fluid containers (e.g., media bags) can be fluidly associated with the CES in any combination.

Protocols will now be described with respect to the schematic described in FIG. 2, in accordance with embodiments of the present disclosure.

The following is a definition section for the Protocols described below. Points A through H on the schematic of FIG. 2 are also described in the definition section below. In the protocols or examples described the definition section may be referenced for various descriptions.

Protocols Parameter Definitions

| Parameter | Value | Explanations |
|---|---|---|
| VOLUME (mL) | | |
| $V_{ICL}$ | 189.1 | IC Loop Volume, $V_{BRIC} + 2V_{BRICH} + V_{EF}$ |
| $V_{ECL}$ | 305.6 | EC Loop Volume, $V_{BREC} + V_{GH}$ |
| $V_{ICBL}$ | 29.3 | Volume from bags to IC Loop, ARC volume is assumed to be 10 mL, inlet bag length assumed to be 3 mL |
| $V_{ECBL}$ | 18.5 | Volume from bags to EC Loop, inlet bag length assumed to be 3 mL |
| $V_{ICE}$ | 218.4 | IC Exchange volume = $V_{ICL} + V_{ICBL}$ |
| $V_{ECE}$ | 324.1 | EC Exchange volume = $V_{ECL} + V_{ECBL}$ |
| $V_{ABI}$ | 9 | Point "A" on FIG. 2 to Bioreactor inlet (includes header volume), excludes value directly from ARC to T-junction |
| $V_{ABO}$ | 42.1 | Point "A" of FIG. 2 to Bioreactor outlet (includes header volume), excludes value directly from ARC to T-junction |
| $V_{AB}$ | 32.6 | Volume from point "A" to point "B" of FIG. 2 |
| $V_{CD}$ | 3.8 | Volume from point "C" to point "D" of FIG. 2 |
| $V_{ARC}$ | 11.1 | Volume used to flush ARC contents into IC Loop = $V_{ARCA} + V_{ARCBS}$ |
| $V_{BRIC}$ | 138 | Volume of the IC side of bioreactor, excludes headers |
| $V_{BRICH}$ | 4.5 | Volume of IC header |
| $V_{EF}$ | 42.1 | Volume from Point "E" to Point "F" IC loop of FIG. 2 excluding bioreactor |
| $V_{BREC}$ | 266 | Volume of the EC side of the bioreactor |
| $V_{GH}$ | 39.6 | Volume from Point "G" to Point "H" EC loop of FIG. 2 excluding bioreactor |
| $V_{FA}$ | 37.6 | Volume from Point "F" to Point "A" IC loop of FIG. 2 excluding bioreactor |
| $V_{EA}$ | 4.5 | Volume from Point "E" to Point "A" IC loop of FIG. 2 excluding bioreactor |
| $V_{ARCA}$ | 4.1 | Volume from the bottom sensor of the ARC to Point "A" of FIG. 2 |
| $V_{ARCBS}$ | 7 | Volume of ARC between sensors |
| $V_{ARCF}$ | 2 | Volume to fill above ARC top sensor |
| $V_{FTO}$ | 40.2 | (1 + LP %/100) * $V_{ICBL}$ + 5 mL |
| $V_{PICBR}$ | 157.4 | Line volume being primed for IC side of bioreactor |
| $V_{PICCP}$ | 33 | Line volume being primed for IC Circulation pump |
| $V_{PECCP}$ | 4.6 | Line volume being primed for EC Circulation pump |
| $V_{PREL}$ | 20.9 | Line volume being primed for Reagent/EC Media loop |
| $V_{PWIL}$ | 20 | Line volume being primed for Wash/IC Media loop |
| $V_{PECBR}$ | 308.3 | Line volume being primed for Dist. Valve and EC bioreactor |
| $V_{ICPARC}$ | 6.5 | Volume from the bottom of the ARC to the IC inlet pressure pod includes pressure pod. |
| $V_{MTBS}$ | 18.6 | Maximum volume to bottom ARC sensor |
| $V_{MTTS}$ | 25.6 | Maximum volume to top ARC sensor ($V_{MTBS} + V_{ARCBS}$) |
| $V_{MTECS}$ | 33.1 | Maximum volume to EC fluid sensor |
| $V_{ABO}$ % | 82.4% | = $V_{ABO}$ * 100/($V_{ABI} + V_{ABO}$) |

| Parameter | Value | Explanations |
|---|---|---|
| AB % | 17.2% | = $V_{AB} * 100/V_{ICL}$ |
| CD % | 1.2% | = $V_{CD} * 100/V_{ECE}$ |
| SP % | 20% | Pump error to be added to a volume from a small pump |
| LP % | 20% | Pump error to be added to a volume from a large pump |
| | | POINTS ON HYDRAULIC LAYOUT AS SHOWN ON FIG. 2 |
| A | | T-junction immediately below the ARC where IC fluid enters the IC loop. |
| B | | Location in the IC Loop where fluid leaves the loop on its way to the Waste Bag |
| C | | T-junction where EC fluid enters the EC loop. |
| D | | Location in the EC Loop where fluid leaves the loop on its way to the Waste Bag. |
| E | | Location in the IC Loop where the line meets the IC Inlet header. |
| F | | Location in the IC Loop where the line meets the IC Outlet header. |
| G | | Location in the EC Loop where the line meets the EC Inlet of the bioreactor. |
| H | | Location in the EC Loop where the line meets the EC Outlet of the bioreactor. |
| | | PUMP RATES (mL/min) |
| $Q_{ICA}$ | | IC Inlet Pump rate (mL/min) |
| $Q_{ICC}$ | | IC Circulation Pump rate (mL/min) |
| $Q_{ECA}$ | | EC Inlet Pump rate (mL/min) |
| $Q_{ECC}$ | | EC Circulation Pump rate (mL/min) |
| $Q_{ECCM}$ | 30 | EC Circulation Pump rate to keep EC Loop well mixed |
| $Q_{ECCE}$ | 250 | EC circulation pump rate to equilibrate EC loop |
| $Q_{ICCM}$ | 20 | IC Circulation Pump rate to keep IC Loop well mixed while preventing air from entering the bioreactor fibers ($Q_{ICC} + Q_{ICA} = Q_{ICCM}$) |
| $Q_{ICCE}$ | 100 | IC circulation pump rate to equilibrate IC loop |
| $Q_{ECAUF}$ | 50 | EC Inlet rate to create ultra filtration |
| $Q_{ARC}$ | 200 | Max flow rate that does not cause air entrapment when ARC fluid level is at low level sensor when running |
| $Q_{FARC}$ | 40 | IC Inlet pump rate (mL/min) used to fill ARC. |
| $UFR_{400}$ | 60 | Negative UFR required to insure zero TMP at the bioreactor outlet when in co-current flow and when IC Inlet rate = 400 mL/min and EC waste valve is closed. |
| | | TIME (min) |
| $T_{CM}$ | 10 | Time to equilibrate (condition) media |

Note: For all examples the initial position of the bioreactor 100 to define rocker control motion is as shown in FIG. 3 or parallel to the horizon.

Protocol 1: High Flux Cell Load in Bioreactor Example

In an embodiment, this protocol is to load the cells from cell inlet bag 262 into bioreactor 100 until the bag 262 is empty. This is a high flux load at a medium flow rate.

$V_{ICBL}$ is the volume from the bags such as cell inlet bag 262 to the IC loop 202. In this example, the $V_{ICBL}$ is 29.3 mL assuming the volume of the air removal chamber (ARC) is 10 mL and the inlet bag 262 length, such as cell inlet bag 262, is 3 mL.

For a high flux cell load, $V_{FTO}$ of air is needed in the cell inlet bag. $V_{FTO}$ is defined as $(1+LP\%/100)*V_{ICBL}+5$ mL. In this example, it is 40.2 mL. LP % is a percentage related to pump error volume and in this example may be 20%.

The High Flux Load Protocol conditions are:
1) Valve 264 is open.
2) Inlet Pump 254 pumps at 50 mL/min (can be within 20 to 100 mL/min range).
3) IC circulation pump 212 and EC inlet pump 278 are off.
4) EC circulation pump 228 is set at $Q_{ECCM}$ which is a rate selected to keep EC loop well mixed which in this example is 30 mL/min.
5) IC Valve 290 is open to waste.
6) The bioreactor 100 is rotated using the rocker control from −90° to 180° with 1 second rest at end points to distribute cells. Alternatively the bioreactor can be fixed.
7) The high flux cell load is stopped when air is detected in the air removal chamber or ARC by the lower air sensor 1264.
8) ARC valve 260 is open to vent ARC air to atmosphere.
9) The ARC is then filled with media (either reagent, IC media or wash solution by pump 254 to upper senor 1268). IC media may be at least 60 mL of media with protein.
10) Cells are chased from the ARC by the fill media of item 9) above to the bioreactor 100 with larger chase volumes spreading the cells toward the IC outlet 120.
11) The chase is stopped at a selected IC volume which in this example is 47 mL.

The following is a brief summary of Protocol High Flux Load with chase step.

Protocol 1 High Flux Load

Purpose of protocol: Loads cells into the bioreactor from the cell inlet bag until the bag is empty. This protocol does not use IC circulation to distribute the cells.

Step 1: Load Bioreactor

Purpose of Step: Loads the cells from the cell inlet bag into the bioreactor.

Precondition: Need at least $V_{FTO}$ of air in cell inlet bag.

| | Input Range |
|---|---|
| IC Source | Cell Inlet |
| EC Source | None |
| Stop Condition | ARC Stop |
| IC Inlet Rate (mL/min) | Default: 50 |
| | Range: 20 to 100 mL/min |
| IC Circulation Rate (mL/min) | Default: 0 |
| EC Inlet Rate (mL/min) | Default: 0 |
| EC Circulation Rate (mL/min) | Default: $Q_{ECCM}$ |
| | Range: 10 to 300 mL/min |

-continued

| | Input Range |
|---|---|
| Outlet | EC Waste |
| Rocker Control | On or in motion (−90°, 180, 1 sec) (Def) Range: full range Fixed (0°) Range: full range (deg) |
| Output: IC volume | rate as defined by Stop Condition |
| Output: EC volume | N/A |
| Output: Remaining time of step | ARC Stop as defined by Stop Condition |

Step 2: Chase to Bioreactor
Purpose of Step: Chases the cells from the ARC to the bioreactor. Larger chase volumes spread the cells and move them towards the IC outlet.
Precondition: Fill ARC

| | Input Range |
|---|---|
| IC Source | Reagent IC Media (Default) Wash EC Media |
| EC Source | None |
| Stop Condition | IC volume: $(V_{ARCA} + V_{ARCBS} + V_{EA}) * 3$ Range: 1 to 200 mL |
| IC Inlet Rate (mL/min) | Default: Same as Step 1 |
| IC Circulation Rate (mL/min) | Default: Same as Step 1 |
| EC Inlet Rate (mL/min) | Default: 0 |
| EC Circulation Rate (mL/min) | Default: Same as Step 1 |
| Outlet | EC Waste |
| Rocker Control | Same as Step 1 |
| Output: IC volume | Volume as defined by Stop Condition |
| Output: EC volume | N/A |
| Output: Remaining time of step | Countdown in minutes as defined by Stop Condition |

Protocol 2: Load Cells into Bioreactor with Circulation Example

In an embodiment, this alternative protocol loads the cells from the IC inlet bag 262 until it is empty to the bioreactor 100. It uses the IC circulation loop 202 for the load. The cell inlet bag contains at least $V_{FTO}$ of air. The IC circulation pump 212 permits load from both the inlet 108 and outlet 120 of bioreactor 100.

The conditions for the Protocol Load Cells into Bioreactor with Circulation are:
1) Valve 264 is open.
2) Inlet pump 254 operates at 50 mL/min within a range of 200 to 100 mL/min.
3) IC circulation rate using pump 212 is $V_{ICL}/\text{min} - Q_{ICA}$
   $V_{ICL}$ is the IC loop 202 volume or
   $V_{BRIC} + 2 V_{BRICH} + V_{EF}$
   $V_{BRIC}$ is the volume of the IC side of bioreactor 100 excluding headers. $V_{BRICH}$ is the volume of the headers. $V_{EF}$ is the volume of the IC loop from E to F on FIG. 2 excluding the bioreactor. $Q_{ICA}$ is the inlet pump rate. The range for the IC circulation rate is from 20 to 300 mL/min and depends on the IC inlet rate. In this example it is 139 mL/min.
4) EC inlet is O with default $Q_{ECCM}$ in a range from 10 to 300 mL/min.
5) The EC circulation rate is $Q_{ECCM}$, for example 30 mL/min.
6) The outlet the EC waste through valve 292.
7) Rocker control for the bioreactor 100 is −90° to 180° for 1 second stops at the ends of rotation or optionally the bioreactor may be fixed.
8) The stop condition is air detection by the ARC by the lower air sensor 1264.
9) After stop condition ARC is filled with desired media to upper sensor 1268 and chase liquid chases the cells from the ARC to the loop. The stop condition for chase is the IC volume $(V_{ARCA} + V_{ARCBS}) * 2$ in a range from 1 to 100. $V_{ARCA}$ is the volume from the ARC to point A on FIG. 2 and $V_{ARCBS}$ is the volume of the ARC between sensors 1268 and 1264.
10) To load the cells from the IC loop the IC circulation rate is $-V_{ABO}\%$ of $Q_{ICA}$. $-V_{ABO}\%$ is $V_{ABO}*100 / V_{ABI} + V_{ABO}$. $V_{ABO}$ is the volume from point A to the bioreactor 100 outlet (point F) and in this example is 42.1 mL. $Q_{ICA}$ is the inlet pump rate as described above. $V_{ABI}$ is the volume from point A to inlet 108 with $V_{ABO}$ being the volume from point A to outlet 120.
11) The stop condition for the load is the IC volume $1.5 \times V_{EF}$. The range is $0.5 V_{EF}$ to $2.0 V_{EF}$. $V_{EF}$ is the volume of the IC loop 202 from point E to F excluding the bioreactor.

Below is a summary of the circulation load.

Protocol 2 Load with Circulation
Purpose of protocol: Loads the cells into the bioreactor from the cell inlet bag until the bag is empty, and uses IC circulation to distribute the cells.

Step 1: Load IC Loop
Purpose of Step: Loads the cells into the system.
Precondition: Need at least $V_{FTO}$ of air in cell inlet bag.

| | Input Range |
|---|---|
| IC Source | Cell Inlet |
| EC Source | None |
| Stop Condition | ARC Stop |
| IC Inlet Rate (mL/min) | Default: 50 Range: 20 to 100 mL/min |
| IC Circulation Rate (mL/min) | Default: $V_{ICL}/\text{min} - Q_{ICA}$ Range: 20 to 300 mL/min |
| EC Inlet Rate (mL/min) | Default: 0 |
| EC Circulation Rate (mL/min) | Default: $Q_{ECCM}$ Range: 10 to 300 mL/min |
| Outlet | EC Waste |
| Rocker Control | On (−90°, 180°, 1 sec) (Def) Range: Full Range (deg, time) Fixed (0°) Range: full range (deg) |
| Output: IC volume | rate as defined by Stop Condition |
| Output: EC volume | N/A |
| Output: Remaining time of step | ARC stop as defined by Stop Condition |

Note:
$Q_{ICA}t + Q_{ICC}t = nV_{ICL}$

Step 2: ARC Chase
Purpose of Step: Chases the cells from the ARC into the IC loop.
Precondition: Fill ARC

| | Input Range |
|---|---|
| IC Source | Reagent IC Media (Default) Wash EC Media |
| EC Source | None |
| Stop Condition | IC volume: $(V_{ARCA} + V_{ARCBS}) * 2$ Range: 1 to 100 |
| IC Inlet Rate (mL/min) | Default: Same as Step 1 |
| IC Circulation Rate (mL/min) | Default: Same as Step 1 |
| EC Inlet Rate (mL/min) | Default: 0 |
| EC Circulation Rate (mL/min) | Default: Same as Step 1 |
| Outlet | EC Waste |
| Rocker Control | Same as Step 1 |
| Output: IC volume | Volume as defined by Stop Condition |
| Output: EC volume | N/A |

-continued

| | Input Range |
|---|---|
| Output: Remaining time of step | Countdown in minutes or manual stop as defined by Stop Condition |

Step 3: Load Bioreactor

Purpose of Step: Chases the cells from the IC loop into the bioreactor.

| | Input Range |
|---|---|
| IC Source | Reagent |
| | IC Media (Default) |
| | Wash |
| | EC Media |
| EC Source | None |
| Stop Condition | IC volume: 1.5 × $V_{EF}$ (Default) |
| | Range: $0.5V_{EF}$ to $2.0V_{EF}$ |
| IC Inlet Rate (mL/min) | Default: Same as Step 1 |
| IC Circulation Rate (mL/min) | Default: $-V_{ABO}$ % of $Q_{ICA}$ |
| EC Inlet Rate (mL/min) | Default: 0 |
| EC Circulation Rate (mL/min) | Default: Same as Step 1 |
| Outlet | EC Waste |
| Rocker Control | Same as Step 1 |
| Output: IC volume | Volume as defined by Stop Condition |
| Output: EC volume | N/A |
| Output: Remaining time of step | Countdown in minutes as defined by Stop Condition |

Protocol 3: Bone Marrow Washout Example

In an embodiment, this protocol is to remove non-attached/non-adhered cells from the bioreactor. It is for 25 mL to 62 mL bone marrow load though it could be used for load above 10 mL. The bone marrow washout generally follows bone marrow load. It can also be a wash out protocol when the bioreactor is packed with a large number of cells though this protocol is typically done after an initial load. The types of cells removed include red blood cells, platelets and non-adherent bone marrow cells.

The protocol includes the following:

1) IC media introduced through valve 250. This may be approximately 500 mL with protein. Optionally wash or EC media could be introduced.

2) EC media is generally media without protein introduced through valve 276. Optionally wash or IC media could be introduced on EC side.

3) IC inlet rate (mL/min) through pump 254 is expressed as follows:

$$= \begin{vmatrix} 0, & 0 < t \le t_1 \\ 20 + ((Q/2) - 20) \times ((t - t_1)/t_1), & t_1 < t \le t_2 \\ (Q/2) + (Q/2) \times ((t - t_2)/(t_3 - t_2)), & t_2 < t \le t_3 \\ 0, & t_3 < t \end{vmatrix}$$

In this example the maximum is 100 mL/min.

4) IC circulation rate is expressed as follows: $-AB\% * Q_{ICA}$ $AB\% = V_{AB} * 100/V_{ICL}$ $V_{AB}$=volume from point A to B on FIG. 2

$V_{ICL}$=IC loop volume

5) EC inlet rate (mL/min)

$$= \begin{vmatrix} 20 + ((Q/2) - 20) \times (t/t_1), & 0 < t \le t_1 \\ Q/2 & t_1 < t \le t_2 \\ (Q/2) - (Q/2) \times ((t - t_2)/(t_3 - t_2)), & t_2 < t \le t_3 \\ 0, & t_3 < t \end{vmatrix}$$

6) The parameters for both the IC inlet and EC inlets rates are defined in the table following:

| Parameter | Equation |
|---|---|
| V | User input – Total IC + EC volume to be pumped (mL). |
| Q | User input – Maximum IC inlet rate (mL/min). Q >40 mL/min. |

$t_1$ (minutes) = V × ((2 × (Q − 40))/(3 × $Q^2$ − 40 × Q − 1600))
$t_2$ (minutes) = 2 × $t_1$; $t_3$ (minutes) = (5/2) × ((Q − 32)/(Q − 40)) × $t_1$ 7) EC circulation rate (mL/min)=$Q_{ECCM}$ of a range from 10 to 300 mL/min.
   $Q_{ECCM}$=rate to keep EC loop well mixed in this example 30 mL/min.

8) Rocker control for bioreactor 100 is on with −90°, 180°, for 1 second pause at the ends.

9) The stop condition in this example is an inlet volume of 1000 mL with a range from 400 to 4000.

10) Maximum flow rate of output washout is 100 mL in range from 80 to 200.

Summary of the protocol is below.

Protocol 3 Bone Marrow Washout

Purpose of protocol: Meant for use following a bone marrow load (25 mL to 62 mL) and attachment phase, this protocol is recommended to remove any non-attached/non-adhered cells from the bioreactor.

This is also a useful washout protocol for any occasion when the bioreactor is packed with a similar large number of cells. For bone marrow loads of 10 mL or less, Protocol Aggressive Washout is recommended. For bone marrow loads between 10 mL to 25 mL, this protocol is optional but may not be required.

Step 1: Bone Marrow Washout

| | Input Range |
|---|---|
| IC Source | IC Media (Default) |
| | Wash |
| | EC Media |
| EC Source | IC Media |
| | Wash |
| | EC Media (Default) |
| Stop Condition | Volume = 1000 Range: 400 to 4000 |
| Washout Parameters | Maximum Flow Rate (MFR) = 100 Range: 80 to 200 |
| IC Inlet Rate (mL/min) | $= \begin{vmatrix} 0, & 0 < t \le t_1 \\ 20 + \left(\left(\frac{Q}{2}\right) - 20\right) \times \left(\frac{(t - t_1)}{t_1}\right), & t_1 < t \le t_2 \\ \left(\frac{Q}{2}\right) + \left(\frac{Q}{2}\right) \times \left(\frac{(t - t_2)}{(t_3 - t_2)}\right), & t_2 < t \le t_3 \\ 0, & t_3 < t \end{vmatrix}$ where parameters are defined in table following. |
| IC Circulation Rate (mL/min) | Value: $-AB\% * Q_{ICA}$ |

-continued

| | Input Range |
|---|---|
| EC Inlet Rate (mL/min) | $= \begin{vmatrix} 20 + \left(\left(\frac{Q}{2}\right) - 20\right) \times \left(\frac{t}{t_1}\right) & 0 < t \leq t_1 \\ Q/2 & t_1 < t \leq t_2 \\ \left(\frac{Q}{2}\right) - \left(\frac{Q}{2}\right) \times \left(\frac{(t-t_2)}{(t_3-t_2)}\right) & t_2 < t \leq t_3 \\ 0, & t_3 < t \end{vmatrix}$ |
| EC Circulation Rate (mL/min) | Default: $Q_{ECCM}$<br>Range: 10 to 300 mL/min |
| Outlet | IC Waste |
| Rocker | On (−90°, 180°, 1 sec) Range: full range (deg, time) |
| Output: IC volume | Volume as defined by stop condition |
| Output: EC volume | Volume as defined by stop condition |
| Output: Remaining time of step | Countdown in minutes as defined by stop condition |

| Parameter | Equation |
|---|---|
| V | User input – Total IC + EC volume to be pumped (mL). |
| Q | User input – Maximum IC inlet rate (mL/min).<br>Q >40 mL/min. |

$t_1$ (minutes) = $V \times ((2 \times (Q - 40))/(3 \times Q^2 - 40 \times Q - 1600))$
$t_2$ (minutes) = $2 \times t_1$; $t_3$ (minutes) = $(5/2) \times ((Q - 32)/(Q - 40)) \times t_1$ Protocol 4: Aggressive Washout for Bone Marrow Loads below 10 mL Example In an embodiment, this protocol produces a small amount ultrafiltration into the hollow fiber of the bioreactor membrane 116 across the entire filter length. The purpose of the protocol is to remove non-adherent cells from the bioreactor. The protocol includes:
1) IC source is IC media introduced through valve 250 by pump 254. Alternatively the IC source could be reagent, wash, or EC media. The IC media may be media with protein estimated in this example to be about 500 mL.
2) EC source is EC media introduced through valve 276 by pump 278. Alternatively the EC source could be reagent, IC media, or wash. This may be media without protein.
3) IC pump 254 is set at approximately 260 mL/min inlet rate from a range of 50 to 500 mL/min.
4) IC circulation rate is −AB %*$Q_{ICA}$, in this example, −45 mL/min.
5) EC inlet rate is 40 mL/min from a range of 0 to 100 mL/min.
6) EC circulation rate is $Q_{ECCM}$ or the rate to keep the loop well mixed from a range of 10 to 300 mL/min, in this example 30 mL/min.
7) The IC source goes to waste.
8) The rocker control for the bioreactor 100 may be set at −90% to 180% for 1 second pause at the ends of the range of motion or optionally could be fixed.
9) The stop condition for the process may be based on time such as up to 60 minutes; IC volume as defined in the Bone Marrow Washout which may range from is from 0 to 4000 mL range; or the number of IC exchanges or number of times the IC source fluid is circulated. The number of IC exchanges may be 2.5 from a range of 0.5 to 5.0

Summary of the protocol is below.
Protocol 4 Aggressive Washout
Purpose of protocol: Removes non-adherent cells from the bioreactor. This protocol imposes a small ultrafiltration into the fiber across the entire fiber length.

Step 1: Aggressive Washout

| | Input Range |
|---|---|
| IC Source | Reagent<br>IC Media (Default)<br>Wash<br>EC Media |
| EC Source | Reagent<br>IC Media<br>Wash<br>EC Media (Default) |
| Stop Condition | Time: (1 min) Range: 0.1 to 60 min<br>IC volume: ($V_{ICE}$) Range: 1 to 4000 mL<br># of IC exchanges: 2.5 (default)<br>Range 0.5 to 5.0 |
| IC Inlet Rate (mL/min) | Default: 260<br>Range: 50 to 500 mL/min |
| IC Circulation Rate (mL/min) | Default: −AB % * $Q_{ICA}$ |
| EC Inlet Rate (mL/min) | Default: 40<br>Range: 0 to 100 mL/min |
| EC Circulation Rate (mL/min) | Default: $Q_{ECCM}$<br>Range: 10 to 300 mL/min |
| Outlet | IC Waste |
| Rocker Control | On (−90°, 180°, 1 sec) (Def)<br>Range: Full Range (deg, time)<br>Fixed (0°) Range: Full range (deg) |
| Output: IC volume | Volume as defined by Stop Condition |
| Output: EC volume | Volume as defined by Stop Condition |
| Output: Remaining time of step | Countdown in minutes as defined by Stop Condition |

Protocol 5: IC or EC Washout Example

In an embodiment, this protocol is to replace media while growing adherent cells. The protocol washes out cellular debris and non-adherent cells. The replacement volume is the number of IC and EC exchanges to be performed or IC or EC volume exchanged.

$V_{ICE}$ (IC exchange volume) equals IC loop volume plus volume from media, reagent or wash bags to IC loop.

$V_{ECE}$ (EC exchange volume) equals EC loop volume plus volume from media, reagent or wash bags to EC loop.

The protocol includes the following.
1) The IC source is IC media introduced through valve 250 by pump 254. Reagent, EC media, or wash solution may optionally be used. The IC media may be media with protein. In this example the volume may be at least 550 mL.
2) The EC source is EC media introduced through valve 276 by pump 278. Reagent, IC media, or wash solution may optionally be used. The EC media may be media without protein. In this example the volume may be at least 810 mL.
3) The IC inlet rate is $Q_{ECA}$ (number of IC Exc*$V_{ICE}$)/ (number of EC Exc*$V_{ECE}$)
$Q_{ECA}$=EC inlet pump rate
$V_{ICE}$=IC exchange volume which in this example is 218.4 mL.
$V_{ECE}$=EC exchange volume which in this example is 324.1 mL.
4) IC circulation rate is −AB %*$Q_{ICA}$ AB %=$V_{AB}$ (volume from point A to B in FIG. 2)*100/$V_{ICL}$. $V_{ICL}$ is IC loop volume.

$Q_{ICA}$=IC inlet pump 254 rate
5) The EC inlet rate is the lesser of $Q_{100}$ or $Q_{MAX}$ where $Q_{100}$=100 (number of EC Exc*$V_{ECE}$)(number of IC Exc*$V_{ICE}$) and $Q_{MAX}$=300

6) The EC circulation rate is −CD %*$Q_{ECA}$. CD %=$V_{CD}$ (or volume from point C to D, in this example 3.8 mL)*100/$V_{ECE}$.
7) The outlet for the media or washout fluid is either the IC, EC, or both waste 286.
8) The rocker control for the bioreactor 100 is −90° to 180° with 1 second pause at the end of the range of motion. Or alternatively, there is no rocker control motion.
9) The stop condition to end the process includes the number of IC exchanges (Exc.) which may be 2.5 or optionally within a range from 0.5 to 5. The stop condition also includes the number of EC exchanges which may be 2.5 or optionally within a range from 0.5 to 5.

A summary of this protocol is as follows.

Protocol 5 IC or EC Washout

Purpose of protocol: Meant for use when growing adherent cells to replace the media in both the IC loop and EC loop. This protocol provides some washout of cellular debris and non-adherent cells. The replacement volume is specified as the number of IC and EC exchanges to be performed.

Calculations:
One IC exchange volume ($V_{ICE}$) is equal to the IC Loop Volume plus the volume from bags to IC loop.
One EC exchange ($V_{ECE}$) is equal to the EC Loop Volume plus the volume from bags to EC Loop.

Step 1: Washout

|  | Input Range |
| --- | --- |
| IC Source | Reagent |
|  | IC Media (Default) |
|  | Wash |
|  | EC Media |
| EC Source | Reagent |
|  | IC Media |
|  | Wash |
|  | EC Media (Default) |
| Stop Condition | # of IC Exchanges: 2.5 (default) |
|  | range: 0.5-5.0 |
|  | # of EC Exchanges: 2.5 (default) |
|  | range: 0.5-5.0 |
| IC Inlet Rate (ml/min) | Value: $Q_{ECA}$ (# of IC Exc. * $V_{ICE}$)/ (# of EC Exc. * $V_{ECE}$) |
| IC Circulation Rate (ml/min) | Value: −AB % * $Q_{ICA}$ |
| EC Inlet Rate (ml/min) | Initial value: the lesser of $Q_{100}$ or $Q_{max}$; where $Q_{100}$ = 100 (# of EC Exc. * $V_{ECE}$)/(# of IC Exc. * $V_{ICE}$) and $Q_{max}$ = 300. |
| EC Circulation Rate (ml/min) | Value: −CD % * $Q_{ECA}$ |
| Outlet | EC Waste |
|  | IC Waste |
|  | IC&EC Waste (default) |
| Rocker Control | On (−90°, 180°, 1 sec) (Def) |
|  | Range: full range (deg, time) |
|  | Fixed (0°) Range: Full range (deg) |
| Output: IC volume | Volume as defined by Stop Condition |
| Output: EC volume | Volume as defined by Stop Condition |
| Output: Remaining time of step | Countdown in minutes as defined by Stop Condition |

Protocol 6: Washout through the Membrane Example

In an embodiment, this protocol is to move small molecular components on the IC side to the EC side of the membrane 116. These molecules pass through the membrane by diffusion or ultrafiltration. These could include bi-products of the cell growth. IC components retained by the membrane are not removed from the IC loop. The small molecular weight elements are washed out of the EC side by replacement fluid.

The replacement volume is specified by the number of IC volumes—EC volumes exchanged.

The protocol includes:
1) The introduction of IC media or optionally other media to the IC side. This may be media with protein.
2) The introduction of EC media or optionally other media to the EC side. This may be media without protein.
3) The IC inlet rate as described for IC/EC washout.

$Q_{ECA}$ (number of IC Exc*$V_{ICE}$)/(number of EC Exc*$V_{ECE}$)

4) The IC circulation rate is defined by −$V_{ABO}$%*$Q_{ICA}$.

$V_{ABO}$%=$V_{ABO}$*10$V_{ABI}$+$V_{ABO}$ $V_{ABO}$ is from point A to bioreactor outlet F on FIG. 2 and in this example is 42.1 mL.

$V_{ABI}$ is from point A to bioreactor inlet E on FIG. 2 and in this example is 9 mL.

5) The EC inlet rate is the lesser of $Q_{65}$ or $Q_{MAX}$ where $Q_{65}$ is defined the same as $Q_{100}$ for IC/EC washout above.
6) The EC circulation rate is −CD %*$Q_{ECA}$ as described above for IC/EC washout.
7) The outlet is EC waste.
8) The rocker control is the same for IC/EC washout.
9) The stop condition is the number of IC and EC exchanges which may be 1 or within the range of 0.5 to 5.

The brief summary is as follows.

Protocol 6 IC/EC Washout through Membrane

Purpose of protocol: Replaces small molecule components on IC side, which pass through the membrane by either diffusion or by ultra filtration. IC components retained by the membrane are not removed from the IC loop. Components on EC side are washed out by fluid replacement. The replacement volume is specified as the number of IC and EC exchanges to be performed.

Calculations:
One IC exchange volume ($V_{ICE}$) is equal to the IC Loop Volume plus the volume from bags to IC loop.
One EC exchange ($V_{ECE}$) is equal to the EC Loop Volume plus the volume from bags to EC Loop.

Step 1: Washout Through Membrane

|  | Input Range |
| --- | --- |
| IC Source | Reagent |
|  | IC Media (Default) |
|  | Wash |
|  | EC Media |
| EC Source | Reagent |
|  | IC Media |
|  | Wash |
|  | EC Media (Default) |
| Stop Condition | # of IC Exchanges: 1 (default) |
|  | range: 0.5-5.0 |
|  | # of EC Exchanges: 1 (default) |
|  | range: 0.5-5.0 |
| IC Inlet Rate (ml/min) | Value: $Q_{ECA}$ (# of IC Exc. * $V_{ICE}$)/ (# of EC Exc. * $V_{ECE}$) |
| IC Circulation Rate (ml/min) | Value: −$V_{ABO}$ % * $Q_{ICA}$ |
| EC Inlet Rate (ml/min) | Initial value: the lesser of $Q_{65}$ or $Q_{max}$; where $Q_{65}$ = 100 (# of EC Exc. * $V_{ECE}$)/(# of IC Exc. * $V_{ICE}$) and $Q_{max}$ = 300. |
| EC Circulation Rate (ml/min) | Value: −CD % * $Q_{ECA}$ |
| Outlet | EC Waste |
| Rocker | On (−90°, 180°, 1 sec) (def) |
|  | Range: full range (deg, time) |
|  | fixed(0°) Range: full range (deg) |

| | Input Range |
|---|---|
| Output: IC volume | Volume as defined by Stop Condition |
| Output: EC volume | Volume as defined by Stop Condition |
| Output: Remaining time of step | Countdown in minutes as defined by Stop Condition |

Protocol 7: Continuous Add of IC with Ultrafiltration Example

In an embodiment, this protocol adds generally IC fluid at a low flow rate and keeps large molecules on the IC side of the fiber. A similar protocol could be used to add fluid at low flow rate to the EC side. Excess IC fluid will be removed through ultrafiltration if the IC inlet pump 254 is used.

This protocol includes:

1) The IC media is introduced through valve 250 by pump 254 with other media being optional alternatives.
2) EC media may optionally be added but in the IC example the EC inlet flow rate is 0.
3) The IC inlet flow rate is 0.1 mL/min from a range of 0 to 10 mL/min.
4) The IC circulation rate through IC loop 202 is at a maximum of $Q_{ICCM}$, $10 \times Q_{ICA}$.

$Q_{ICCM}$ is the IC circulation pump rate to keep IC loop 202 well mixed without preventing air from entering filter 116. The inlet pump 254 rate $Q_{ICA}$ plus the circulation pump 212 rate equals the $Q_{ICCM}$ which in this example is 20 mL/min.
5) The EC circulation rate is $Q_{ECCM}$ or the pump 228 rate to keep the EC loop 204 well mixed, for example 30 mL/min.
6) The outlet for the excess IC fluid is EC waste as the fluid enters the EC loop 204 through ultrafiltration through the membrane.
7) The rocker control for bioreactor 100 is fixed.
8) The stop condition is a manual stop by the operator although alternatively the stop could be based on selected time or selected IC or EC volume.

Below is a summary of the Continuous Add with Ultrafiltration protocol.

Protocol 7 Continuous Add with Ultra Filtration

Purpose of protocol: Continuously adds fluid at a low flow rate to the IC loop and/or the EC loop. Large molecules may be concentrated in the IC loop if you use the IC Inlet pump for this task. This protocol uses ultrafiltration to remove excess IC fluid if you use the IC Inlet pump.

Step 1: Feed

| | Input Range |
|---|---|
| IC Source | Cell Inlet |
| | Reagent |
| | IC Media (Default) |
| | Wash |
| | EC Media |
| | None |
| EC Source | Reagent |
| | IC Media |
| | Wash |
| | EC Media (Default) |
| | None |
| Stop Condition | Time (1440 min) Range: 0.1 to 1440 minutes |
| | Manual Stop (Default) |
| | IC volume: (150 mL) Range: 1 to 4000 mL |
| | EC volume: (150 mL) Range: 1 to 4000 mL |

| | Input Range |
|---|---|
| IC Inlet Rate (ml/min) | Default: 0.1 |
| | Range: 0 to 10 mL/min |
| IC Circulation Rate (ml/min) | Default: Maximum of ($Q_{ICCM}$, $10 \times Q_{ICA}$) |
| | Range: −100 to 100 mL/min |
| EC Inlet Rate (ml/min) | Default: 0 |
| | Range: 0 to 10 mL/min |
| EC Circulation Rate (ml/min) | Default: $Q_{ECCM}$ |
| | Range: 10 to 300 mL/min |
| Outlet | EC Waste |
| Rocker Control | On (−90°, 180°, 1 sec) |
| | Range: full range (deg, time) |
| | Fixed (0°) (Def) Range: full range (deg) |
| Output: IC volume | Volume or rate as defined by Stop Condition |
| Output: EC volume | Volume or rate as defined by Stop Condition |
| Output: Remaining time of step | Countdown in minutes or manual stop as defined by Stop Condition |

Protocol 8: Continuous Add with Active Removal Example

In an embodiment, this protocol uses a relatively low flow rate to continuously add to the IC and/or EC loops. Excess IC fluid is removed using EC waste through the membrane 116.

The protocol includes:

1) IC media is added through valve 250 and pump 254 to the IC circuit. Alternatively, other media could be provided continuously such as cell inlet, reagent, wash solution or EC media. If the addition of media or fluid is only for the EC side, there may be no input of fluid through the IC side.
2) Optionally or alternatively media may be added from an EC source to the EC side if only EC addition is desired. The addition may be EC media through valve 276 and pump 278. Alternatively there may be no EC input as the addition is only to the EC side. Reagent, IC media, or wash solution could also be added to the EC side.
3) On the IC side the IC inlet rate of pump 254 is 0.1 mL/min for low flow rate addition. This is selected from a range of 0 to 10 mL/min.
4) For IC addition the IC circulation rate is the maximum of $Q_{ICCM}$ or $10 \times Q_{ICA}$ with $Q_{ICCM}$ being the rate of the IC circulation pump 212 to keep the IC loop well mixed and $Q_{ICA}$ being the rate of the inlet pump 254 in mL/min selected from a range from −100 to 100 mL/min. For example it may be 20 mL/min.
5) If the low flow addition is to the EC side the EC inlet rate may be selected to be 0.1 mL/min from a range of 0 to 20 mL/min.
6) For the EC addition the EC circulation rate is selected to be $Q_{ECCM}$ which is the rate of the circulation pump 228 in mL/min selected from a potential range of 0 to 100 mL/min, for example 30 mL/min.
7) The outlet in this example is EC waste.
8) The rocker control for the bioreactor 100 is off with no rotation.
9) The stop condition for the protocol is manually though it alternatively may be based on the time (for example 0.1 to 1440 minutes) or IC or EC volumes (for example IC or EC volumes may be from 1 to 4000 mL).

The brief summary of this protocol is set forth below.

Protocol 8 Continuous Add with Active Removal

Purpose of protocol: Continually adds a low flow rate to the IC and/or EC loops. A pump is used to remove excess IC fluid.

Step 1:

| | Input Range |
|---|---|
| IC Source | Cell Inlet |
| | Reagent |
| | IC Media (Default) |
| | Wash |
| | EC Media |
| | None |
| EC Source | Reagent |
| | IC Media |
| | Wash |
| | EC Media (Default) |
| | None |
| Stop Condition | Time |
| | Manual Stop (Default) |
| | IC volume: |
| | EC volume: |
| IC Inlet Rate (ml/min) | Default: 0.1 |
| | Range: 0 to 10 mL/min |
| IC Circulation Rate (ml/min) | Default: Maximum of ($Q_{ICCM}$, 10 × $Q_{ICA}$) |
| | Range: −100 to 100 mL/min |
| EC Inlet Rate (ml/min) | Default: 0.1 |
| | Range: 0 to 20 mL/min |
| EC Circulation Rate (ml/min) | Default: $Q_{ECCM}$ |
| | Range: 0 to 100 mL/min |
| Distribution Rate (ml/min) | Default: = (—) $Q_{ICA}$ |
| Outlet | EC Waste (Default) |
| Rocker Control | On |
| | Off (Default) |
| | fixed |
| Output: IC volume | Volume or rate as defined by Stop Condition |
| Output: EC volume | Volume or rate as defined by Stop Condition |
| Output: Remaining time of step | Countdown in minutes or manual stop as defined by Stop Condition |

Protocol 9: Reagent Add Example

In an embodiment, this protocol loads reagent from reagent bag 244 through valve 248 by pump 254 into the IC side until the bag is empty. The IC waste valve 290 is closed for circulation through circulation loop 202. The cell inlet bag 262 includes at $V_{FTO}$ of air which is defined as $(1+LP\%/100)*V_{ICBL}+5$ mL, for example 38 ml. LP % is about a 20% pump error. $V_{ICBL}$ is the volume from bag 244 to IC loop. The cell inlet bag has at least 10 mL of fluid.

The protocol includes:
1) Introduction of reagent through valve 248 by pump 254 to the IC loop 202.
2) Introduction of air, as pump 254 continues, from cell inlet bag 262.
3) Nothing is introduced on the EC side.
4) The IC inlet rate from pump 254 is 10 mL/min selected from a range of 0 to 100 mL/min
5) The IC circulation rate from pump 212 is the maximum of the IC circulation pump rate 212 to keep the IC loop 202 well mixed or a value selected from the minimum of 300 or $10 \times Q_{ICA}$ (IC inlet pump 254 rate), for example, 100 mL/min
6) There is no EC inlet but the circulation rate is the rate of the circulation pump 228 to keep the EC loop well mixed, for example 30 mL/min.
7) The outlet is EC waste through valve 292. IC waste through valve 290 is an option.
8) The rocker control for the bioreactor 100 is fixed or stationary. Alternatively, the rocker control range of motion is from −90° to 180° with 1 second pauses at the end of the motion range.
9) The stop for the reagent load is when air reaches the lower sensor 1264 of the air removal chamber or ARC.

10) After air detection the ARC is filled to the upper sensor 1268 from the IC media or a bag such as wash solution or EC media bag that did not contain reagent. Valve 260 and vent are open to purge ARC air.
11) Media such as IC media through valve 250 and moved by pump 254 continues to chase any reagent from the ARC to the IC loop 202.
12) The stop condition for the chase of reagent is the IC volume $(V_{ARCA}+V_{ARCBS})*2$.

$V_{ARCA}$ is the volume from the bottom sensor of the ARC to point A on FIG. 2.

$V_{ARCBs}$ is the volume of the ARC between top and bottom sensors. For example, the IC volume may be 22 mL. The range for this volume is between 0 to 100 mL.

The brief summary of this protocol is set forth below.

Protocol 9 Reagent Add

Purpose of protocol: Loads reagent from the reagent bag into the IC loop until the bag is empty. The IC waste valve is closed during this protocol.

Step 1: Load Reagent

Purpose of Step: Loads reagent into the system.

Precondition: Need at least $V_{FTO}$ of air in cell inlet bag.

| | Input Range |
|---|---|
| IC Source | Cell Inlet |
| | Reagent (Default) |
| EC Source | None |
| Stop Condition | ARC Stop |
| IC Inlet Rate (ml/min) | Default: 10 |
| | Range: 0 to 100 mL/min |
| IC Circulation Rate (ml/min) | Default: Maximum of ($Q_{ICCM}$, min(300, 10 × $Q_{ICA}$)) |
| | Range: −300 to 300 mL/min |
| EC Inlet Rate (ml/min) | Default: 0 |
| EC Circulation Rate (ml/min) | Default: $Q_{ECCM}$ |
| | Range: 0 to 300 mL/min |
| Outlet | EC Waste (default) |
| | IC Waste |
| Rocker Control | On (−90°, 180°, 1 sec) |
| | Range: full range (deg, time) |
| | Fixed (0°) (Default) |
| | Range: full range (deg) |
| Output: IC volume | rate as defined by Stop Condition |
| Output: EC volume | N/A |
| Output: Remaining time of step | ARC Stop as defined by Stop Condition |

Step 2: ARC Chase Purpose of Step: Chases reagent from the ARC into the IC Loop.

| | Input Range |
|---|---|
| IC Source | IC Media (Default) |
| | Wash |
| | EC Media |
| | Note: user cannot choose same bag used in step 1 because that bag is now empty |
| EC Source | None |
| Stop Condition | IC volume: $(V_{ARCA} + V_{ARCBS}) * 2$ Range: 1 to 100 mL |
| IC Inlet Rate (ml/min) | Default: Same as Step 1 |
| IC Circulation) Rate (ml/min) | Default: Same as Step 1 |
| EC Inlet Rate (ml/min) | Default: same as Step 1 |
| EC Circulation Rate (ml/min) | Same as Step 1 |
| Outlet | Same as step 1 |
| Rocker | Same as Step 1 |
| Output: IC volume | Volume as defined by Stop Condition |

| Input Range | |
|---|---|
| Output: EC volume | Volume as defined by Stop Condition |
| Output: Remaining time of step | Countdown in minutes as defined by Stop Condition |

Protocol 10: Bolus Add Example

In an embodiment, this protocol adds a selected volume of reagent into the IC loop. A bolus into the EC loop can also optionally be added. If the IC waste (valve 290) is closed ultrafiltration through the membrane 116 to the EC side will occur.

The protocol includes:
1) Reagent as the IC source is introduced through the pump 254. Alternatively other sources of media or wash could be used for a bolus amount.
2) No EC source. However, if bolus amount is to EC side only there would be no IC source and bolus amount would be introduced by pump 278.
3) For IC bolus, inlet would be 10 mL/min selected from a range up to the rate of the inlet pump.
4) The IC circulation rate is the maximum of $Q_{ICCM}$ as compared to the minimum of 300 or $10 \times Q_{ICA}$ as described above with respect to the Reagent Add protocol. This is selected from the range of −300 to 300 mL/min. In this example it may be 100 mL/min.
5) If the bolus is to the EC side there is no IC inlet or source.
6) The EC circulation is $Q_{ECCM}$ or the rate of the circulation pump 228 to keep the EC loop 204 well mixed. In this example it may be 30 mL/min.
7) The outlet is EC waste through valve 292. Alternatively it could be to harvest through valve 298 or to IC waste through valve 290.
8) The rocker control is off or alternatively could be set for rotation as described previously.
9) The stop condition can be selected to be based on time up to 20 minutes or an IC volume selected to be 10 mL in a range up to 200 mL.

The Bolus Add protocol is summarized below.

Protocol 10 Bolus Add

Purpose of protocol: Quickly adds a selected volume of reagent into the IC loop; you can add an EC bolus at the same time. During the default condition the IC waste valve closed, which forces ultrafiltration.

Step 1: Bolus Add

| Input Range | |
|---|---|
| IC Source | Reagent (Default) |
| | IC Media |
| | Wash |
| | EC Media |
| | None |
| EC Source | Reagent |
| | IC Media |
| | Wash |
| | EC Media |
| | None (Default) |
| Stop Condition | Time (1 min) Range: 0.1 to 20 min |
| | IC volume: 10 (Default) Range: 1 to 200 mL |
| | EC volume: (15 mL) Range: 1 to 300 mL |
| IC Inlet Rate (ml/min) | Default: 10 |
| | Range: 0 to $Q_{ARC}$ mL/min |
| IC Circulation Rate (ml/min) | Default: Maximum of ($Q_{ICCM}$, min(300, 10 × $Q_{ICA}$)) |
| | Range: −300 to 300 mL/min |
| EC Inlet Rate (ml/min) | Default: 0 |
| | Range: 0 to 300 mL/min |
| EC Circulation Rate (ml/min) | Default: $Q_{ECCM}$ |
| | Range: 0 to 300 mL/min |
| Outlet | EC Waste (default) |
| | IC Waste |
| | Harvest |
| Rocker | On (−90°, 180°, 1 sec) Range: full range (deg, time) |
| | Fixed (0°) (Default) Range: full range (deg) |
| Output: IC volume | Volume as defined by Stop Condition |
| Output: EC volume | Volume as defined by Stop Condition |
| Output: Remaining time of step | Countdown in minutes as defined by Stop Condition |

Protocol 11: Harvest Cells Example

In an embodiment, the protocol relates to transferring cells once they are in suspension from the IC loop. Additional protocols described below relate to releasing the cells from the membrane 116 in the bioreactor to place them in suspension prior to harvest.

The protocol includes as follows:
1) Media is inputted from an IC source such as IC media through valve 250 and pump 254. Alternatively reagent, wash solution or EC media could be the IC source. The media may be harvest media. As the cells are non-adherent and have been reloaded from the membrane, no tryspin is recirculated after release from the membrane.
2) Similarly EC media is provided through valve 276 and pump 278. Wash solution, reagent or IC media could also be introduced.
3) The IC inlet rate is 400 mL/min selected from a range from 100 to 500 mL.
4) The IC circulation rate is −AB %*$Q_{ICA}$ with AB % is $V_{AB}$*100/$V_{ICL}$. $V_{AB}$ is the volume from point A to point B on FIG. 2 and $V_{ICL}$ is the volume of the IC loop 202. $Q_{ICA}$ is the pump rate of the inlet pump 254. In this example it is 69 mL/min.
5) The EC inlet rate is $UFR_{400}$ or the negative ultrafiltration rate required to have zero transmembrane pressure at the bioreactor outlet in co-current flow and IC inlet rate=400 mL/min and EC waste valve 292 is closed. The upper range is 100 mL/min and in this example it is 60 mL/min.
6) The EC circulation rate is $Q_{ECCM}$ as described previously in a range up to 300 mL/min, for example 30 mL/min.
7) The outlet for the suspended cells is the harvest bag which receives the IC outlet.
8) The rocker control for bioreactor rotation is from −90° to 180° with 1 second pauses at the end position.
9) The stop condition for the protocol is IC volume $2 \times V_{ICL}$, for example 378 mL.

The brief summary of the Harvest Cell protocol is as follows.

Protocol 11 Harvest Cells

Purpose of protocol: Transfers cells in suspension from the IC loop, including cells in the bioreactor, to the harvest bag.

Step 1: Harvest Cells
Purpose of Step: Same as above

| | Input Range |
|---|---|
| IC Source | Reagent |
| | IC Media (Default) |
| | Wash |
| | EC Media |
| EC Source | Reagent |
| | IC Media |
| | Wash |
| | EC Media (Default) |
| Stop Condition | IC volume: 2 × $V_{ICL}$ (Default) Range: 50 to 1000 mL |
| IC Inlet Rate (ml/min) | Default: 400 |
| | Range: 100 to 500 mL/min |
| IC Circulation Rate (ml/min) | Value = −AB % * $Q_{ICA}$ |
| | Range: −AB % * $Q_{ICA}$ Minimum to −AB % * $Q_{ICA}$ Maximum |
| | Note: $Q_{ICA}$ Minimum and $Q_{ICA}$ Maximum values refer to the IC Inlet Rate (ml/min) Range. |
| EC Inlet Rate (ml/min) | Default: $UFR_{400}$ |
| | Range: 0 to 100 mL/min |
| EC Circulation Rate (ml/min) | Default: $Q_{ECCM}$ |
| | Range: 0 to 300 mL/min |
| Outlet | Harvest |
| Rocker Control | On (−90°, 180°, 1 sec.) (def) Range: full range (deg, time) |
| Output: IC volume | Volume |
| Output: EC volume | N/A |
| Output: Remaining time of step | Countdown in minutes or manual stop as defined by Stop Condition |

Protocol 12: Release Adherent Cells Example

In an embodiment, this protocol may be executed and followed prior to the Harvest Cell protocol.

The first part of the protocol may include a change of IC/EC media. For example, a media such as PBS may be used to remove protein, calcium or magnesium form the suspension.

The second part of the protocol relates to the addition of a reagent such as trypsin to release the cells from the membrane 116. This is followed by a chase to the IC loop as well as mixing the reagent in the IC loop.

The protocol includes as follows:

1) Addition of wash solution through valve 270, 212 and pump 254 to IC side. Reagent solution, EC media or IC media are optional alternatives if they contain a solution such as PBS. In this example, 1370 mL of PBS was used.
2) If the cells are on the EC side the alternative would be for EC introduction of PBS.
3) The IC inlet rate is $Q_{ECA}$ (number of IC Exc*$V_{ICE}$/(number of EC Exc*$V_{ECE}$). $V_{ICE}$ is the IC exchange volume $V_{ICL}+V_{ICBL}$. $V_{ECE}$ is the EC exchange volume $V_{ECL}+V_{ECBL}$.

4) The IC circulation rate is −AB %*$Q_{ICA}$ as described in the definitions which in this example is −17 mL/min.
5) The EC inlet rate is the lesser of $Q_{100}$ or $Q_{MAX}$ where $Q_{100}$=100 (number of EC Exc*$V_{ECE}$) (number of IC Exc.*$V_{ICE}$) and $Q_{MAX}$=300. In this example the EC inlet rate is 148 mL/min.
6) The EC circulation rate is −CD %*$Q_{ECA}$ as defined in the definitions.
7) The outlet can be IC waste or EC waste or both through valves 290 or 292.
8) The rocker control for bioreactor 100 is −90°, 180° with 1 second pause at the end of the range of motion, or alternatively fixed.
9) The stop condition for the wash is the number of IC and EC exchanges, in this example 2.5 each.
10) The wash is followed by the reagent introduction such as tryspin to release the cells. This is from the reagent bag 244 through valve 248 and pump 254. At least a volume $V_{FTO}$ is needed in the bag.
11) The IC inlet is 50 mL/min.
12) The IC circulation is 300 mL/min
13) There is no EC inlet but circulation is $Q_{ECCM}$ or rate to keep EC loop mixed.
14) The rocker control is on as described above with chase.
15) The stop condition is the ARC stop or when the lower sensor 1264 detects air.
16) After air detection the ARC is filled with wash or alternatively IC or EC media to upper sensor 1268.
17) Mixing of the reagent continues in the IC loop for 4 minutes.

The protocol summary is as set forth below.

Protocol Release Adherent Cells

Purpose of protocol: Releases cells from the membrane, leaving the cells in the IC Loop.

Step 1: Purpose of Step: Performs Protocol IC/EC Washout in preparation for adding reagent. For example, the system replaces IC/EC media with PBS to remove protein, $Ca^{++}$, and $Mg^{++}$ in preparation for adding trypsin.

| | Input Range |
|---|---|
| IC Source | Reagent |
| | IC Media |
| | Wash (Default) |
| | EC Media |
| EC Source | Reagent |
| | IC Media |
| | Wash (Default) |
| | EC Media |
| Stop Condition | # of IC Exchanges: 2.5 (default) range: 0.5-5.0 |
| | # of EC Exchanges: 2.5 (default) range: 0.5-5.0 |
| IC Inlet Rate (ml/min) | Value: $Q_{ECA}$ (# of IC Exc. * $V_{ICE}$)/(# of EC Exc. * $V_{ECE}$) |
| IC Circulation Rate (ml/min) | Value: −AB % * $Q_{ICA}$ |
| EC Inlet Rate (ml/min) | Initial value: the lesser of $Q_{100}$ or $Q_{max}$; where $Q_{100}$ = 100 (# of EC Exc. * $V_{ECE}$)/(# of IC Exc. * $V_{ICE}$) and $Q_{max}$ = 300. |
| EC Circulation Rate (ml/min) | Value: −CD % * $Q_{ECA}$ |
| Outlet | IC Waste |
| | EC Waste |
| | IC&EC Waste (default) |
| Rocker | On (−90°, 180°, 1 sec) Range: full range (def) (deg, time) |
| | Fixed (0°) Range: full range (deg) |
| Output: IC volume | Volume as defined by Stop Condition |
| Output: EC volume | Volume as defined by Stop Condition |
| Output: Remaining time of step | Countdown in minutes as defined by Stop Condition |

Parameters to be tested:

Check for any updates from Protocol IC/EC Washout.

Step 2: Load Reagent

Purpose of Step: Loads reagent into the system until the bag is empty.

Precondition: Need at least $V_{FTO}$ of air in bag containing the reagent.

|  | Input Range |
| --- | --- |
| IC Source | Cell Inlet Reagent (Default) |
| EC Source | None |
| Stop Condition | ARC Stop |
| IC Inlet Rate (ml/min) | Default: 50 Range: 20 to 100 mL/min |
| IC Circulation Rate (ml/min) | Default: 300 Range: 30 to 300 mL/min |
| EC Inlet Rate (ml/min) | Default: 0 |
| EC Circulation Rate (ml/min) | Default: $Q_{ECCM}$ Range: 0 to 300 mL/min |
| Outlet | EC Waste |
| Rocker Control | On (−90°, 180°, 1 sec) (def) Range: full range (deg, time) |
| Output: IC volume | Volume as defined by Stop Condition |
| Output: EC volume | N/A |
| Output: Remaining time of step | ARC Stop as defined by Stop Condition |

Step 3: ARC Chase
Purpose of Step: Chases the reagent into the IC Loop.

|  | Input Range |
| --- | --- |
| IC Source | IC Media Wash (Default) EC Media |
| EC Source | None |
| Stop Condition | IC volume: $(V_{ARCA} + V_{ARCBS}) * 2$ Range: 1 to 100 mL |
| IC Inlet Rate (ml/min) | Default: Same as Step 2 |
| IC Circulation Rate (ml/min) | Default: Same as Step 2 |
| EC Inlet Rate (ml/min) | Default: 0 |
| EC Circulation Rate (ml/min) | Default: Same as Step 2 |
| Outlet | EC Waste |
| Rocker Control | Same as Step 2 |
| Output: IC volume | Volume as defined by Stop Condition |
| Output: EC volume | N/A |
| Output: Remaining time of step | Countdown in minutes as defined by Stop Condition |

Step 4: Mix
Purpose of Step: Mixes the reagent within the IC Loop.

|  | Input Range |
| --- | --- |
| IC Source | None |
| EC Source | None |
| Stop Condition | Time: 4 minutes (default) Range: 0.1 to 20 minutes |
| IC Inlet Rate (ml/min) | Default: 0 |
| IC Circulation Rate (ml/min) | Same as step 2 (default) Range: 30 to 300 mL/min |
| EC Inlet Rate (ml/min) | Default: 0 |
| EC Circulation Rate (ml/min) | Same as step 2 (default) Range: 0 to 300 mL/min |
| Outlet | EC Waste |
| Rocker Control | Same as step 2 |
| Output: IC volume | N/A |
| Output: EC volume | N/A |
| Output: Remaining time of step | Countdown in minutes as defined by Stop Condition |

Protocol 13: Condition Media

In an embodiment, this protocol oxygenates the EC media before the addition of cells to the IC side of the bioreactor 100. The initial steps of the protocol include:
1) The EC source is generally EC media without protein introduced through valve 276 by pump 278.
2) IC circulation is enough to prevent air introduction through the hollow fibers or $Q_{ICCM}$. In this example, it is 20 mL/min.
3) The EC inlet rate is 0.1 mL/min.
4) The EC circulation rate is $Q_{ECCE}$ or the pump rate to equilibrate the EC loop. In this example it is 25 mL/min.
5) The outlet is EC waste through valve 292.
6) The rocker control is fixed with no rotation.
7) The stop for the high circulation rate conditioning is based on time from a range of 6 to 15 minutes.
8) A maintenance protocol is part of the condition media protocol.
9) The conditions for maintenance are the same as that outlined above, except that the EC circulation is reduced to $Q_{ECCM}$ which is the rate of the circulation pump to keep the EC loop mixed, for example 30 mL/min. Also, the stop for maintenance is a manual operator controlled stop. The maintenance is maintained until the operator desires cell load.

The summary of the protocol is as follows.
Protocol Condition Media
Purpose of protocol: Oxygenates the media to proper concentrations before loading the cells.
Step 1:
Purpose of Step: Accelerates the conditioning of the media using a high EC circulation rate.

|  | Input Range |
| --- | --- |
| IC Source | None |
| EC Source | Reagent IC Media Wash EC Media (Default) |
| Stop Condition | Time: $T_{CM}$ Range: 6 to 15 minutes |
| IC Inlet Rate (ml/min) | Default: 0 |
| IC Circulation Rate (ml/min) | Default: $Q_{ICCE}$ |
| EC Inlet Rate (ml/min) | Default: 0.1 |
| EC Circulation Rate (ml/min) | Default: $Q_{ECCE}$ |
| Outlet | EC Waste |
| Rocker | Fixed (0°) Range: full range (deg) |
| Output: IC volume | N/A |
| Output: EC volume | N/A |
| Output: Remaining time of step | Countdown in minutes |

Step 2: Circulate
Purpose of Step: Maintains the system in a proper state until the operator is ready to load the cells.

|  | Input Range |
| --- | --- |
| IC Source | None |
| EC Source | Same as step 1 |
| Stop Condition | Manual Stop |
| IC Inlet Rate (ml/min) | Default: 0 |
| IC Circulation Rate (ml/min) | Same as step 1 |
| EC Inlet Rate (ml/min) | Same as step 1 |
| EC Circulation Rate (ml/min) | Default: $Q_{ECCM}$ Range: 0 to 100 mL/min |
| Outlet | EC Waste |
| Rocker Control | Fixed (0°) Range: full range (deg) |
| Output: IC volume | Rate as defined by stop condition |
| Output: EC volume | Rate as defined by stop condition |
| Output: Remaining time of step | manual stop as defined by stop condition |

Protocol 14: Coating Bioreactor Example

In an embodiment, this protocol is directed to coating the IC side of the bioreactor with a reagent such as fibrenectin for cell attachment. Other reagents can be used. The protocol loads the reagent until the reagent bag is emptied, chases the reagent from the ARC, and circulates the reagent. In the protocol, the cell inlet bag contains $V_{FTO}$ or (1+LP %/100*$V_{ICBL}$ 5 mL) as described in the definitions, according to embodiments. In this example, it is 40.2 mL.

The protocol includes:
1) Providing reagent from reagent bag through valve 248 and pump 254 to the IC side.
2) Cell inlet bag also may be open for fluid flow through valve 264.
3) There is no EC source or inlet rate.
4) The IC inlet rate is 10 mL/min.
5) The IC circulation rate is the maximum of (20, (min (300, 10×$Q_{ICA}$)) with $Q_{ICA}$ being the inlet pump 254 rate. In this example, it is 100 mL/min.
6) EC circulation rate is $Q_{ECCM}$ as described previously as the circulation rate to keep to EC loop mixed. In this example, it is 30 mL/min
7) The outlet is EC waste through valve 292.
8) The rocker control is off. Alternatively it could rotate from −90° to 180° with 1 second pauses at the end of the range of motion.
9) The stop condition for the reagent load is detection of air by lower sensor 1264 of the ARC.
10) After reagent load stop the ARC is loaded to upper sensor 1268 and gas evacuates through outlet 1224 and valve 260.
11) The chase can be IC media, wash or EC media provided through valve 270 if wash solution and pump 254 to the IC side.
12) The stop condition for the chase portion of the protocol is IC volume ($V_{ARCA}$+$V_{ARCBS}$)*2. $V_{ARCA}$ is the volume from the bottom of the ARC to point A on FIG. 2. $V_{ARCBS}$ is the volume of the ARC between sensors.
13) For circulation of the reagent, a low flow EC media is provided on the EC side. This may be media through valve 276 or from the reagent, IC media or wash bags through pump 278.
14) The EC inlet rate during circulation is 0.1 mL/min.
15) The IC inlet rate is $Q_{ICCM}$ which is the circulation pump 212 rate to keep the IC loop well mixed.
16) The EC circulation rate is $Q_{ECCM}$ which is the EC circulation pump 228 to keep the EC loop well mixed, in this example 30 mL/min.
17) The stop condition for circulation is either time selected or a manual stop.

The protocol is summarized below.
Protocol Coat Bioreactor
Purpose of Task: Coats the bioreactor membrane with a reagent.
Step 1: Load Reagent
Purpose of Step: Loads reagent into the system.
Precondition: Need at least $V_{FTO}$ of air in the cell inlet bag.

| | Input Range |
|---|---|
| IC Source | Cell Inlet<br>Reagent (Default) |
| EC Source | None |
| Stop Condition | ARC Stop |
| IC Inlet Rate (ml/min) | Default: 10 mL/min<br>Range: 0.1 to 100 mL/min |
| IC Circulation Rate (ml/min) | Default: Maximum of (20, (min(300, 10 × $Q_{ICA}$))<br>Range: −300 to 300 mL/min |
| EC Inlet Rate (ml/min) | Default: 0 |
| EC Circulation Rate (ml/min) | Default: $Q_{ECCM}$<br>Range: 0 to 100 mL/min |
| Outlet | EC Waste |
| Rocker Control | On (−90°, 180°, 1 sec) Range: full range (deg, time)<br>Fixed (0°) (Default) Range: full range (deg) |
| Output: IC volume | Volume or Rate as defined by stop condition |
| Output: EC volume | Volume or Rate as defined by stop condition |
| Output: Remaining time of step | Countdown in minutes or manual stop as defined by stop condition |

Step 2: ARC Chase
Purpose of Step: Chases reagent from the ARC into the IC Loop.

| | Input Range |
|---|---|
| IC Source | IC Media<br>Wash (Default)<br>EC Media |
| EC Source | None |
| Stop Condition | IC volume: ($V_{ARCA}$ + $V_{ARCBS}$) * 2 Range: 1 to 100 mL |
| IC Inlet Rate (ml/min) | Default: Same as Step 1 |
| IC Circulation Rate (ml/min) | Default: Same as Step 1 |
| EC Inlet Rate (ml/min) | Default: 0 |
| EC Circulation Rate (ml/min) | Default: Same as Step 1 |
| Outlet | EC Waste |
| Rocker Control | Same as Step 1 |
| Output: IC volume | Volume as defined by stop condition |
| Output: EC volume | n/a |
| Output: Remaining time of step | Countdown in minutes or manual stop as defined by stop condition |

Step 3: Circulate
Purpose of Step: Circulates reagent in the IC Loop.

| | Input Range |
|---|---|
| IC Source | None |
| EC Source | Reagent<br>IC Media<br>Wash (Default)<br>EC Media |
| Stop Condition | Time (1 min) Range: 0.1 to 2880 minutes<br>Manual Stop (default) |
| IC Inlet Rate (ml/min) | Default: 0 |
| IC Circulation Rate (ml/min) | Default: $Q_{ICCM}$ |
| EC Inlet Rate (ml/min) | Default: 0.1 |
| EC Circulation Rate (ml/min) | Default: $Q_{ECCM}$ |
| Outlet | EC Waste |
| Rocker Control | Same as Step 1 |
| Output: IC volume | n/a |
| Output: EC volume | Rate as defined by stop condition |
| Output: Remaining time of step | Manual stop as defined by stop condition |

Protocol 15: Cell Attachment Example
In an embodiment, the purpose of this protocol is to enable adherent cells to adhere to the IC side of the membrane while allowing flow on the EC side. The cells are already in the IC side.

The protocol includes as follows:
1) Only an EC source and EC circulation is used. There is no IC source, IC inlet rate or IC circulation rate.
2) The EC inlet is EC media with options for reagent, IC media, or wash. The media flows though valve 276 as EC media, and through pump 278.
3) The EC inlet rate is low 0.1 mL/min flow.
4) The EC circulation rate $Q_{ECCM}$ as described above which in this example is 30 mL/min.
5) The outlet is the EC waste through valve 290.
6) The rocker control is fixed or stationary.
7) The stop condition is a manual stop. Alternatively the stop could be based on time or EC volume.

The brief summary of the protocol is as shown below.

Protocol Cell Attachment Purpose of protocol: Enables adherent cells to attach to the membrane while allowing flow on the EC loop. The pump flow rate to the IC loop flow is set to zero.

Step 1: Cell Attachment

| | Input Range |
|---|---|
| IC Source | None |
| EC Source | Reagent |
| | IC Media |
| | Wash |
| | EC Media (Default) |
| Stop Condition | Time: (1440 min) Range: 0.1 to 2880 minutes |
| | Manual Stop (Default) |
| | EC volume: (150 mL) Range: 1 to 4000 mL |
| IC Inlet Rate (ml/min) | Default: 0 |
| IC Circulation Rate (ml/min) | Default: 0 |
| EC Inlet Rate (ml/min) | Default: 0.1 |
| | Range: 0.1 to 10 mL/min |
| EC Circulation Rate (ml/min) | Default: $Q_{ECCM}$ |
| | Range: 0 to 100 mL/min |
| Outlet | EC Waste |
| Rocker Control | Fixed (0°) (Default) Range: 0° to 180° |
| Output: IC volume | Volume or rate as defined by Stop Condition |
| Output: EC volume | Volume or rate as defined by Stop Condition |
| Output: Remaining time of step | Countdown in minutes or manual stop as defined by Stop Condition |

Protocol 16: User-Defined Task Example

In an embodiment, this protocol allows the user to define the task. The setting options are as follows:

| Setting | Setting Options |
|---|---|
| IC Inlet | Cell |
| | Reagent |
| | IC Media |
| | Wash |
| | EC Media |
| | None |
| IC Inlet Rate | 0 to 500 mL/min |
| IC Circulation Rate | −300 to 300 mL/min |
| EC Inlet | Reagent |
| | IC Media |
| | Wash |
| | EC Media |
| | None |
| EC Circulation Rate | −300 to 300 mL/min |
| Outlet | EC Waste |
| | IC Waste |
| | Synchronization |
| Rocker Control | In Motion (−180° to 270°, 0 to 15 seconds) |
| | Stationary (−180° to 270°) |
| Stop Condition | Manual |
| | Time (0.1 to 1440 min) |
| | IC Volume (1 to 4000 mL) |
| | EC volume (1 to 4000 mL) |

Having described various protocols for use with the cell expansion system, embodiments further relate to processor-implemented methods and systems for configuring and customizing protocols, and other settings, of the cell expansion system, through the use of UIs and GUI elements. For example, a user or operator, may select a UI element or GUI element, such as a button or other control, associated with a particular setting, including a system setting, display setting, and/or protocol setting. Such selection may be made, according to embodiments, by touching a location on a touch screen or other display area of a display device. Settings associated with the selected GUI element may then be configured through the input of data, for example. In embodiments, such configurations are stored.

The system provides for further user customizations by allowing a user or operator to create one or more custom or user-defined tasks and to add steps to the custom tasks, in accordance with embodiments of the present disclosure. For example, such added steps may be selected from a list of pre-defined processes, including Wash Out Lines, Wash Out Lines Through Membrane, Wash Rapidly, Harvest Cells, Add Bolus, and Custom, in which the Custom step provides for an added step to be a custom step itself, according to embodiments. Steps may also be omitted from a task, and configured settings may be reset to the factory default settings, according to other embodiments, through the selection of an applicable GUI element.

The configurability and customization capabilities of the cell expansion system allow the system to be adapted to a user or operator's desired settings and preferences, according to embodiments of the present disclosure. Through the use of UIs, GUI elements, and process diagram views or windows for configuring and customizing settings and system components, the system provides a visual tool for the configuration and customization of the system. Such capabilities provide an efficient way to configure and customize the system and protocols used therewith.

Figure 7:
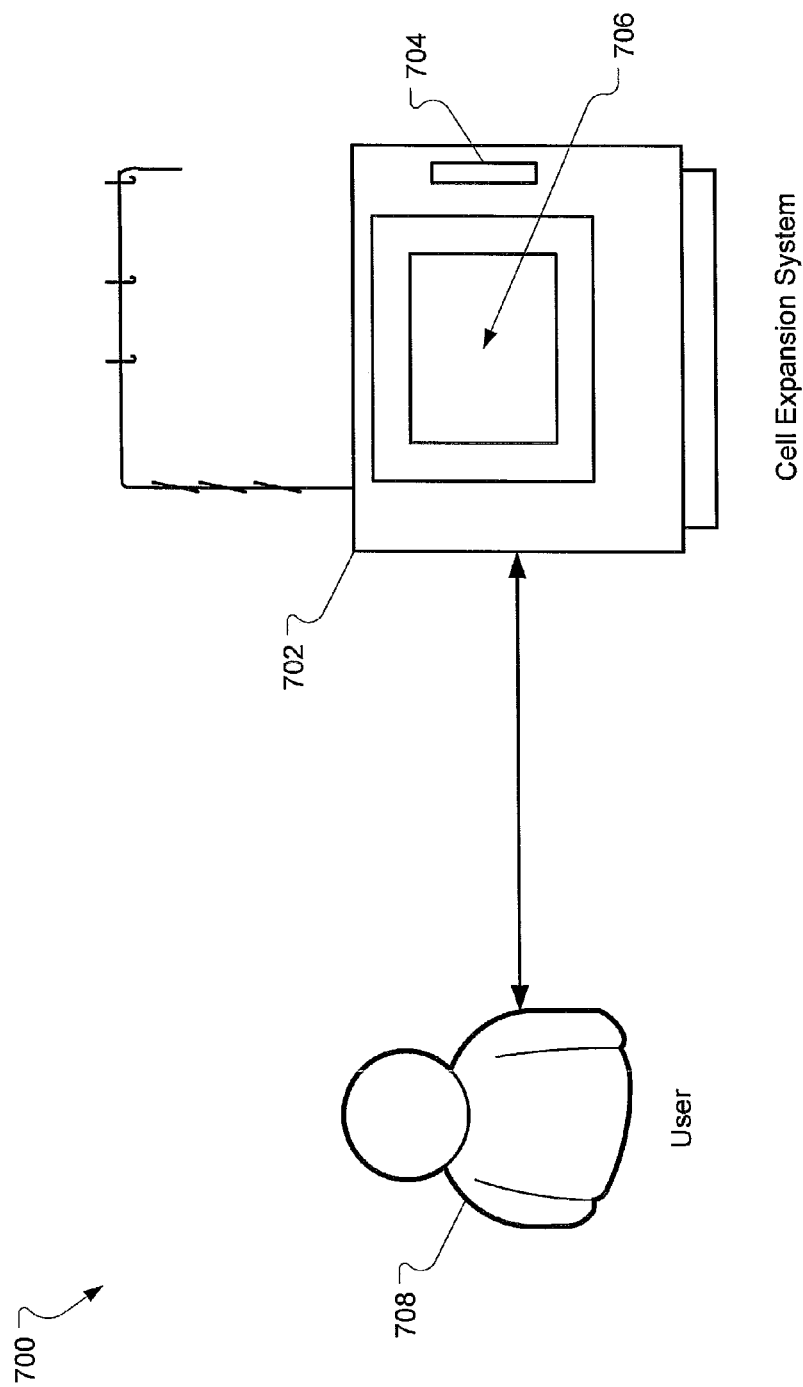
FIG. 7 illustrates an example logical representation of an environment for interacting with a UI of a cell expansion system in accordance with embodiments of the present disclosure.

Turning to FIG. 7, an example logical environment 700 for interacting with a UI of a cell expansion system is shown in accordance with embodiments disclosed herein. A cell expansion system 702 housing a fluid conveyance device accessed by opening the door of the cell expansion system with handle 704 is shown according to an embodiment. The cell expansion system 702 is capable of being interacted with by a user or operator 708, for example. The cell expansion system 702 comprises a UI 706 for displaying, and allowing interaction with, information and data related to the cell expansion system 702. In embodiments of the present disclosure, a UI, such as UI 706, for example, may be any interface for providing information to a user or operator 708 or for receiving input from a user or operator 708. A UI, such as UI 706, for example, may include application windows, rendered by a processor, such as the processor discussed with reference to FIG. 24 below, for an application, such as a configuration and/or customization application, according to embodiments.

UI 706 provides, in embodiments, for interaction by a user or operator 708, for example, with the cell expansion system 702 through the use of input devices, output devices, logical modules, e.g., software, and hardware, e.g., physical elements. UI 706 allows the user or operator 708 to operate and control the cell expansion system 702 and to view, or otherwise receive, the result(s) of such operation and control, according to embodiments herein. Such operation and control may include, for example, configuring and/or customizing settings of the cell expansion system, including protocols for use with the system. As discussed with respect to FIG. 24 below, the cell expansion system 702, including LH 706, is driven by a processor, memory, etc.

Logical environment 700 is not limited to any particular implementation but, rather, encompasses any environment upon which the functionality of environment 700 may be practiced. For example, user or operator 708 may be a single user or operator or multiple users or operators. Further, in other embodiments, cell expansion system 702 may be interacted with by another device, program, machine, etc. Logical environment 700 represents an example way of practicing embodiments disclosed herein but is not intended to limit the scope of the present disclosure. For example, logical environment 700 may be considered with respect to the specific components present, e.g., processor, or may be considered with respect to the corresponding modules.

Figure 8:
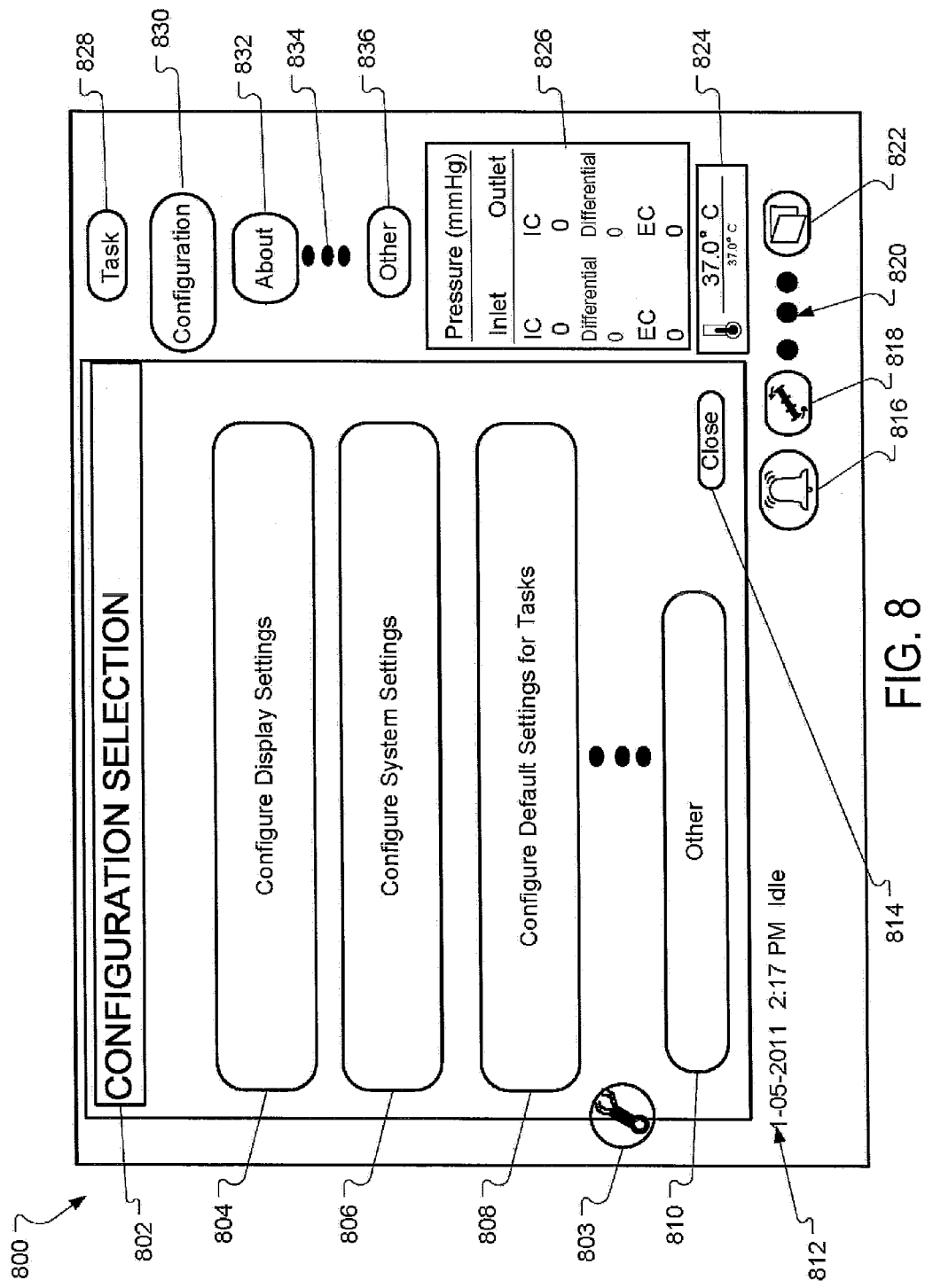
FIG. 8 depicts an example UI showing GUI elements and features for configuring the cell expansion system in accordance with embodiments of the present disclosure.

While FIG. 7 shows example environment 700 for operating, configuring, and/or customizing the cell expansion system according to embodiments, FIG. 8 illustrates an example UI 800 comprising GUI elements for making configuration selections in accordance with further embodiments of the present disclosure. UI 800 is displayed on the user interface 706 of the cell expansion system 702, for example. UI 800 may be retrieved in response to a user selecting to configure the cell expansion system, in which a screen entitled, "Configuration Selection" 802 with configure icon 803, appears to allow the user to make configuration selections. The screen name, "Configuration Selection" 802, and configure icon 803 are offered as an example for purposes of illustration. Numerous types of titles, names, headings, and/or icons may be used in accordance with embodiments without departing from the spirit and scope of the present disclosure. As shown in UI 800, GUI elements 804, 806, 808, and 810 allow a selection to be made to configure an aspect of the cell expansion system, such as of cell expansion system 702 shown in FIG. 7. For example, a selection may be made to configure display settings 804, system settings 806, default settings for tasks or protocols 808, and/or any other type of configuration aspect 810 related to the cell expansion system 702, according to embodiments. GUI elements shown in FIG. 8 may include, for example, buttons, controls, icons, boxes, radio buttons, checkboxes, menus, drop-down menus, windows, including pop-up windows, etc. In embodiments, UI 800 provides a status bar 812 including information related to the system, including the date and time and status of the system performance, such as "Idle." Further, alarm 816, rocker control 818, other controls (as shown by ellipsis 820), and door icon 822 (for indicating when the door of cell expansion system 702 is open, for example) also provide information regarding the cell expansion system, according to embodiments. Further, in an embodiment, temperature window 824 displays relevant temperatures, including, for example, the actual temperature of the air inside the incubator and the temperature set point. In addition, pressure window 826 provides the current pressure measurements at the IC and EC inlets and outlets, as well as the inlet and outlet differential pressures, according to an embodiment. Other GUI elements include a "Task" GUI element 828 for displaying the task selection screen, a "Configuration" GUI element 830 for displaying another configuration screen, and an "About" configuration GUI element 832 for displaying information regarding the cell expansion system, including, for example, identification information for the device, version information, etc., according to embodiments. In addition, other types of GUI elements may be included to assist a user to navigate the system and UIs, as shown by ellipsis 834 and the "Other" GUI element 836. Further, the "Configuration Selection" screen may be closed with selection of the "Close" GUI element 814.

Figure 9A:
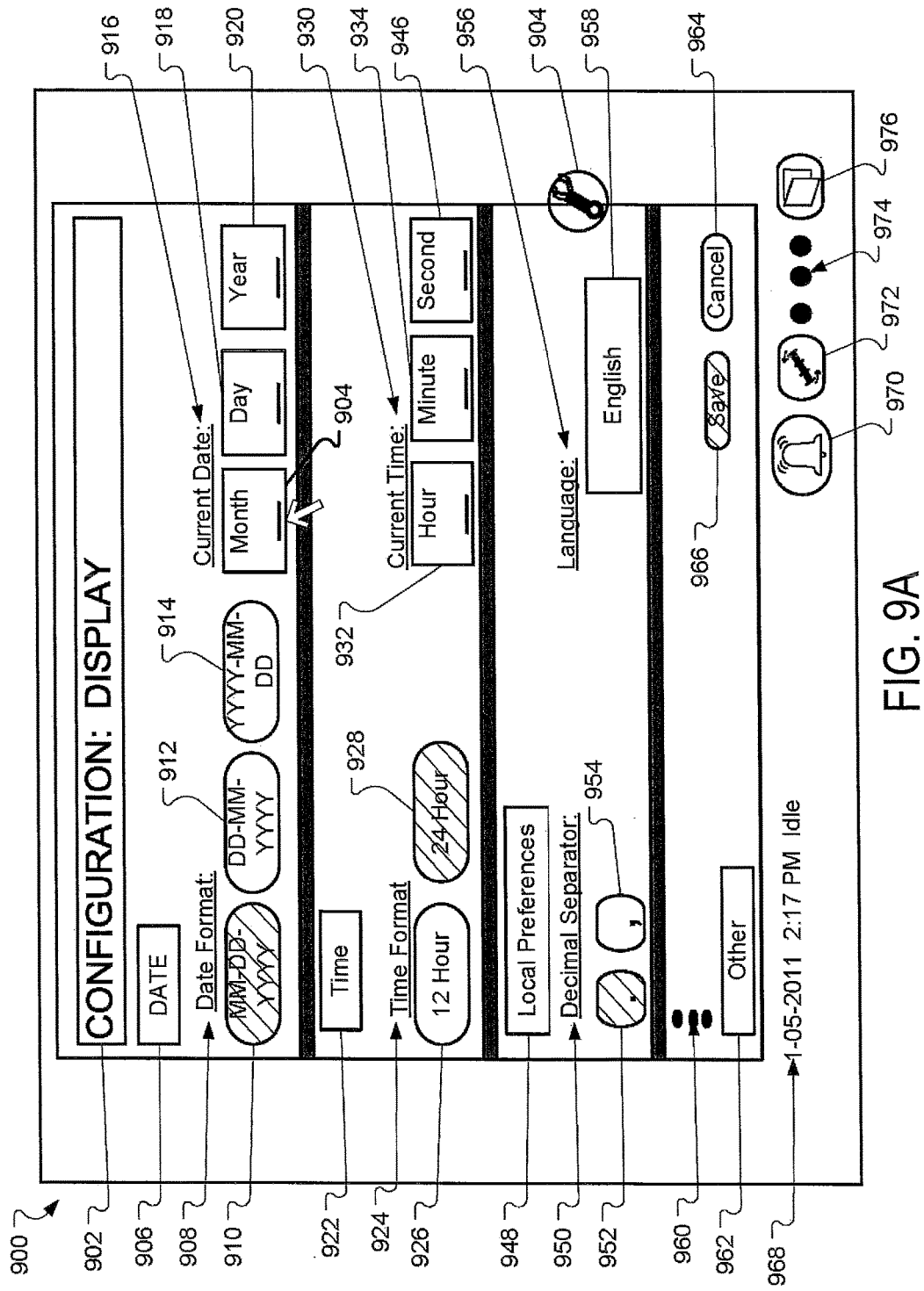
FIG. 9A illustrates an example UI showing GUI elements and features for configuring display settings of the cell expansion system in accordance with embodiments of the present disclosure.

While FIG. 8 provides configuration selection options, FIG. 9A illustrates an example UI 900 for configuring display settings of the cell expansion system, in accordance with embodiments of the present disclosure. For example, UI 900 provides for changing the format of the date display, changing the format of the time display, setting the current date and time, selecting a language for the display of text, and selecting a decimal separator type. The screen name "Configuration: Display" 902 and icon 904 indicate that the UI provides for configuring display settings. Any type of screen name and configuration icons may be used in accordance with embodiments herein. The screen name 902 and icon 904 are offered for purposes of illustration. UI 900 allows for configuration of the date 906, time 922, local preferences 948, and other 962 display settings as shown by ellipsis 960. UI 900 allows a user, for example, to select the date format 908, such as whether the date used with display settings for the system includes a "MM-DD-YYYY" 910 format, a "DD-MM-YYYY" 912 format, or a "YYYY-MM-DD" 914 format, in which "M" refers to "month," "D" refers to "day" of the month, and "Y" refers to "year." The hatching at button 910 indicates that button 910 has been selected, such as by touching this button using the touch screen of the cell expansion system, according to embodiments. The use of hatching in the Figures herein is offered for purposes of illustration only. Any type of visual indicia may be used without departing from the spirit and scope of the present disclosure. Further, a user may select to enter the current date 916, including the month 904, day 918, and year 920.

In addition, UI 900 allows for a selection of the time format 924, in which a user, for example, may select a 12 hour format 926 or a 24 hour format 928. The current time 930 may also be entered using UI 900 by providing data for the hour 932, minute 934, and second 946 fields.

Figure 9B:
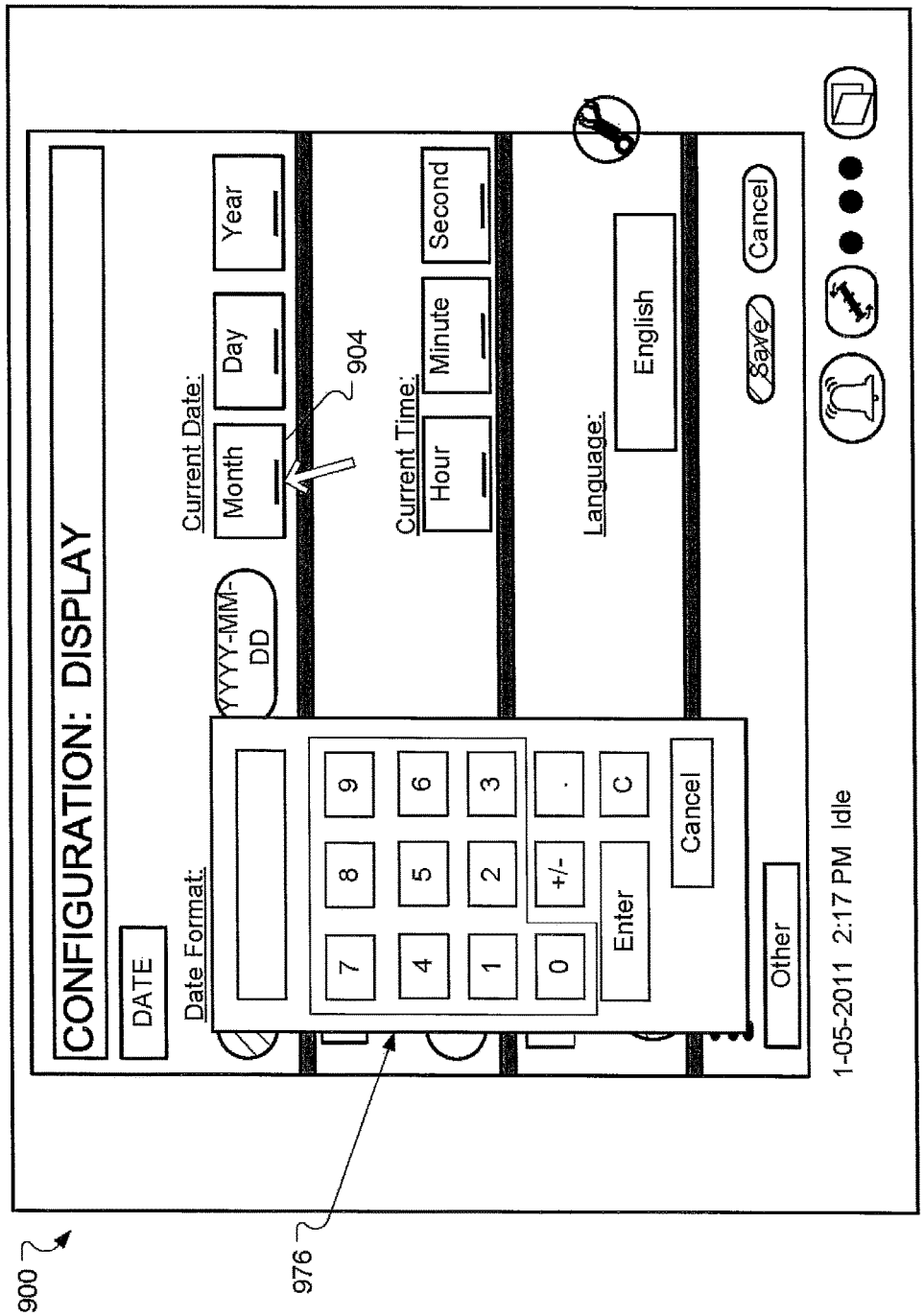
FIG. 9B depicts an example data entry window with the UI of FIG. 9A for entering data for configuring display settings of the cell expansion system in accordance with embodiments of the present disclosure.
Figure 9C:
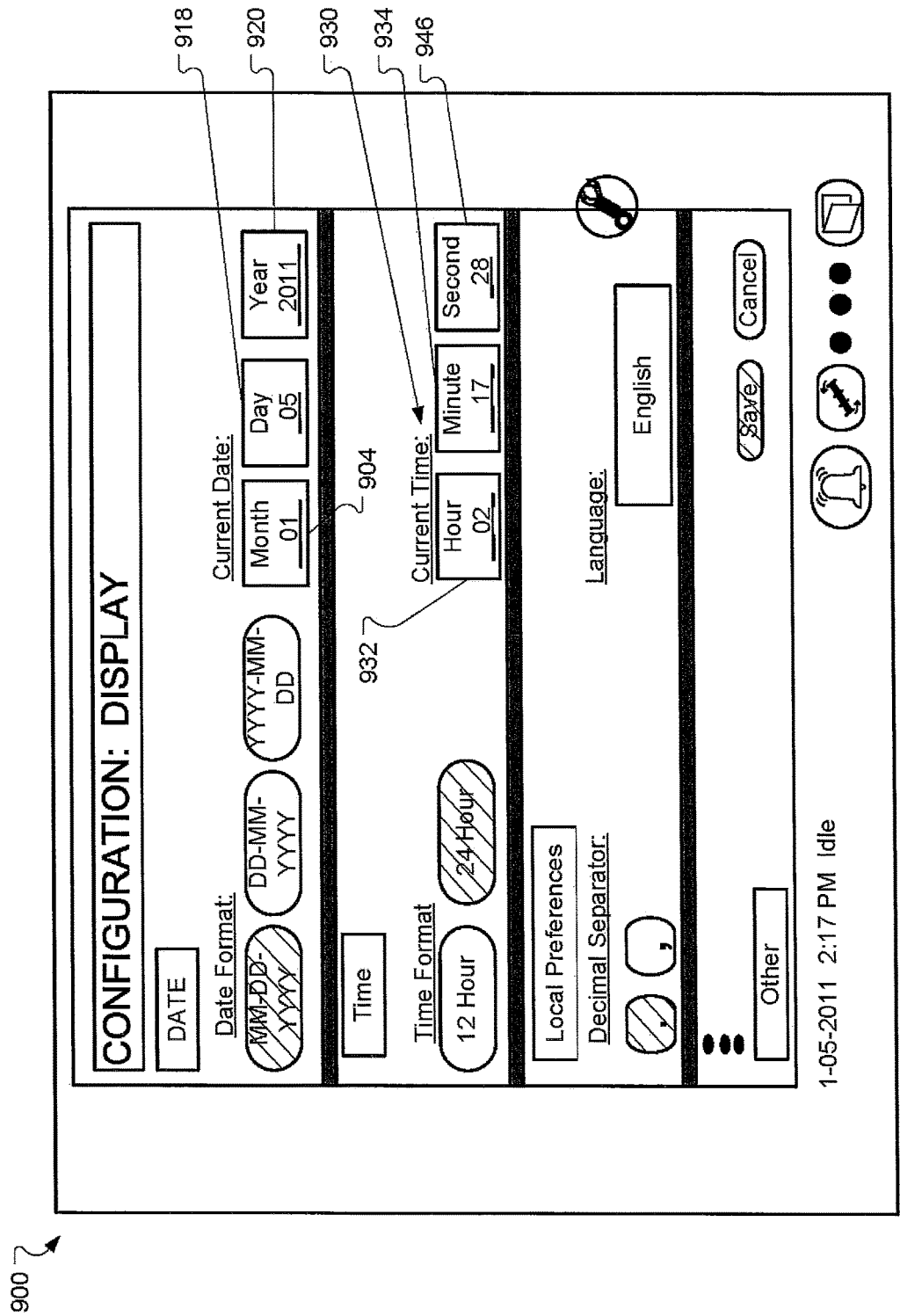
FIG. 9C illustrates an example UI showing configuration aspects for display settings of the cell expansion system in accordance with embodiments of the present disclosure.

Turning to FIG. 9B, for example, a user has selected to enter the current date for the display settings of the system, in which an arrow at 904 indicates a selection of the current date. In response to receiving the selection to configure the date, the system determines that a numeric value is associated with the current date setting. In response to such determination, the system provides a data entry pad 976 to allow for the input of one or more numeric values for entering the current date, according to embodiments. After providing numeric values through the use of the data entry pad or data entry window 976, UI 900, as shown in FIG. 9C, displays the filled-in current date 904, 918, and 920.

In addition, a selection may be made to provide or modify the current time 930, in which a data entry window or data entry pad or other means may also be provided for receiving entry of numeric values for the associated time fields 932, 934, and 946. FIG. 9C shows the results of the system receiving numeric values for the time fields 932, 934, and 946. Further, in embodiments where a 12-hour clock is used, a selection may be made, or data may be provided, for example, to designate whether the indicated time is for the "a.m." (ante meridiem) period or for the "p.m." (post meridiem) period.

Returning to FIG. 9A, UI 900 also provides for a configuration of "Local Preferences" 948, in which a selection may be made as to whether numeric values use a "period" 952 or "comma" 954 decimal separator 950. Further, the language 956 used for displaying the text used in displaying data and information using the display area of UI 706 may also be selected, according to embodiments. For example, while "English" 958 is shown as the default language, GUI element 958 may be selected, as shown by the "arrow" pointer on the "English" 958 GUI element of FIG. 9D.

Figure 9D:
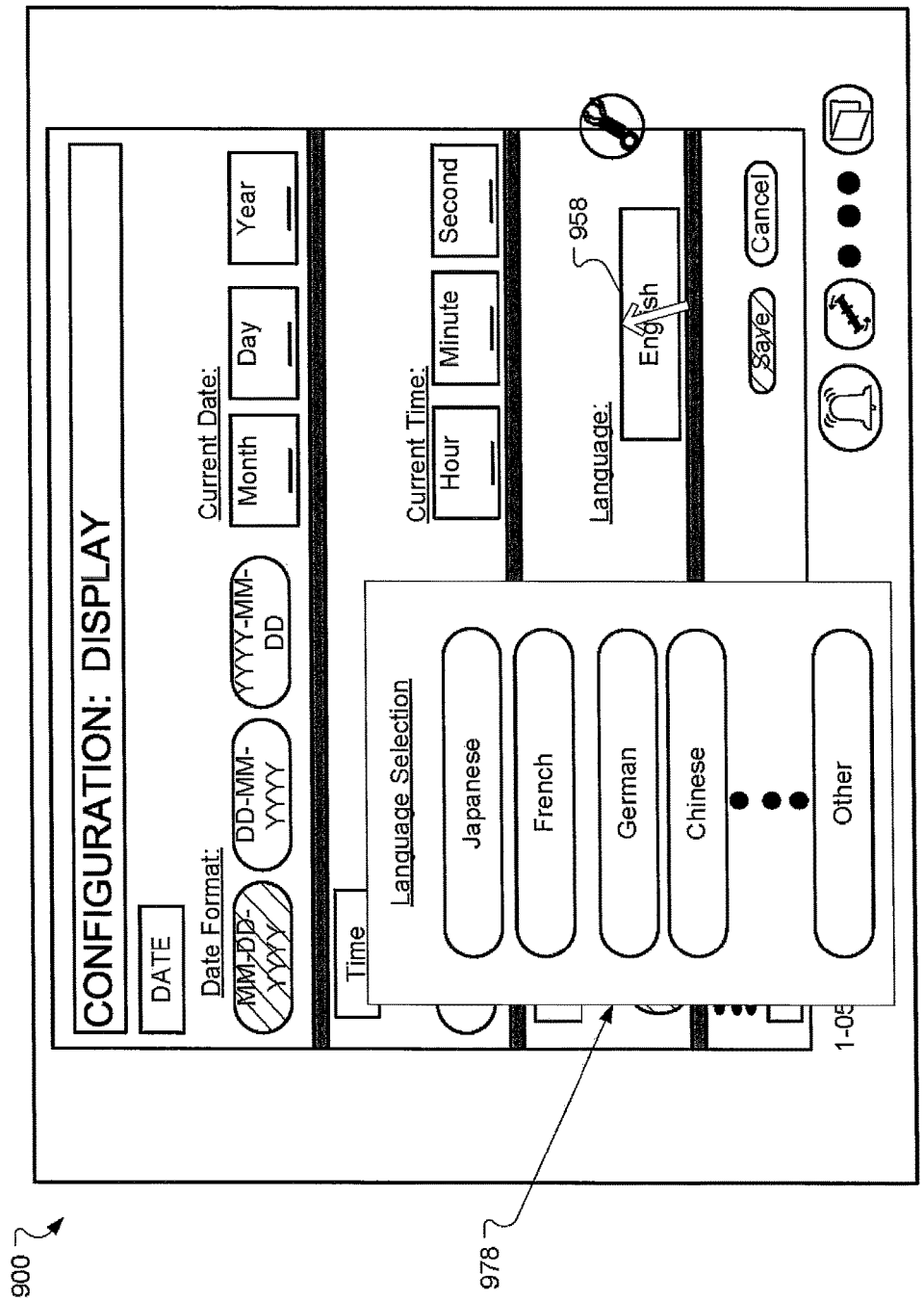
FIG. 9D depicts an example UT showing a language selection window for configuring display settings of the cell expansion system in accordance with embodiments of the present disclosure.

In response to receiving the selection, the system determines that a menu, list, or window of selection options should be provided in UI 900, as shown in FIG. 9D, according to embodiments of the present disclosure. In an embodiment, such selection options are dynamically determined. In another embodiment, such selection options are predetermined or pre-defined. The language selection window 978 displays various GUI elements for different language options. The languages listed in menu 978 are offered for purposes of illustration only. Any number and/or type of languages may be offered depending on the system characteristics in accordance with embodiments disclosed herein. Further, the language choices may be displayed in any language without departing from the spirit and scope of the present disclosure. While the language selection window 978 of FIG. 9D shows the options using English text, other embodiments provide for the language choices to each be written in their respective languages.

Returning to FIG. 9A, UI 900 provides for the configurations to be saved 966 and stored by the system, according to an embodiment, in which the system stores and applies the configured changes. In such an embodiment, the configuration screen then closes. In another embodiment, a selection may be made to "Cancel" the configuration of display settings by selecting the "Cancel" button 964, in which the Configuration: Display window closes and returns to another screen, for example. Further, UI 900 provides a status bar 968 including information related to the system, including the date and time and status of the system performance, such as "Idle." Further, alarm 970, rocker control 972, other controls (as shown by ellipsis 974), and door icon 976 (for indicating when the door of cell expansion system 702 is open, for example) also provide information regarding the cell expansion system, according to embodiments.

Figure 10A:
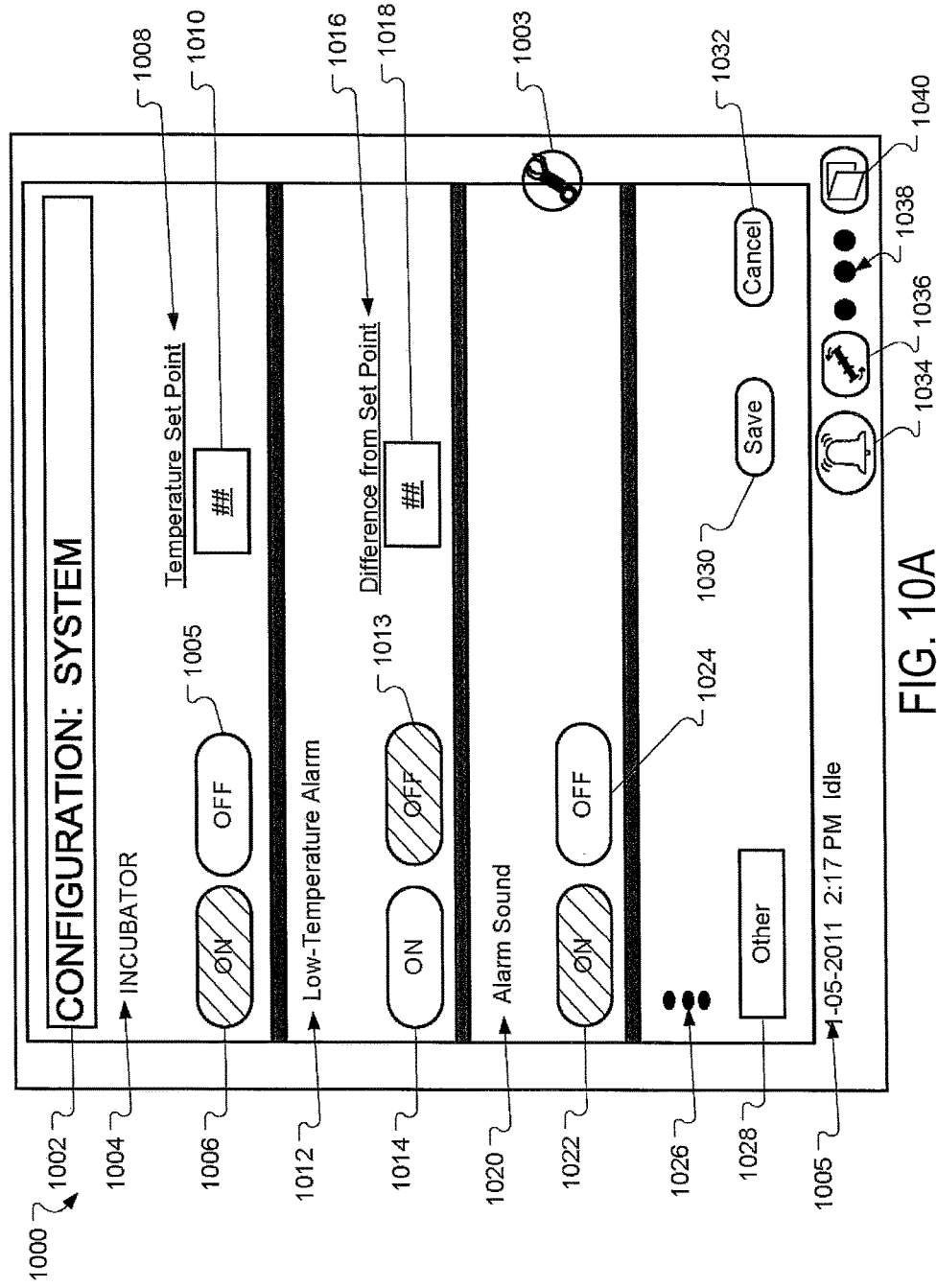
FIG. 10A illustrates an example UI providing GUI elements and features for configuring system settings of the cell expansion system in accordance with embodiments of the present disclosure.
Figure 10B:
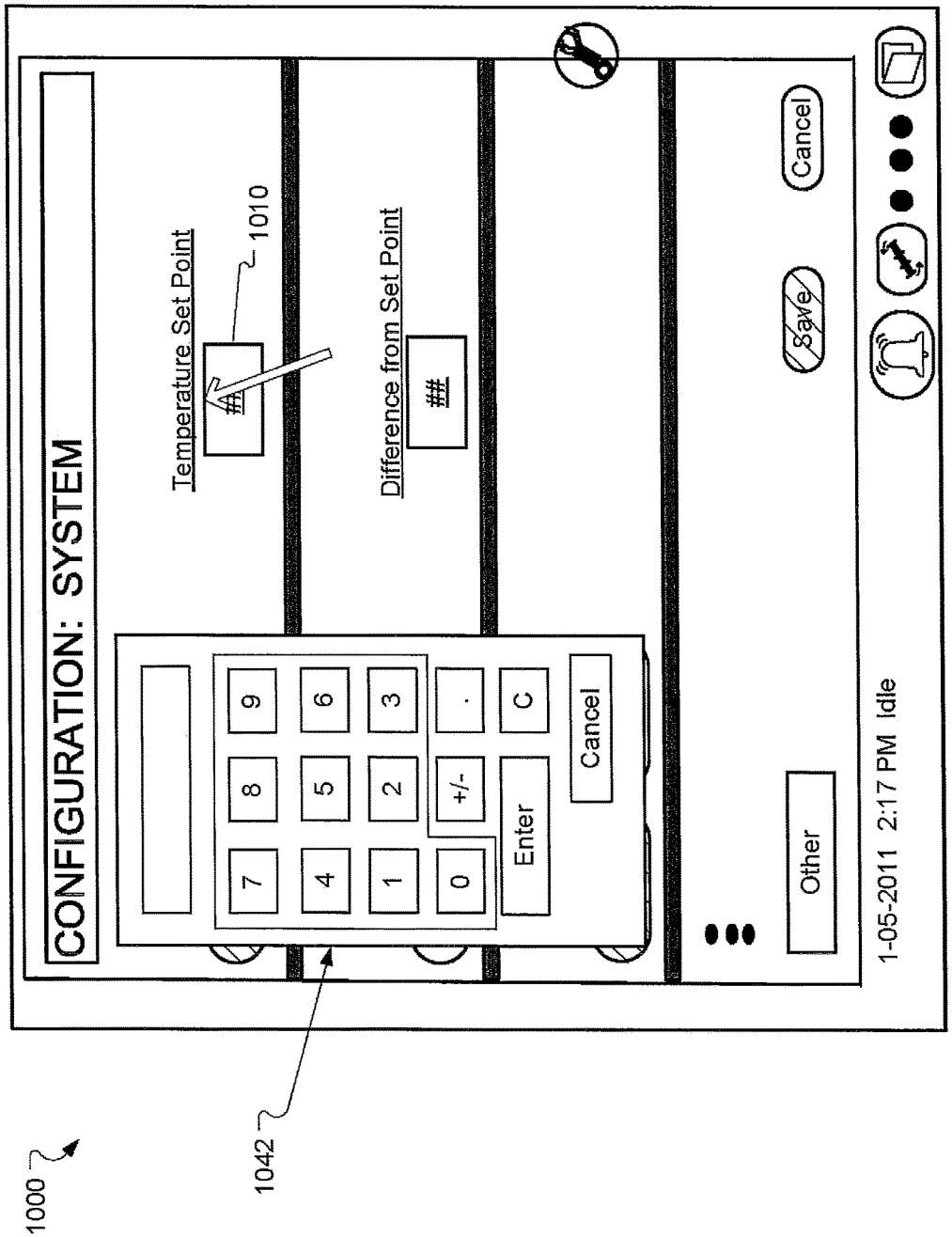
FIG. 10B depicts an example data entry window with the UI of FIG. 10A for entering data for configuring system settings of the cell expansion system in accordance with embodiments of the present disclosure.

While FIGS. 9A, 9B, 9C, and 9D illustrate UI 900 for configuring display settings, FIGS. 10A and 10B depict UI 1000 for configuring system settings, in accordance with embodiments of the present disclosure. For example, UI 1000 provides for turning the incubator on or off, changing the temperature set point of the system, turning the alarm sound on or off, setting the low-temperature alarm for the system, etc. The screen name "Configuration: System" 1002 and icon 1003 indicate that the HI provides for configuring system settings. Any type of screen name and configuration icons may be used in accordance with embodiments herein. The screen name 1002 and configure icon 1003 are offered for purposes of illustration. In configuring system settings, a selection may be made to turn the incubator 1004 "on" 1006 or "off" 1005. The temperature set point 1008 of the system may also be set 1010 by selecting GUI element 1010, in which the temperature set point is the point at which the temperature of the system incubator is set, according to an embodiment. In an embodiment, a default temperature set point is provided. However, this numeric value may be configured by selecting, or touching in an embodiment using a touch screen, the temperature set point field 1010. For example, an "arrow" pointer is shown as selecting the temperature set point field 1010 in FIG. 10B. As shown in UI 1000 of FIG. 10B, the system, in response to receiving the selection of the temperature set point field 1010, determines that a numeric value is associated with the temperature set point field 1010. After determining that a numeric value is associated with field 1010, the system provides a data entry window or data entry pad 1042 for receiving an input of data for the desired temperature set point. After receiving such data, the system updates the temperature set point field 1010, in accordance with embodiments disclosed herein.

Returning to FIG. 10A, the low-temperature alarm 1012 may be configured by turning it "on" 1014 or "off" 1013. In an embodiment, the alarm is shown as being turned "off" 1013 in FIG. 10A through the use of hatching. This selection (and others shown) are offered for purposes of illustration only. The difference from the set point 1016 may also be set by selecting field 1018. In response to receiving the selection of the difference from set point field 1018, the system determines that a numeric value is associated with the field 1018. After determining that a numeric value is associated with field 1018, the system provides a data entry window or data entry pad such as shown in FIG. 10B at data entry pad 1042, for example, for receiving an input of data for the desired difference from set point. After receiving such data, the system updates the difference from set point field 1018, in accordance with embodiments disclosed herein. Next, as shown in FIG. 10A, the system alarm sound 1020 may be turned "on" 1022 or "off" 1024 by selecting the appropriate button for such desired configuration. The selected button changes color to "black" or another designated color or visual indicia to show selection, according to embodiments. The "on" button 1022 is shown as being selected in FIG. 10A. Any type of visual indicia change may be used in accordance with embodiments of the present disclosure without departing from the spirit and scope of the present disclosure. Further, other system settings 1028 may be configured as shown by ellipsis 1026.

After making desired configurations, such changes may be saved by selecting the "Save" button 1030, in which the system responds to such selection by saving and applying the changes. The configuration screen then closes, according to embodiments. In another embodiment, a selection may be made to "Cancel" 1032 the configuration of display settings by selecting the "Cancel" button 1032, in which the Configuration: System window closes and returns to another screen. Further, UI 1000 provides a status bar 1005 including information related to the system, including the date and time and status of the system performance, such as "Idle." Further, alarm 1034, rocker control 1036, other controls (as shown by ellipsis 1038), and door icon 1040 (for indicating when the door of cell expansion system 702 is open, for example) also provide information regarding the cell expansion system, according to embodiments.

Turning to FIG. 11, UI 1100 provides for configuring a task or protocol for use with the cell expansion system, in accordance with embodiments of the present disclosure. As shown, UI 1100 appears with screen name "Configure Confirmation: Task A," for example, after the system receives a selection to configure a system task or protocol. In embodiments, "Task A" refers to a predetermined or pre-defined task, such as "Release Adherent Cells with Harvest," for example. Such selection may be initially made as shown by selecting button 808 in FIG. 8 and then selecting a particular type of predetermined or pre-defined protocol, such as "Release and Harvest," and then selecting "Release Adherent Cells with Harvest," according to an embodiment. In another embodiment, UI 1100 appears after an initial configuration of a task or protocol is made, and the system is providing a confirmation of the desired configuration. Other embodiments provide for selecting the configuration of protocols through other buttons or GUI elements, for example. The screen name, "Configure Confumation: Task A" 1102 is offered as an example for purposes of illustration. Numerous types of titles, names, headings, and/or icons may be used in accordance with embodiments of the present disclosure without departing from the spirit and scope of the present disclosure.

UI 1100 allows for the configuring of default settings for each task or protocol. When the default settings for a particular task or protocol, e.g., a first task, are configured, the system replaces the factory default settings for the task, e.g., the first task, with the settings that are configured. In embodiments, the system also stores the newly configured settings. In embodiments, each time a task, e.g., first task, is subsequently selected, the system automatically populates the settings for the first task with the configured default settings. Embodiments also allow the default settings to be reset, or restored, back to the factory default settings by selection of the "Reset" button or GUI element 1156 of FIG. 11. Selecting "Reset" 1156 restores all of the settings for a selected task back to the factory default settings for that task, according to embodiments. In embodiments, the restoration of the factory default settings is stored upon selection of the "Save" GUI element 1158.

Further, UI 1100 of FIG. 11 shows the number of steps 1112 included in the particular task or protocol listed 1102. For example, UI 1100 shows "step 1" 1114, "step 2" 1116, and other steps 1120, as shown by ellipsis 1118. Any number of steps, or a single step, may be included according to embodiments of the present disclosure. Further, other steps not shown in UI 1100 may be included, as shown by the ability to use buttons or other controls 1104, 1106, 1110, and 1111 for moving between screens displaying other steps, in embodiments. Ellipsis 1108 represents other buttons or controls which may be used for moving between screens in accordance with embodiments of the present disclosure. While not shown in FIG. 11, the title of a particular step may be displayed by the step number. For example, for the "Release Adherent Cells with Harvest" protocol, "step 1" 1114 may list "Wash Out Lines," "step 2" 1116 may list "Load Reagent," and "step 3" 1120 may list "Chase ARC," according to an embodiment of the present disclosure.

Further, one or more settings for a particular step may be configured by selecting the appropriate "Configure" GUI element, such as configure button 1148 for step 1, configure button 1150 for step 2, configure button 1154 for another step 1120, or any other number of configure buttons as shown by ellipsis 1152 for associated steps shown by ellipsis 1118. Such settings to configure include, for example, IC Inlet 1122, IC Inlet Rate 1124, IC Inlet Rate 1126, EC Inlet 1128, EC Inlet Rate 1130, EC Circulation Rate 1132, Outlet 1134, Rocker 1136, Stop Condition 1138, Estimated Fluid Needed 1140, Omit or Include Step 1142, and other settings 1146 as shown by ellipsis 1144, according to embodiments of the present disclosure. In embodiments, the "Omit or Include Step" 1142 indicates whether a particular step is included or omitted from the task. While sample data and selected options, e.g., "Wash" or "Reagent," are shown in FIG. 11 for particular settings, in which such data and selected options may represent factory default settings according to embodiments, these data and selected options are shown for purposes of illustration. The data and selected options shown in FIG. 11 are examples only.

After making desired configurations, such changes may be saved by selecting the "Save" button 1158, in which the system responds to such selection by saving and applying the changes. The configuration screen then closes, according to embodiments. In an embodiment, the configuration screen 1100 shows the changes applied to the settings (after any configurations are made) when configuration screen 1100 appears in response to another later selection to configure the protocol or task, for example. In yet another embodiment, changes applied to the settings are shown after the configuration screen closes by automatically displaying an updated UI 1100 following the saving and closing of the configuration screen. In another embodiment, a selection may be made to "Cancel" 1160 the configuration of display settings by selecting the "Cancel" button 1160, in which the Configure Confirmation: Task A window closes and returns to another screen. Further, UI 1100 provides a status bar 1162 including information related to the system, including the date and time and status of the system performance, such as "Idle." Further, alarm 1164, rocker control 1166, other controls (as shown by ellipsis 1168), and door icon 1170 (for indicating when the door of cell expansion system 702 is open, for example) also provide information regarding the cell expansion system, according to embodiments.

Figure 12A:
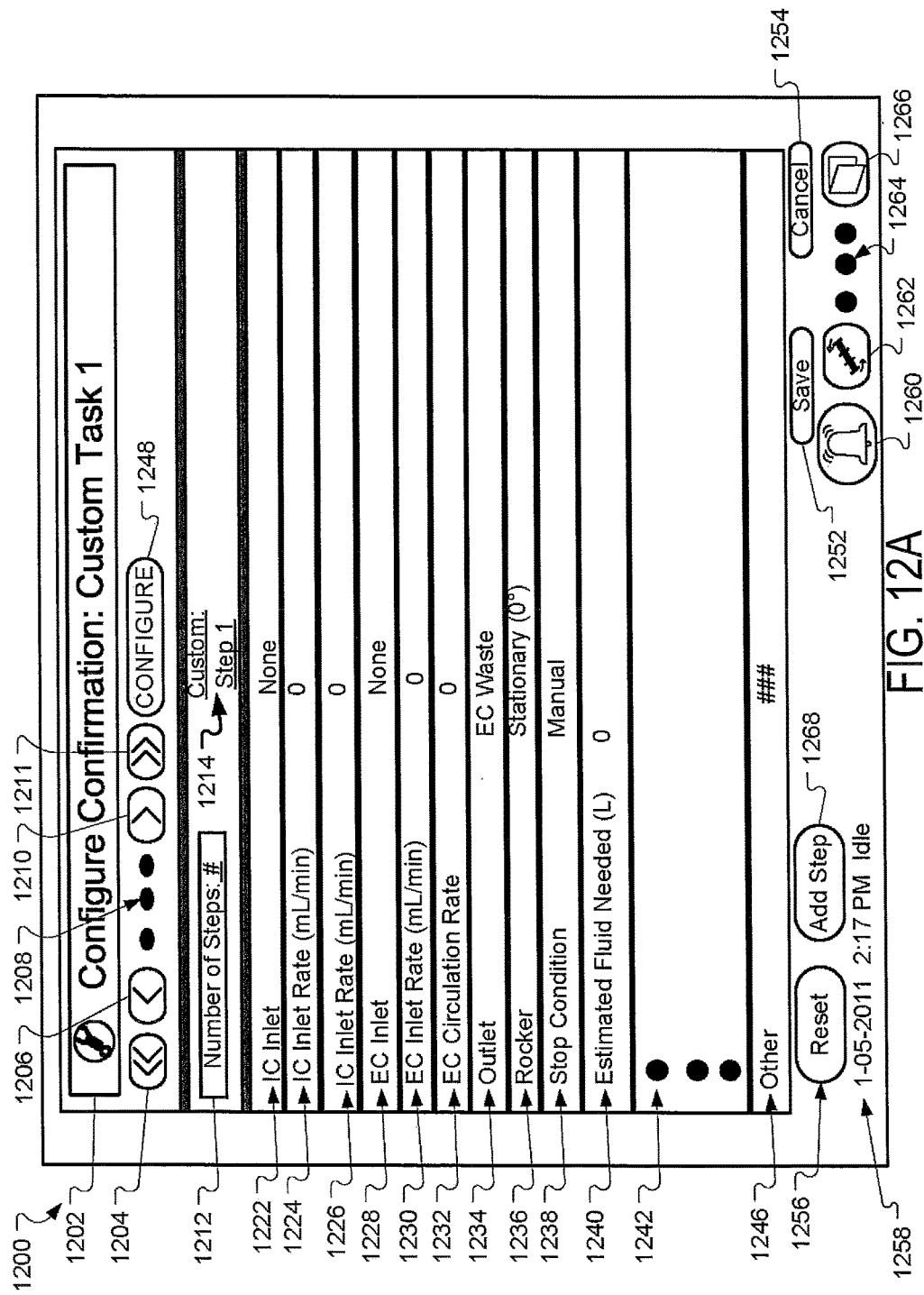
FIG. 12A illustrates an example UI for configuring settings of a custom or user-defined task used with the cell expansion system in accordance with embodiments of the present disclosure.
Figure 12B:
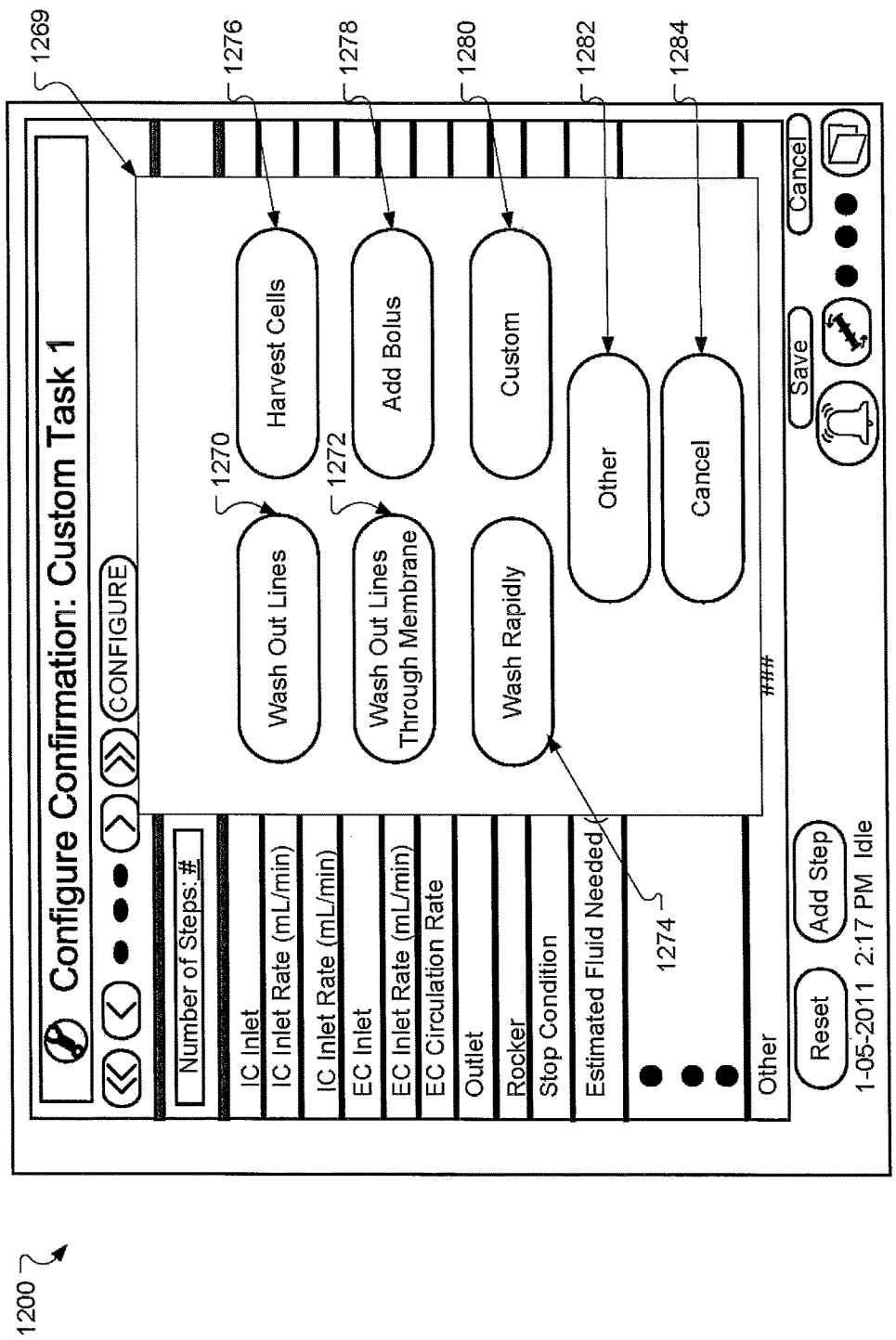
FIG. 12B depicts a window for selecting a step for adding to a custom or user-defined task in accordance with embodiments of the present disclosure.

While FIG. 11 illustrates example UI 1100 for configuring a task or protocol, with associated processes or steps, for a predetermined or pre-defined task, FIGS. 12A, 12B, and 12C depict example UI 1200 for configuring a custom or user-defined task, in accordance with embodiments of the present disclosure. A custom or user-defined task may be created according to embodiments. The system provides, in embodiments, for multiple custom or user-defined tasks, such as Custom 1, Custom 2, Custom 3, Custom 4, Custom 5, etc. In an embodiment, a custom or user-defined task allows a user or operator to enter all of the settings for a task manually. The factory default settings and setting options for a step, e.g., a first step, of a custom or user-defined task comprise the following, according to an embodiment:

| Setting | Factory Default | Setting Options |
|---|---|---|
| IC Inlet | None | Cell, Reagent, IC Media, Wash, EC Media, None |
| IC Inlet Rate | 0 mL/min | 0 to 500 mL/min |
| IC Circulation Rate | 0 mL/min | −300 to 300 mL/min |
| EC Inlet | None | Reagent, IC Media, Wash, EC Media, None |
| EC Inlet Rate | 0 mL/min | 0 to 300 mL/min |
| EC Circulation Rate | 0 mL/min | −300 to 300 mL/min |
| Outlet | EC Waste | EC Waste, IC Waste, Synchronization |
| Rocker Control | Stationary (0°) | In Motion (−180 to 270°, 0 to 15 sec), Stationary (−180 to 270°) |
| Stop Condition | Manual | Manual, Time (0.1 to 1440 min), IC Volume (1 to 4000 mL), EC Volume (1 to 4000 mL) |

Upon receiving the factory default settings, a user may manually enter data and/or make selections from selection options for a particular setting(s). In an embodiment, such selection options are provided in the form of a menu, list, window, etc. In a further embodiment, such selection options are predetermined or pre-defined. Further, a step or multiple steps may be added to a custom or user-defined task, in which the settings of each step may be modified. The system provides for a user to select a type of step to add, in which such steps include, in embodiments: Wash Out Lines, Wash Out Lines Through Membrane, Wash Rapidly, Harvest Cells, Add Bolus, and Custom. Factory default settings provided for each selected step may then be used or modified, according to embodiments. The system, in embodiments, does not save the manually entered settings but, instead, provides for the settings to be entered each time the particular custom task is performed.

In other embodiments, the settings for a custom or user-defined task, such as for Custom 1, may be configured. Configured settings may be saved, and such settings may then be used when the particular configured custom task is subsequently selected or executed, for example. As shown in FIG. 12A, a custom task, such as custom task 1, may be configured. UT 1200 may be retrieved in response to a user selecting to configure a custom task of the cell expansion system, in which a screen entitled, "Configure Confirmation: Custom Task 1" 1202 appears to allow the user to make configurations. The screen name, "Configure Confirmation: Custom Task 1" 1202 is offered as an example for purposes of illustration. Numerous types of titles, names, and/or headings may be used in accordance with embodiments of the present disclosure without departing from the spirit and scope of the present disclosure. UI 1200 appears with screen name "Configure Confirmation: Custom Task 1," for example, after the system receives a selection to configure a system task or protocol. Such selection may be initially made as shown by selecting button 808 in FIG. 8, then selecting "Custom," and then selecting the Custom Task desired, such as "Custom Task 1." The Configure Confirmation screen then appears for the selected custom task. In another embodiment, UI 1200 appears after an initial configuration to a custom or user-defined task or protocol is made, and the system is providing a confirmation of the desired configuration. Other embodiments provide for selecting the configuration of protocols, including custom protocols, through other buttons or GUI elements, for example.

As shown in FIG. 12A, UI 1200 lists the number of steps 1212 in the custom or user-defined task and displays the step(s), as shown by custom "step 1" 1214 in UI 1200. Where other steps are included, such steps may appear in the Configure Confirmation window UI 1200, or in other embodiments, such steps may be viewed by using the buttons or controls 1204, 1206, 1210, and 1211 to move between screens. Ellipsis 1208 represents other buttons or controls which may be used for moving between screens in accordance with embodiments of the present disclosure. By selecting "configure" button 1248, settings associated with "step 1" 1214 of custom task 1 may be configured. Such settings to configure include, for example, IC Inlet 1222, IC Inlet Rate 1224, IC Inlet Rate 1226, EC Inlet 1228, EC Inlet Rate 1230, EC Circulation Rate 1232, Outlet 1234, Rocker 1236, Stop Condition 1238, Estimated Fluid Needed 1240, and other settings 1246 as shown by ellipsis 1242, according to embodiments of the present disclosure. While sample data and selected options, e.g., "EC Waste," are shown in FIG. 12A for particular settings, in which such data and selected options may represent factory default settings according to embodiments, these data and selected options are shown for purposes of illustration only. The data and selected options are examples only.

Embodiments also allow for the default settings to be reset, or restored, back to the factory default settings by selection of the "Reset" button or GUI element 1256 of FIG. 12A. Selecting "Reset" 1256 restores all of the settings for a selected custom task back to the factory default settings for the custom or user-defined task, according to embodiments. Any configurations made may be saved and stored by the system by selecting the "Save" button 1252, according to an embodiment, in which the system stores and applies the configured changes. In such an embodiment, the configuration screen then closes. In another embodiment, a selection may be made to "Cancel" the configuration of display settings by selecting the "Cancel" button 1254, in which the Configure Confirmation window closes and returns to another screen. Further, UI 1200 provides a status bar 1258 including information related to the system, including the date and time and status of the system performance, such as "Idle." Further, alarm 1260, rocker control 1262, other controls (as shown by ellipsis 1264), and door icon 1266 (for indicating when the door of cell expansion system 702 is open, for example) also provide information regarding the cell expansion system, according to embodiments.

According to embodiments, a step may be added to Custom Task 1, for example, by selecting the button, "Add Step" 1268. In response to receiving a selection of add step GUI element 1268, the system provides a window or menu 1269 of options for the added step type, as shown in UI 1200 of FIG. 12B. For example, a selection may be made from the following options: Wash Out Lines 1270, Wash Out Lines Through Membrane 1272, Wash Rapidly 1274, Harvest Cells 1276, Add Bolus 1278, Custom 1280, and other step 1282. Further, a selection may be made to "Cancel" 1284 the addition of a step by selecting the Cancel button 1284, in which the selection menu or window 1269 closes. While options 1270, 1272, 1274, 1276, 1278, 1280, 1282, and 1284 are depicted in selection window 1269, any types of GUI element types may be used without departing from the spirit and scope of the present disclosure. The options presented in window 1269 are offered for purposes of illustration. Following a selection of a step from window 1269, FIG. 12C shows an updated UI 1200, including added custom "step 2" 1286 and data for settings 1222, 1224, 1226, 1228, 1230, 1232, 1234, 1236, 1238, 1240, and 1246. Further, the added step, shown as custom "step 2" 1286, may be configured through selection of the configure button 1288. Further, other step(s) may be added through selection of the "add step" button 1268, according to embodiments. The settings shown in FIGS. 12A, 12B, and 12C are shown in a table view. Other types of views may be used in accordance with embodiments of the present disclosure. The table view of UI 1200 is shown for purposes of illustration.

Figure 13A:
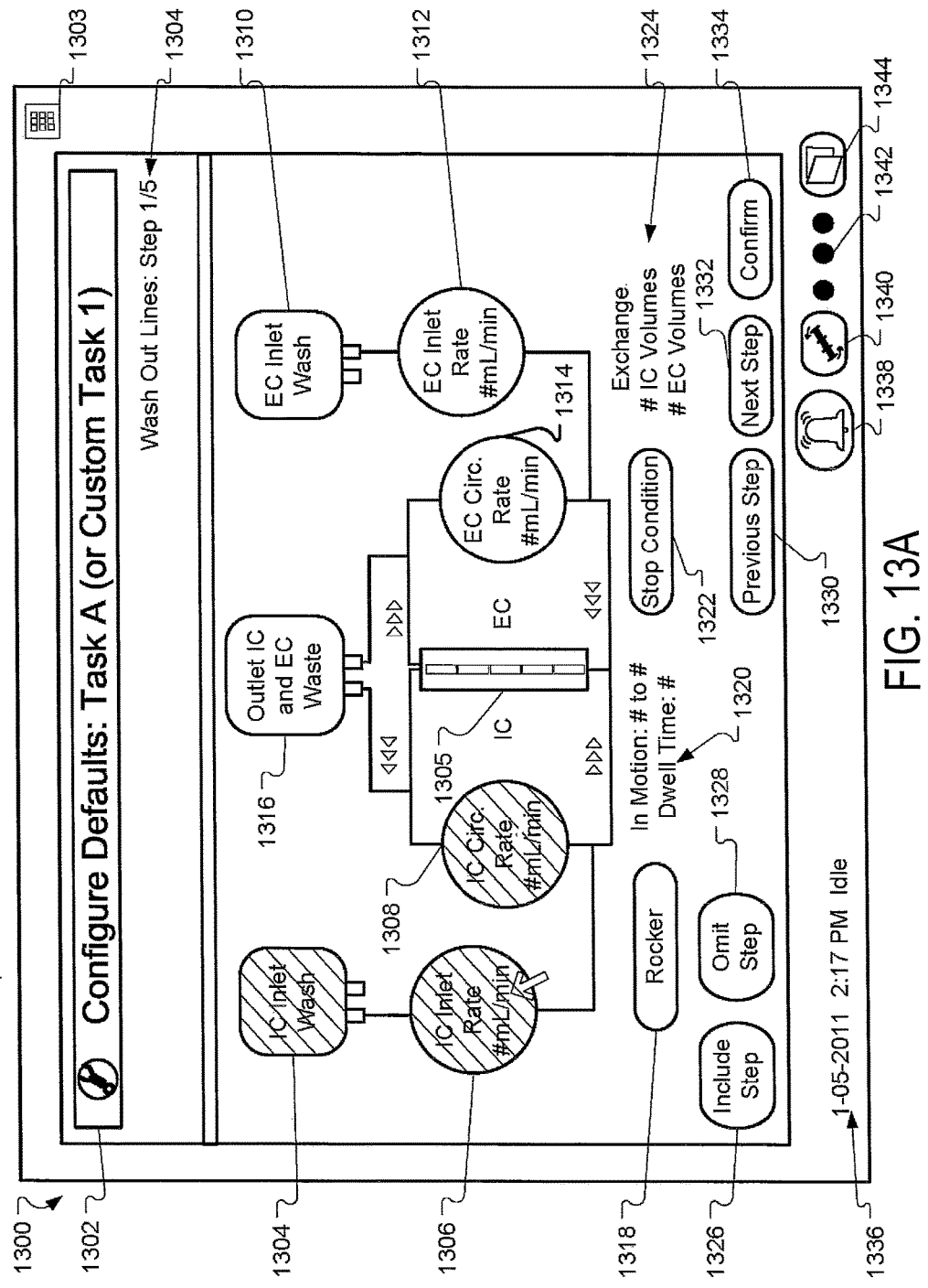
FIG. 13A depicts an example UI showing a diagram view or window for configuring a setting of a process used with the cell expansion system in accordance with embodiments of the present disclosure.

After selecting to configure a step or process of a task or protocol, a diagram view of the cell expansion system is provided as shown with UI 1300 in FIG. 13A, according to embodiments of the present disclosure. The diagram view 1300 depicts the cell expansion system, including the intracapillary (IC) and extracapillary (EC) sides of the bioreactor 1305, according to embodiments. Arrows, or other icons, in UI 1300 show the bi-directional flow between the IC and EC sides of the bioreactor. The diagram view 1300 may include designated colors or other visual indicia representing the various sides of the bioreactor, according to embodiments. Further, GUI elements, such as buttons, are associated with various settings. In embodiments, visual indicia, and changes thereof, may be used to show selections of the GUI elements associated with various settings, in which the settings include, according to embodiments: IC Inlet 1304, IC Inlet Rate 1306, IC Circulation Rate 1308, Outlet IC and EC Waste 1316, EC Circulation Rate 1314, EC Inlet Rate 1312, and EC Inlet 1310. In further embodiments, changes in visual indicia may be used to show those settings capable of being modified or configured. In embodiments, settings may be configured only for settings that are available for the selected task. If a setting cannot be configured, the button, or other GUI element, associated with the setting is not enabled, in accordance with embodiments. For example, the GUI elements 1304, 1306, and 1308 associated with settings IC Inlet, IC Inlet Rate, and IC Circulation Rate, respectively, are shown as enabled in UI 1300. Embodiments also provide for changes in visual indicia to show the status of a task when the system is performing the task, for example.

As noted, UI 1300 appears with screen name "Configure Defaults: Task A" 1302 upon selection of a step to configure. As shown in FIG. 13A, a custom or user-defined task, such as custom task 1, may be configured through the use of the diagram view depicted in UI 1300. The diagram view depicted in UI 1300 may also be referred to as a configure defaults screen, according to an embodiment. UI 1300 further includes text indicating the step or process being configured 1304, in which the example shown in UI 1300 indicates that the "Wash Out Lines: Step 1/5" 1304 is being configured. Text 1304 is offered for purposes of illustration. Any other steps or text may be used in accordance with embodiments of the present disclosure. While the diagram view depicts the cell expansion system in UI 1300, a tabular view of the setting data may also be selected with icon 1303, according to embodiments. Further, UI 1300 provides for the rocker setting 1318 to be configured, in which the rocker setting determines the position and movement of the bioreactor during a step or process. In an embodiment, the rocker setting 1318 may be designated as stationary. In another embodiment, the rocker setting 1318 may be designated as in motion, in which the range of degrees of motion determines the clockwise or counter-clockwise movement direction of the bioreactor 1305. Further, the rocker includes a dwell time setting which indicates the amount of time the system rests at the start and end positions. Rocker GUI element 1318 may be selected to set any of these settings 1320, according to embodiments. Further, stop condition GUI element 1322 provides for determining how and when the cell expansion system stops the performance of a current task or step of a task. For example, the stop condition setting options include, according to embodiments: manual, time, IC volume, EC volume, exchange, and empty air removal chamber (ARC). As shown in FIG. 13A, UI 1300 has a stop condition 1322 of Exchange 1324, for example.

Diagram view 1300 of FIG. 13A further illustrates buttons to include 1326 or omit 1328 the step depicted, according to embodiments. A user or operator may also desire to configure a previous step 1330 or a next step 1332 and move to the configuration screens for these respective steps by selecting previous step button 1330 or next step button 1332, respectively. After making desired configurations to the setting or settings of the noted step, the "confirm" GUI element 1334 may be selected to confirm the configurations and close the diagram view of UI 1300. UI 1300 provides a status bar 1336 including information related to the system, including the date and time and status of the system performance, such as "Idle." Further, alarm 1338, rocker control 1340, other controls (as shown by ellipsis 1342), and door icon 1344 (for indicating when the door of cell expansion system 702 is open, for example) also provide information regarding the cell expansion system, according to embodiments.

Figure 13B:
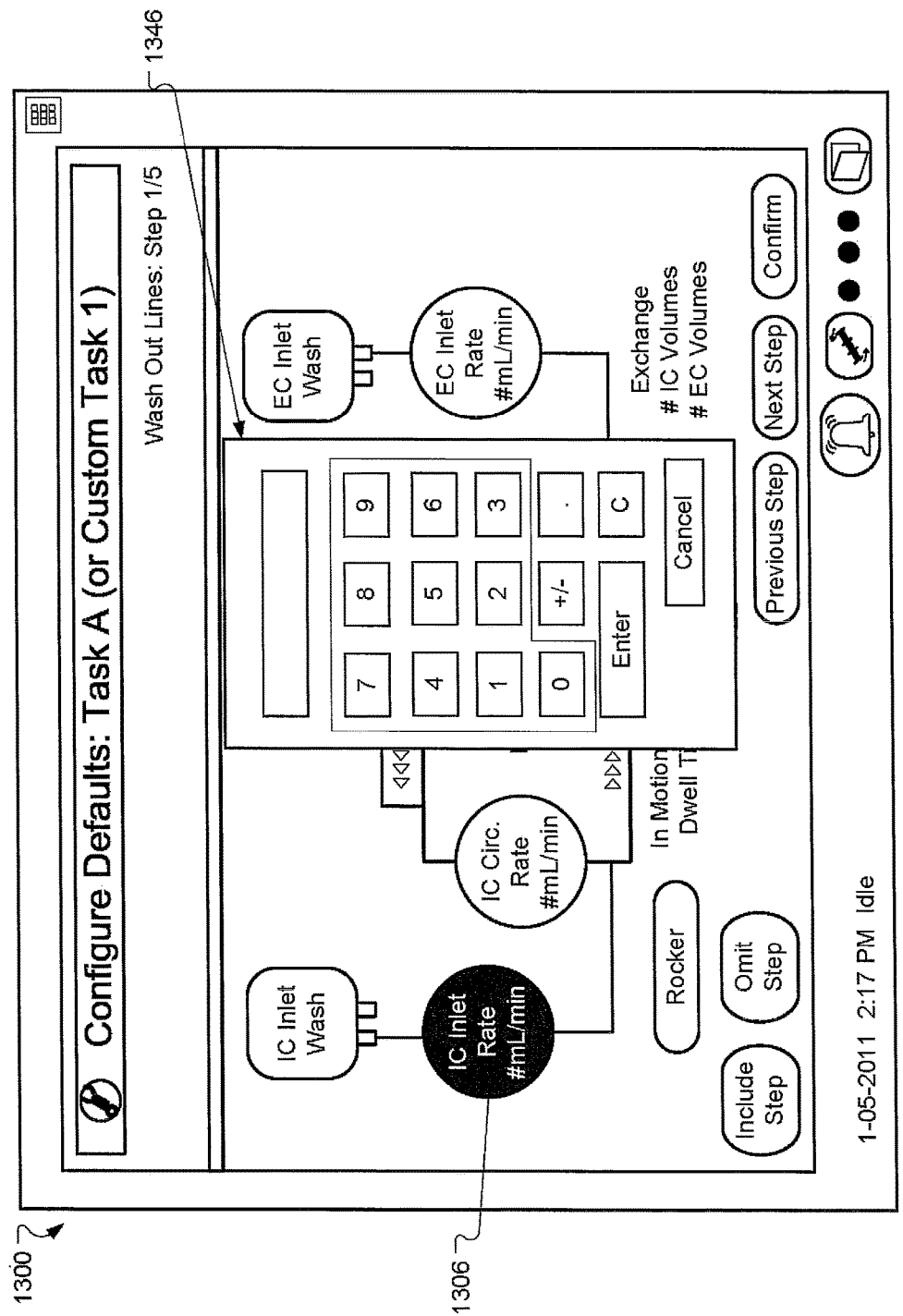
FIG. 13B illustrates an example data entry window with the example UI of FIG. 13A for providing data for configuring a protocol for use with the cell expansion system in accordance with embodiments of the present disclosure.

In the embodiment shown in FIG. 13A, the GUI element associated with the IC Inlet Rate setting 1306 is selected, as shown by the arrow, or pointer, at GUI element 1306 in UI 1300. In response to selection of GUI element 1306, the system determines that the IC Inlet Rate is associated with a numeric value and provides a data entry window 1346 or data entry pad 1346 in the diagram view 1300 depicted in FIG. 13B. As shown in FIG. 13B, GUI element 1306 is depicted as selected, as shown by the change of a visual indicator, e.g., a first indicator, associated with GUI element 1306 in FIG. 13B as compared to a visual indicator, e.g., a second indicator, associated with GUI element 1306 in FIG. 13A. After providing data using data entry window 1346, GUI element 1306 is updated to reflect the received data, according to embodiments.

Figure 13C:
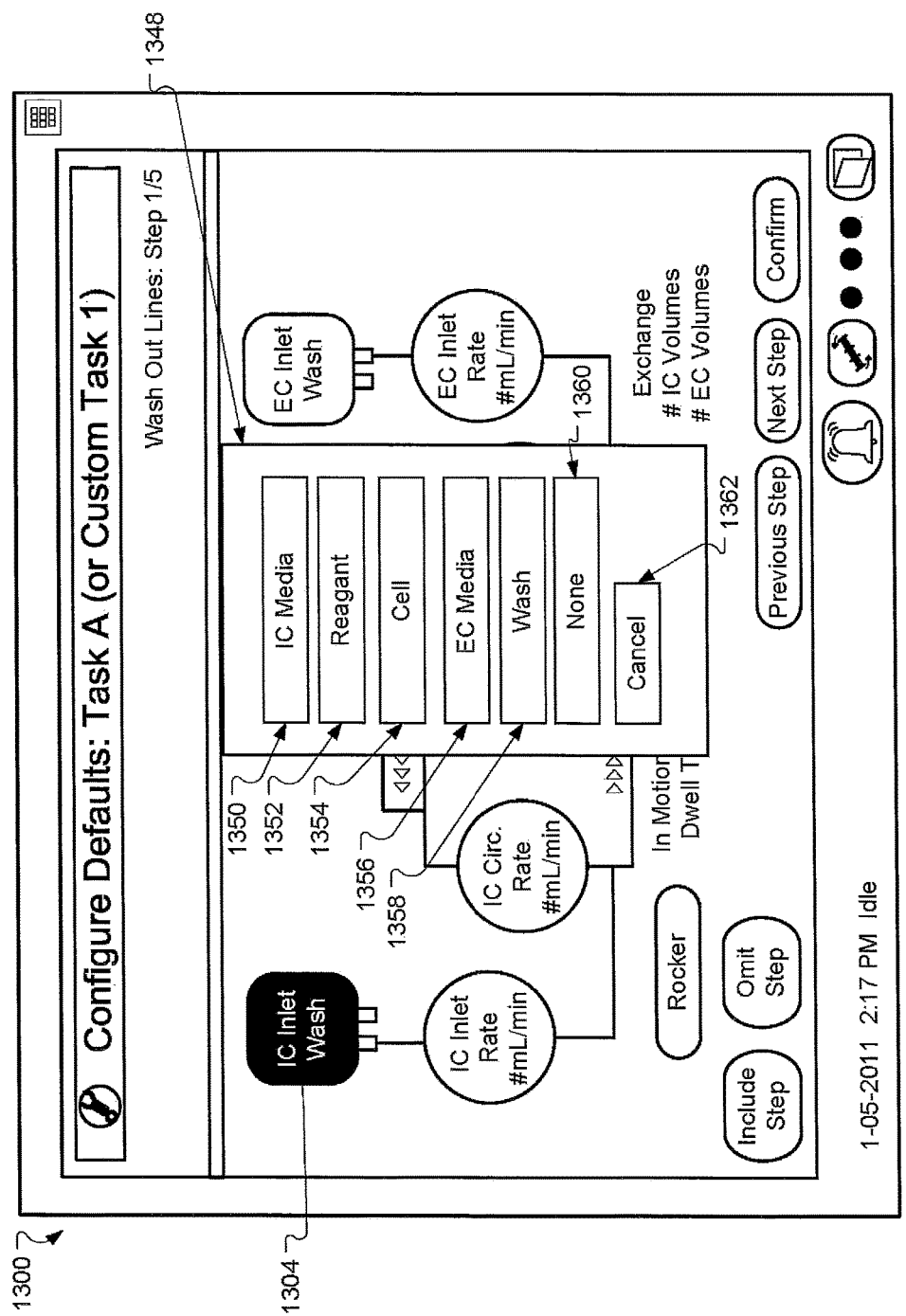
FIG. 13C depicts an example window of selection options with the example UI of FIG. 13A for configuring a protocol for use with the cell expansion system in accordance with embodiments of the present disclosure.
Figure 14A:
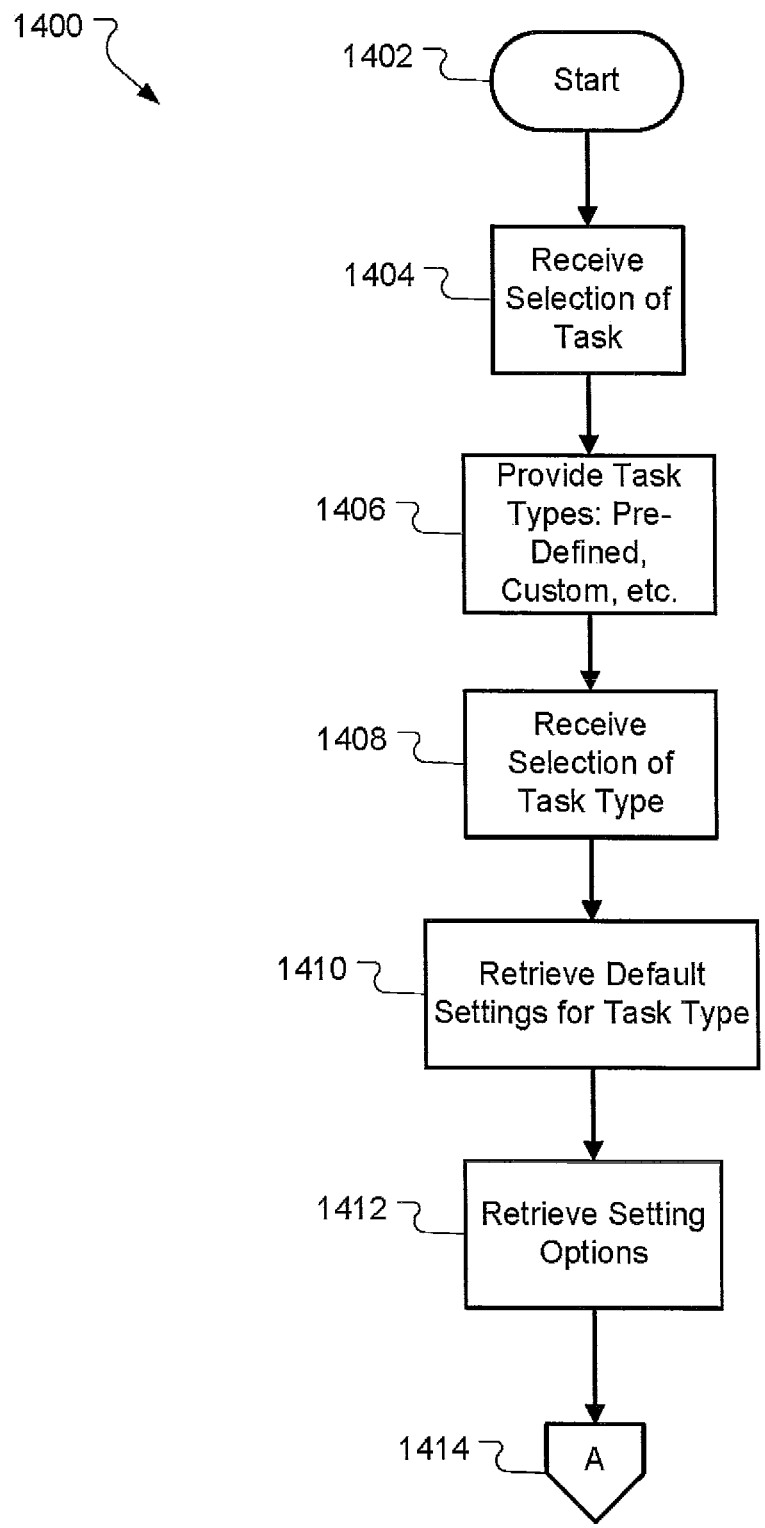
FIGS. 14A, 14B, 14C, and 14D illustrate a flow diagram depicting the operational characteristics of a process for modifying the settings of a protocol for use with the cell expansion system in accordance with embodiments of the present disclosure.
Figure 14B:
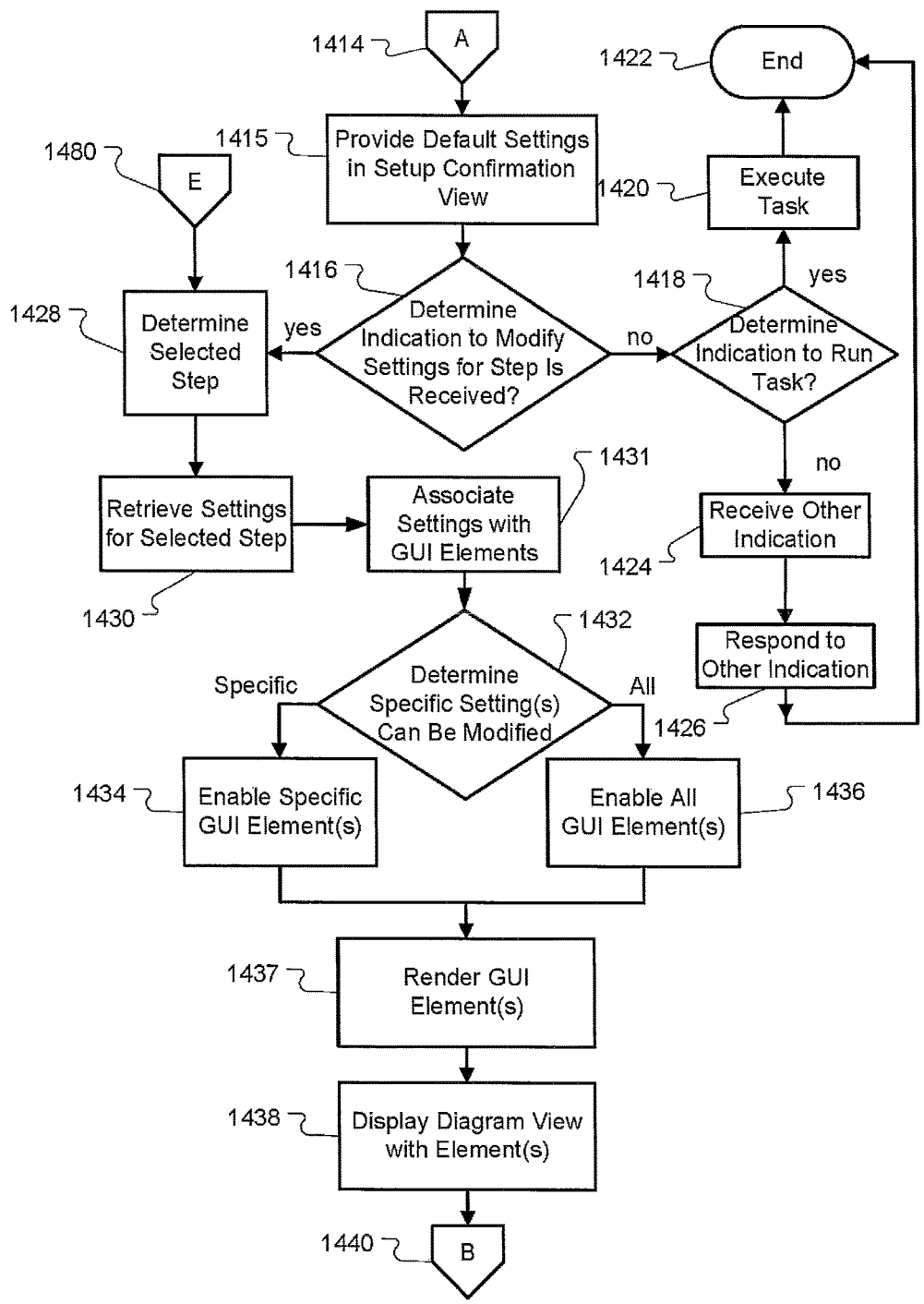
Figure 14C:
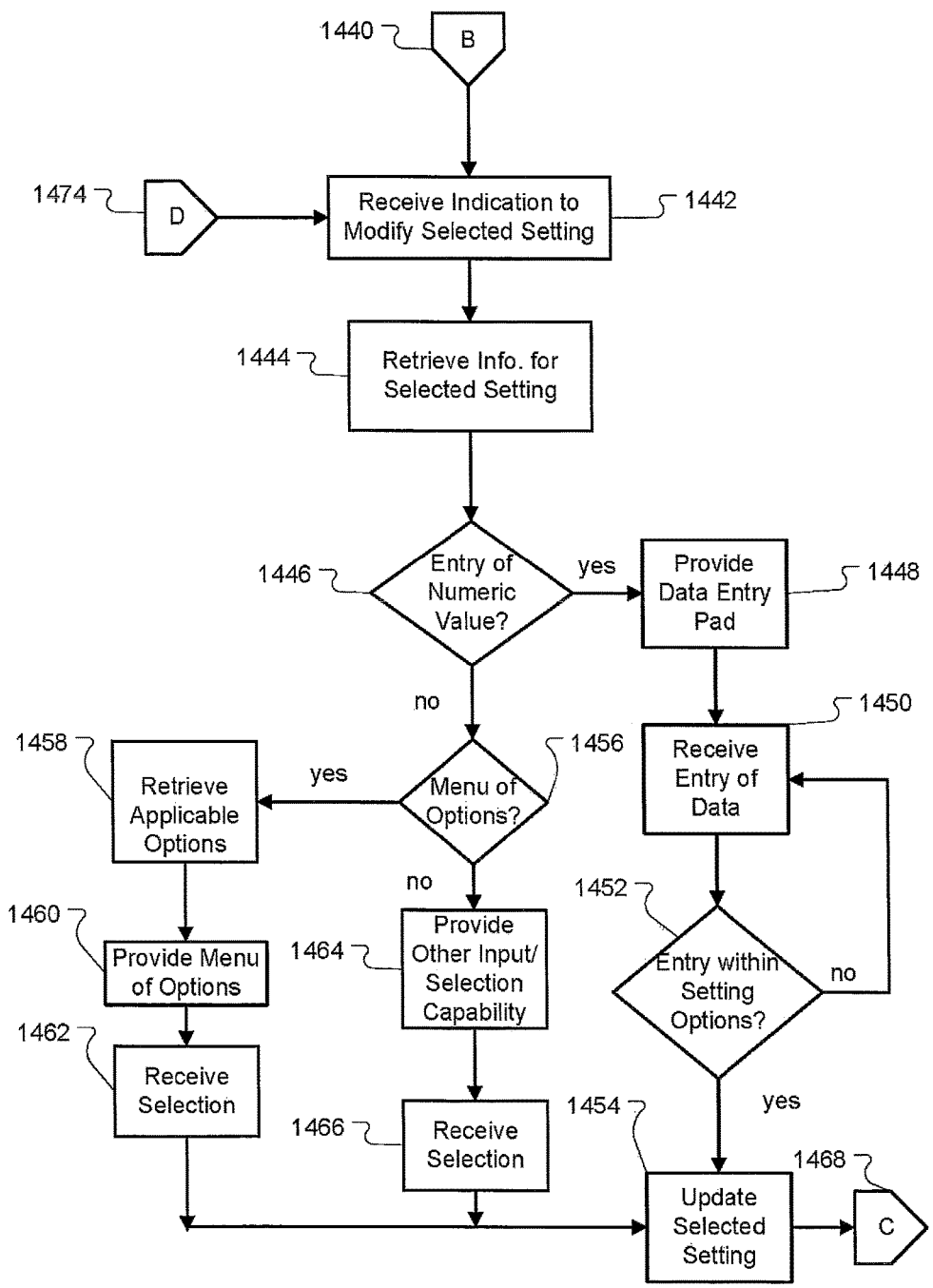
Figure 14D:
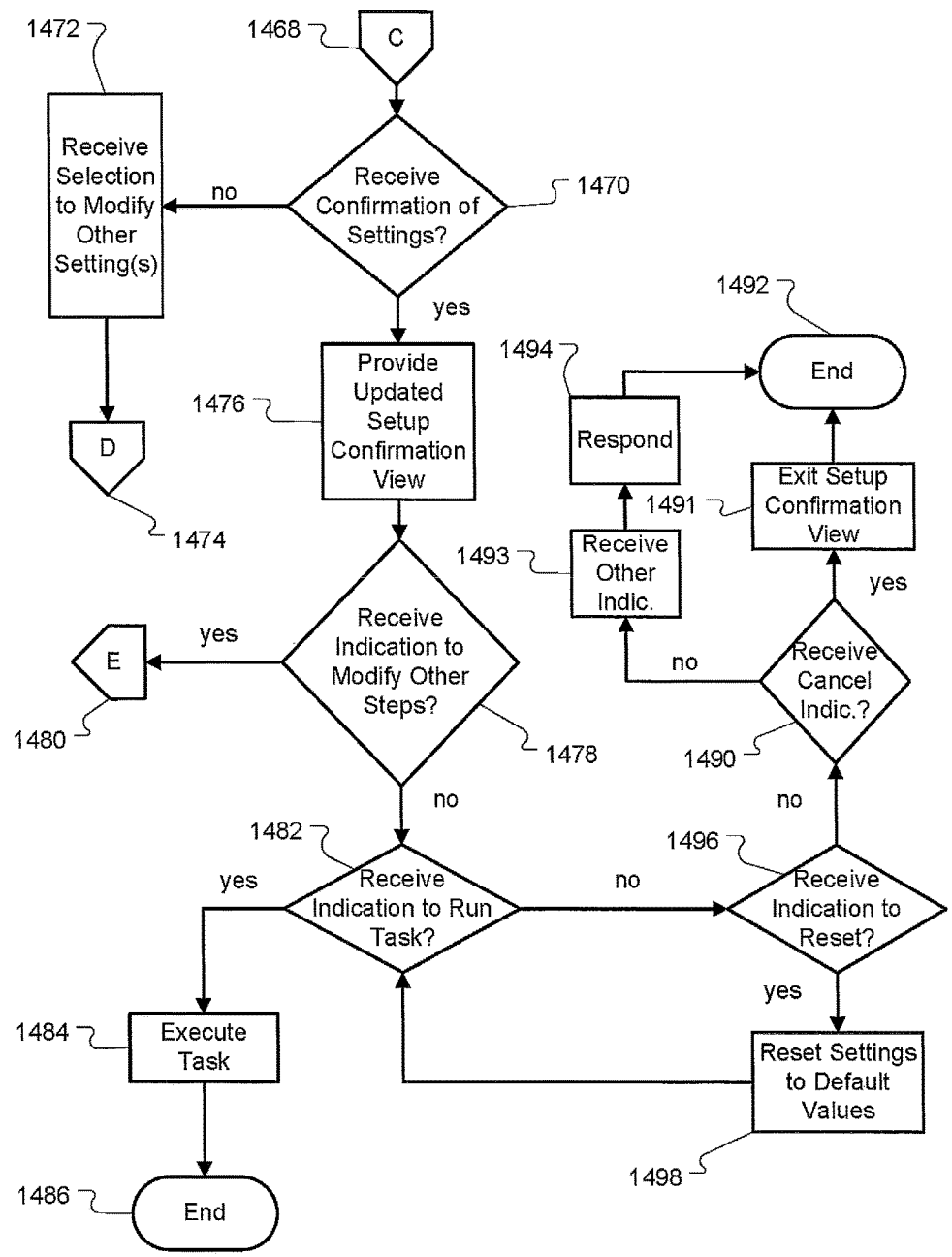

In another embodiment, GUI element 1304 is selected, as shown by the change of a visual indicator, e.g., second indicator, associated with GUI element 1304 of UI 1300 in FIG. 13C as compared to a visual indicator, e.g., first indicator, associated with GUI element 1304 in FIG. 13A. Upon receiving the selection of GUI element 1304 for configuration, the system determines that GUI element 1304 is associated with the IC Inlet and that a selection option is applicable to the IC Inlet. The system then retrieves the applicable selection options for the IC Inlet and presents the options in window or menu 1348. For example, window or menu 1348 provides selection options for the IC Inlet of: IC Media 1350, Reagent 1352, Cell 1354, EC Media 1356, Wash 1358, or None 1360. Further, the window or menu 1348 provides for a user or operator to cancel the selection of a setting type for GUI element 1304 by selecting the "Cancel" button 1362 in menu or window 1348. In an embodiment, the GUI element 1304 depicted in the diagram view of UI 1300 is then updated with the selection made with window or menu 1348. In an embodiment, the IC Inlet is shown as depicting a "Wash" for the task listed of "Wash Out Lines" 1304. However, these settings and task type, as noted, are offered for purposes of illustration only.

While FIGS. 13A, 13B, and 13C show the selections of particular GUI elements, these selections are offered for purposes of illustration. Any types of selections may be made in embodiments. In addition, diagram view 1300 may include additional data, controls, and/or other GUI elements, including a pressure window, temperature window, system window, etc. (not shown), according to embodiments. Diagram view 1300 may also include fewer GUI elements, data, etc., according to other embodiments.

With respect to FIGS. 8, 9A, 9B, 9C, 9D, 10A, 10B, 11, 12A, 12B, 12C, 13A, 13B, and 13C above, while a single UI associated with each screen may be provided according to embodiments of the present disclosure, multiple UIs can be displayed in accordance with other embodiments disclosed herein. Ills 800, 900, 1000, 1100, 1200, and 1300 are offered for purposes of illustration. Any type of UIs and GUI elements can be used in accordance with embodiments of the present disclosure. In another embodiment, a UI is not used. Rather, a configuration selection, input data, and output data may be provided by another device, output, etc., in accordance with embodiments of the present disclosure.

While various example UIs for interacting with a user or operator, for example, of the cell expansion system have been described, FIGS. 14A, 14B, 14C, and 14D illustrate example operational steps 1400 for modifying a predetermined or pre-defined task type, in accordance with embodiments of the present disclosure. Start operation 1402 is initiated by opening a home screen, for example, of the cell expansion system, and process 1400 proceeds to receive selection of a task operation 1404, in which a button or other GUI element for selecting a task or protocol is selected. In embodiments, a home screen of the cell expansion system comprises GUI elements to allow a selection of a desired action, such as a selection to execute a task, a selection to configure a setting, etc. The system then provides a choice of task types, including pre-defined or predetermined tasks 1406, such as load tasks, wash tasks, add tasks, and harvest tasks, according to embodiments. Further embodiments provide for the task types to be further described, in which specific task names are provided for the task types, including the following:

Load tasks: High flux load, load with circulation, coat bioreactor, cell attachment Wash: Bone marrow washout, aggressive washout, IC EC washout, IC EC washout through membrane, wash inlet line Add: Continuous add with ultrafiltration, reagent add, bolus add, continuous add Harvest: Harvest cells, release adherent cells, release with harvest.

The type of task selected is then received 1408, and the default settings for the selected task type are retrieved 1410. Setting options for the task type are also retrieved 1412. Process 1400 then continues via off-page reference A 1414 to operation 1415 of FIG. 14B, in which the default settings are provided in table form in a setup confirmation view screen. Next, it is determined 1416 whether an indication is received to modify the settings for a process or step, in which a "Modify" button or other GUI element may be selected in the setup confirmation view screen. If an indication to modify a setting is not received, process 1400 proceeds NO to query 1418 to determine if an indication to execute the task is received. In an embodiment, an indication to execute the task comprises selecting a "Start" button or other UI element indicating to run the task. If an indication to execute the task is received, the system executes or performs the task 1420. Process 1400 then terminates at END operation 1422. If query 1418 determines that an indication to run the protocol is not received, process 1400 proceeds to receive another indication 1424, such as an indication to exit the setup screen, for example. Other indications may be received in other embodiments. The system then responds to the received indication 1426, and process 1400 then terminates at END operation 1422.

Returning to query 1416, if it is determined that an indication is received to modify a setting, process 1416 proceeds YES to determine the step selected to modify 1428. The settings associated with the selected step are then retrieved 1430. The retrieved setting(s) are associated with GUI element(s) 1431. For example, the system associates 1431 a setting, e.g., a first setting, with a GUI element, e.g., a first GUI element. The GUI element may be further associated with data associated with the setting, e.g., default data, according to embodiments. For example, a GUI element may be associated with a numeric value, a media type, e.g., Cells, Reagent, etc., depending on the associated setting type. In embodiments, the first GUI element displayed in the diagram window shows the default data associated with the first GUI element.

Query 1432 then determines if specific settings are available for modification, e.g., a determination is made as to whether specific settings can be modified, in which the settings capable of being modified are identified by the system. In response to determining that all settings associated with the selected step can be modified, process 1400 proceeds "All" to enable for selection all GUI element(s) associated with the setting(s) 1436. On the other hand, in response to determining that only specific settings are available for modification, process 1400 branches "Specific" at query 1434 to enable specific GUI elements for selection 1434. A diagram view or window showing the enabled and/or non-enabled settings is then provided, in which such providing includes: rendering the GUI element(s) 1437 and displaying the diagram view or window with the enabled and/or non-enabled GUI element(s) 1438. Process 1400 then continues through off-page reference B 1440 to operation 1442 of FIG. 14C, in which an indication to modify a selected setting is received by selection of a GUI element associated with the desired setting in the diagram view, according to an embodiment of the present disclosure. Information for the selected setting is then retrieved 1444.

Next, the system determines at query 1446 whether the selected setting is associated with a numeric value. For example, a rate, such as the IC Inlet Rate, is associated with a numeric value. If it is determined 1446 that the selected setting is associated with a numeric value, process 1400 branches YES to provide data entry pad 1448. An entry of data is received 1450. It is then determined whether the entry is within the range of setting options 1452. If the entry is within the range of setting options, process 1400 proceeds YES to update the selected setting 1454. Process 1400 then continues through off-page reference C 1468 to query 1470. If the entry is not within the range of setting options, process 1400 proceeds NO to receive another data entry 1450, and process 1400 then continues to operation 1452. In an embodiment, query 1452 is optional, and process 1400 proceeds directly to update the setting 1454 according to the received value.

Returning to query 1446, if the selected setting is not associated with a numeric value, process 1400 proceeds NO to query 1456 to determine whether a menu or window of options is applicable to the selected setting. If a menu or window of options is applicable to the selected setting, process 1400 proceeds YES to retrieve applicable options 1458. The menu or window of options is then provided 1460, and a selection is received 1462. The selected setting is then updated 1454, and process 1400 proceeds through off-page reference C 1468 to query 1470. Returning to query 1456, if a menu or window of options 1456 is not applicable to the selected setting, process 1400 proceeds NO to provide other input/selection capability, such as a field, button, control, etc., 1464. A selection is then received 1466, and the selected setting is updated 1454. Process 1400 then proceeds through off-page reference 1468 to query 1470 of FIG. 14D.

Next, query 1470 determines whether a confirmation of the settings provided is received. If a confirmation is not received, query 1470 proceeds NO to receive a selection to modify another setting or settings 1472 from within the diagram view. Process 1400 then proceeds through off-page reference D 1474 to FIG. 14C, and process 1400 then continues at operation 1442. If query 1470 determines that the modified settings are confirmed, process 1400 proceeds YES to provide an updated setup confirmation view, such as in table form, for example, 1476. It is next determined 1478 whether an indication is received to modify any other steps 1478 from within the setup confirmation view. If it is desired to modify other steps, process 1400 proceeds YES to off-page reference E 1480, and process 1400 then continues to FIG. 14B where the selected step for modification is determined 1428. If it is determined at query 1478 not to modify other steps, process 1400 proceeds NO to determine whether an indication is received to execute the task 1482. If a selection to run the task is received, process 1400 proceeds YES to execute task operation 1484, in which the protocol is performed with the cell expansion system. Process 1400 then terminates at END operation 1486. If an indication is not received to execute the task 1482, process 1400 proceeds NO to query 1496 to determine whether an indication is received to reset the modified setting(s) to the factory default settings. If an indication to "Reset" is received, such as by selecting a GUI element associated with the "Reset" functionality, process 1400 proceeds YES to reset the settings to the default values 1498. In an embodiment, the default values comprise the factory default values. If an indication to reset is not received, process 1400 proceeds NO to query 1490 to determine whether an indication to cancel the setup for the selected protocol is received. If an indication to cancel is received, process 1400 proceeds YES to exit the setup confirmation view 1491. Process 1400 then terminates at END operation 1492. If an indication to cancel is not received 1490, process 1400 proceeds NO to receive another indication 1493, such as an indication to move to another screen, for example. The system then responds 1494 to the indication, and process 1400 terminates at END operation 1492.

Figure 15A:
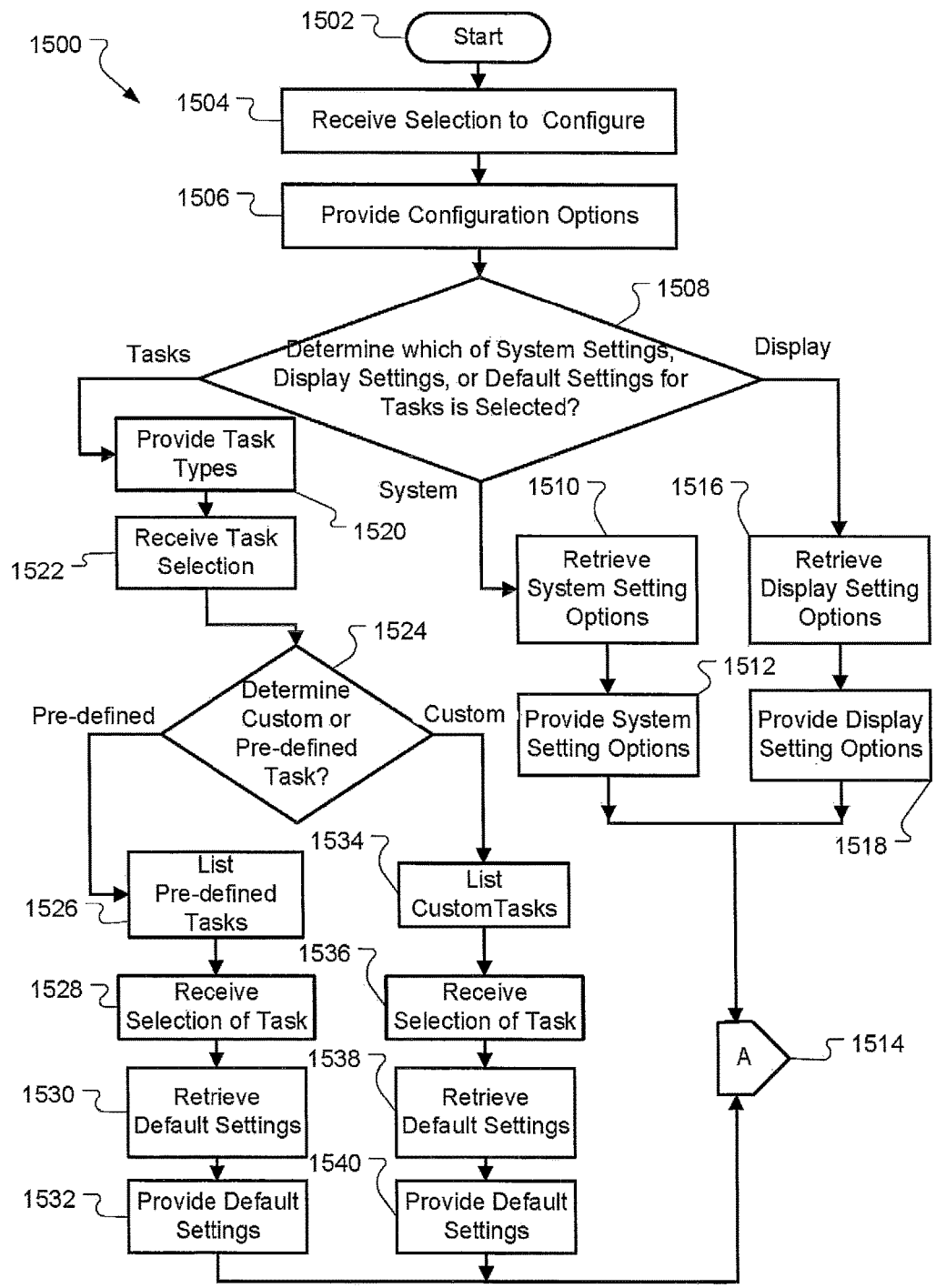
FIGS. 15A and 15B depict a flow diagram illustrating the operational characteristics of a process for configuring aspects of the cell expansion system in accordance with embodiments of the present disclosure.
Figure 15B:
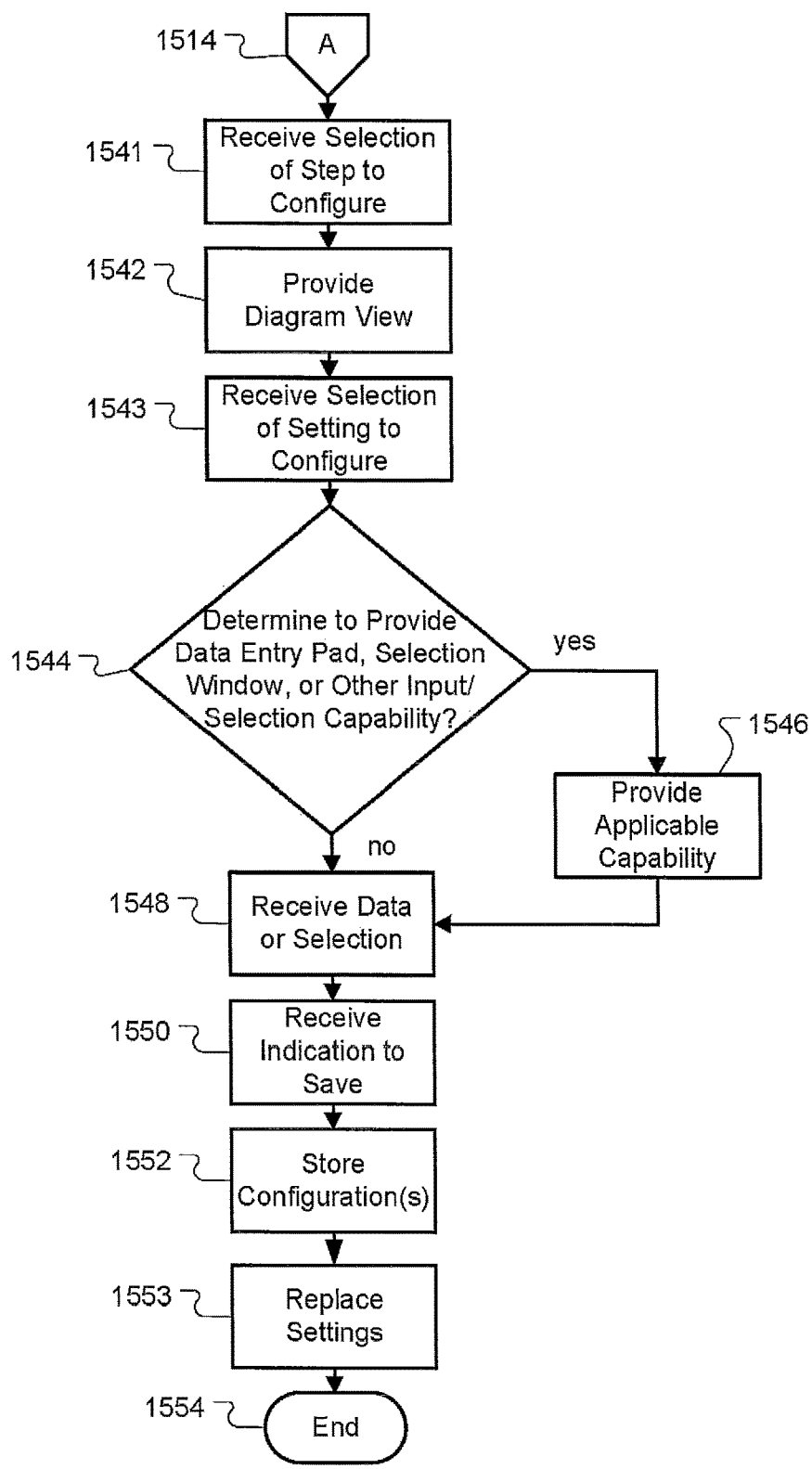

While FIGS. 14A, 14B, 14C, and 14D relate to modifying a setting(s) of a step of a protocol or task, FIGS. 15A and 15B illustrate example operational steps 1500 for configuring settings of the cell expansion system, in which such settings are stored and replace the applicable default settings, in accordance with embodiments of the present disclosure. Start operation 1502 is initiated, and process 1500 proceeds to receive a selection to configure a setting 1504, in which a "Configuration" GUI element related to configuration aspects for the system, such as a GUI element displayed on the system home screen, is received. In response to receiving the selection to configure 1504, the system provides configuration options 1506, including options to configure the display settings, system settings, and/or task default settings. Next, it is determined 1508 which of system settings, display settings, or task default settings is selected for configuration. If the system settings are selected 1510, process 1500 proceeds to retrieve system setting options 1510, and the system setting options for configuration, such as alarm sound, incubator "on" or "off," etc., are provided 1512, according to embodiments. Process 1500 then continues through off-page reference A 1514 to operation 1541 of FIG. 15B. If it is desired to configure display settings, process 1500 proceeds to retrieve the display setting options 1516, and the display setting options are provided 1518, in which such display setting configuration options include date and time format, etc., according to embodiments.

Alternatively, if the default settings for tasks is selected, process 1500 proceeds to provide the task types 1520, including pre-defined or predetermined tasks and custom tasks, according to an embodiment. A selection of the task type desired is received 1522, and it is determined 1524 which selection has been made, i.e., custom or pre-defined or predetermined task. If a predetermined or pre-defined task selection is received, process 1500 branches "Pre-Defined" to providing a list of the pre-defined task options 1526, receiving a selection of a predetermined task option 1528, retrieving default settings 1530 for the selected task, and providing the default settings for the selected predetemiined task 1532. Process 1500 then continues through off-page reference A 1514 to operation 1541 of FIG. 15B. Returning to query 1524, if a custom or user-defined task selection is received, process 1500 branches "Custom" to listing custom or user-defined task options, such as Custom Task 1, Custom Task 2, etc., 1534. A selection of a custom task option, e.g., Custom Task 1, is received 1536. Default settings for the custom task are retrieved 1538, and the default settings for the custom task are provided 1540. Process 1500 then proceeds through off-page reference A 1514 to operation 1541 of FIG. 15B.

At operation 1541 of FIG. 15B, a selection of a particular step or process of the task to configure is received, in accordance with embodiments of the present disclosure. In embodiments, the system then provides a diagram view 1542 of the cell expansion system for the step selected. A selection of a GUI element associated with a setting to configure is then received 1543, and it is determined whether the selected setting is associated with a numeric value, selection window or menu, or other input capability using a window or other control 1544. If the selected setting is associated with a data entry window, selection window or menu, or other input/selection capability using a window or other control, process 1500 proceeds YES to provide the applicable capability 1546, such as a data entry pad according to embodiments. Process 1500 then proceeds to operation 1548. If query 1544 determines that a selection of data may be received, such as in a field of the GUI element, for example, without providing a data entry window, selection window, or other input/selection capability using a window or other control, process 1500 proceeds NO to receive the data or selection 1548. To store the configuration settings, an indication to "Save" is received 1550, in which the system then stores the configurations 1552 and replaces 1553 the default settings or previously configured settings 1553 with the newly configured settings. In an embodiment, the first settings are replaced with the second configured settings 1553. Process 1500 then terminates at END operation 1554.

Figure 16:
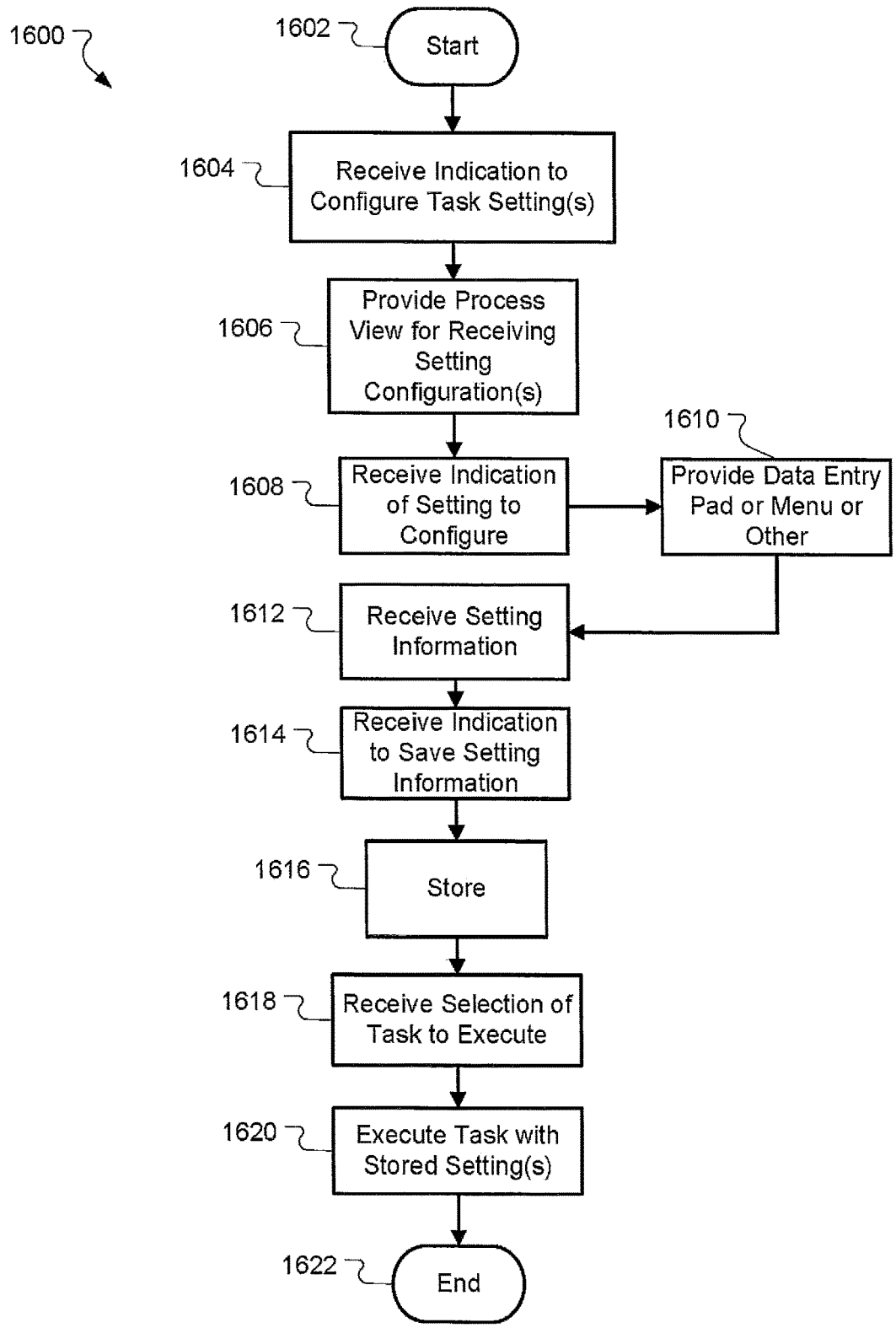
FIG. 16 illustrates a flow diagram showing the operational characteristics of a process for executing a configured task with the cell expansion system in accordance with embodiments of the present disclosure.

Next, FIG. 16 illustrates example operational steps 1600 for configuring protocol or task settings, and executing the task or protocol with the configured settings, according to an embodiment of the present disclosure. Start operation 1602 is initiated, and process 1600 proceeds to receive an indication to configure a task setting(s) 1604. A process view, or diagram view, depicting the cell expansion system, including the IC and EC sides of the bioreactor and related settings as associated with GUI elements, for example, is displayed 1606. An indication of a setting to configure is then received 1608, and a data entry pad or data entry window, menu, or other input/selection capability is provided 1610 as determined by the system as meeting the particular selected setting's characteristics. Information or data for the selected setting is then received 1612, and, in response to receiving an indication to save the setting configuration 1614, the system stores the configuration 1616. Next, a selection is received to execute the configured task associated with the configured task setting 1618. In an embodiment, an indication to execute the task comprises selecting a "Start" button or other UI element indicating to run the task. The configured, and stored, settings for the selected task are retrieved, and the task is executed with the stored setting(s) 1620. Process 1600 then terminates at END operation 1622.

Figure 17:
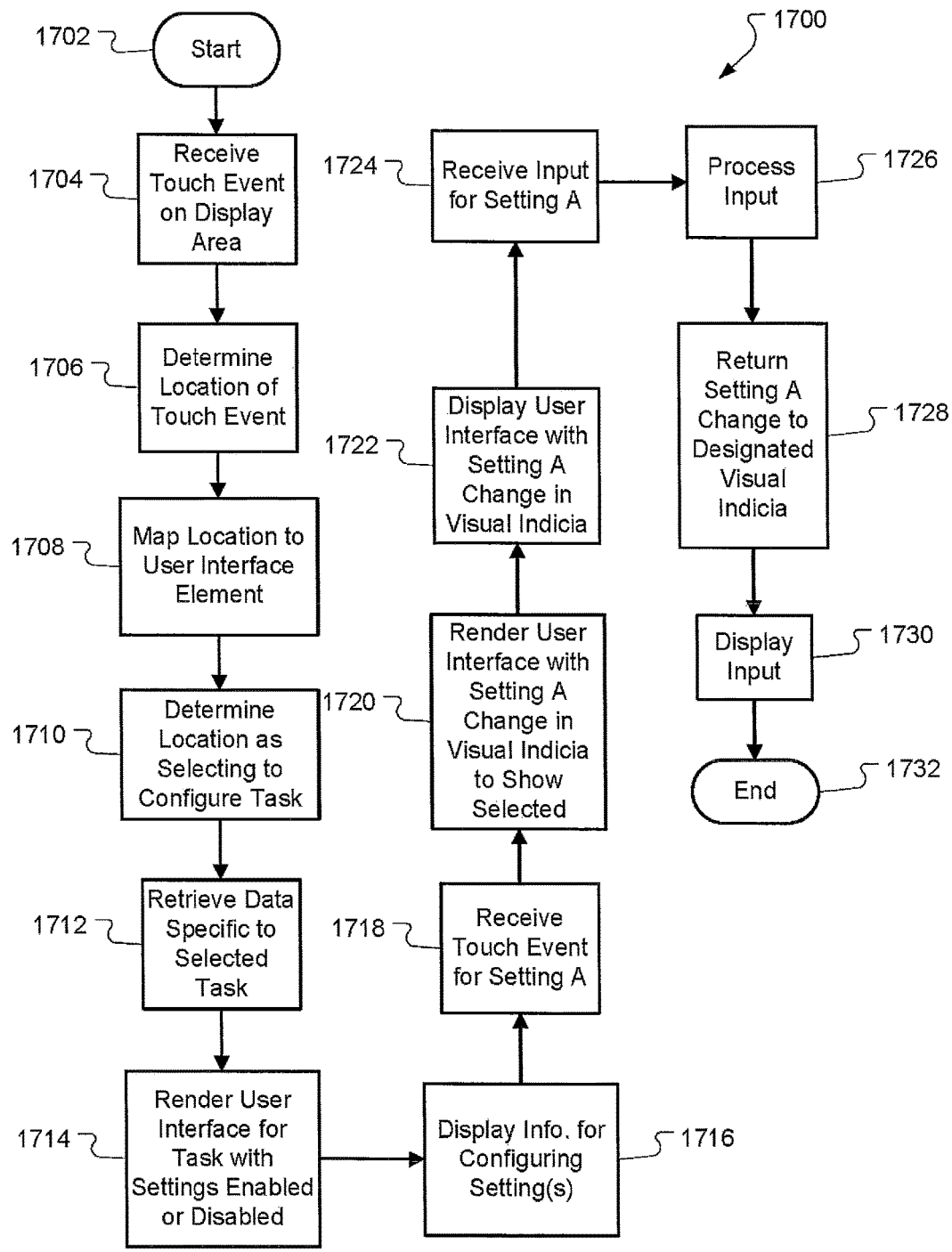
FIG. 17 depicts a flow diagram illustrating the operational characteristics of a process for mapping a location of a touch event, on a display area of the cell expansion system, to a UI element in accordance with embodiments of the present disclosure.

While FIG. 16 depicts process steps for executing a task with stored configurations, FIG. 17 illustrates example operational steps 1700 for interpreting selections made using the touch screen of a user interface of the cell expansion system, according to embodiments of the present disclosure. The touch screen of the cell expansion system allows a user or operator, for example, to communicate with and interact with the cell expansion system by selecting GUI elements, selecting options from menus or windows, entering data, etc. Start operation 1702 is initiated, such as by turning the cell expansion system "on" or displaying a home screen for the cell expansion system using a display device, according to embodiments. Process 1700 then proceeds to receive a touch event on the display area 1704, in which a user or operator touches, or uses a touch input device, for example, a GUI element on the display area of the cell expansion system, such as of cell expansion system 702 of FIG. 7. A location of the touch event 1706 is next determined, and the location is mapped to a UI element 1708. The system next determines that the location corresponds to a selection of a task configuration 1710, according to an embodiment. Data specific to the selected task configuration is then retrieved 1712, such as data associated with certain steps and/or settings of the selected task. A UI for the selected task is then rendered 1714, in which settings available for configuration are enabled. Information, such as a diagram view showing the IC and EC sides of the bioreactor with relevant settings, is then displayed for receiving configurations 1716. A touch event is then received for a setting, such as for setting "A," for example 1718. To show that setting "A" has been selected for configuration, the UI is rendered with the GUI element associated with setting A having a change in visual indicia 1720 in the diagram view, for example, to show it has been selected.

In an embodiment, a GUI element associated with setting A may be enabled before it is selected, in which the display of setting A in the diagram view shows the GUI element associated with setting A as being selectable through the use of a designated visual indicia. For example, the GUI element associated with an enabled setting may be rendered and displayed as having a first color, while a GUI element associated with a non-enabled setting may be rendered and displayed as having a second color. Where an enabled GUI element is selected, an additional change in visual indicia may apply. For example, an enabled GUI element for selected setting A is changed in color to a third color, for example, to show it is selected, e.g., such as by changing it to the color "black" when it is selected. A GUI element having a change in visual indicia to show it has been selected is displayed 1722. Input for setting A is then received 1724, such as through use of a window, selection menu, or other input/selection mechanism, according to embodiments. The input received is then processed 1726. The visual indicia for setting A is then returned 1728 to its original visual indicia, according to embodiments. For example, the visual indicia is changed from a first indicia to a second indicia when it is selected. Setting A is then returned to the first visual indicia after the requested configuration of setting A is made. The input provided for the configuring of setting A is then displayed 1730, such as within the GUI element for setting A in the diagram view and/or in the table of settings for configuration, in accordance with embodiments disclosed herein. Process 1700 then terminates at END operation 1732.

Turning to FIGS. 18A, 18B, 18C, and 18D, example operational steps 1800 are provided for configuring a pre-defined task or protocol for use with the cell expansion system and storing the configured settings, in accordance with embodiments. Start operation 1802 is initiated, and process 1800 proceeds to receiving a selection to configure 1804. Configuration selection options, including GUI elements to select to configure system settings, display settings, task settings, etc., are retrieved and provided 1806. A selection to configure the default settings for tasks is then received 1808. The types of tasks for selection are then provided 1810, and a selection of a pre-defined task is received 1812. The default settings for the selected task are then retrieved 1814, and process 1800 continues through off-page reference A 1816 to operation 1817 of FIG. 18B. At operation 1817, default settings for the selected task are provided in a configure confirmation UI, such as shown with UI 1100 of FIG. 11, for example. In an embodiment, the configure confirmation window or view includes a listing of the settings and associated data for one or more steps associated with the selected task. In an embodiment, the settings and associated data are provided in a table format. Query 1818 next determines whether an indication is received to configure the settings for a step or process associated with the selected task and displayed in the configure confirmation UI. If a selection to configure the settings for a step is not received, process 1800 proceeds NO to query 1820, in which it is determined whether a selection to cancel the configuration is received. If an indication to cancel is received, process 1800 proceeds YES to close the configuration window 1822 and exit. Process 1800 then terminates at END operation 1824, in which a home screen of the cell expansion system may appear, according to embodiments. If an indication to cancel is not received at query 1820, process 1800 proceeds NO to receive another indication 1826, such as to switch to another screen through a selection of a next screen button, control, or icon, for example. The indication received is responded to 1828, and process 1800 then terminates at END operation 1824.

Returning to query 1818, if an indication to configure settings for a step is received, process 1800 proceeds YES to determine the step selected 1830, and the setting(s) associated with the selected step are retrieved 1831. The retrieved setting(s) are associated with GUI element(s) 1832. For example, the system associates 1832 a setting, e.g., a first setting, with a GUI element, e.g., a first GUI element. The GUI element may be further associated with data associated with the setting, e.g., default data, according to embodiments. For example, a GUI element may be associated with a numeric value, a media type, e.g., Cells, Reagent, etc., depending on the associated setting type. In embodiments, a first GUI element displayed in the diagram view shows the default data associated with the first GUI element. Further, a second GUI element displayed in the diagram view shows the default data associated with the second GUI element, etc.

Query 1834 next determines if specific settings are available for configuration, e.g., a determination is made as to whether specific settings are configurable, in which the configurable settings are identified by the system. As discussed above, settings may be configured only for settings that are available for configuration for the selected task, according to embodiments of the present disclosure. If a setting cannot be configured, the button, or other GUI element, associated with the setting is not enabled for selection, in accordance with embodiments. For example, enabling the first GUI element for selection includes showing that the GUI element is capable of selection by the use of a visual indicator(s) showing such selection capabilities. For example, in embodiments, a GUI element that is not enabled is a first color, while a GUI element that is enabled is a second color. A visual indicia change comprising a color change is offered for purposes of illustration. Numerous types of visual indicia changes may be used to designate a GUI element as being enabled without departing from the spirit and scope of the present disclosure. For example, text may be used to show whether a GUI element is enabled or not enabled, such as by labels designating "Enabled" or "Not Enabled," respectively. Further embodiments also include using any type of indicia change without departing from the spirit and scope of the present disclosure, in which such indicia changes are not limited to visual indicia changes.

Returning to query 1834, in response to determining that all settings associated with the selected step are configurable, process 1800 proceeds "All" to enable for selection all GUI element(s) associated with the setting(s) 1838. On the other hand, in response to determining that only specific settings are available for configuration, process 1800 branches "Specific" at query 1834 to enable specific GUI elements for selection 1836. A diagram view or window showing the enabled and/or non-enabled settings is then provided, in which such providing includes: rendering the GUI element(s) 1837 and displaying the diagram view or window with the enabled and/or non-enabled GUI element(s) 1840. Process 1800 then proceeds through off-page reference B 1842 to operation 1844 of FIG. 18C.

At operation 1844, an indication to configure a selected setting is received, such as by receiving a selection of a GUI element associated with the selected setting. Information related to the selected setting is then retrieved 1846, including information such as whether the setting is associated with a numeric value, for example. Query 1848 determines whether the setting is associated with entry of a numeric value. If entry of a numeric value is associated with the setting, process 1800 proceeds YES to provide data entry pad or window 1850 for receiving an entry of data 1852. In an embodiment, it may be determined whether the numeric value entered is within the available setting options 1854, for example. If the entry is not within the acceptable range, process 1800 proceeds to operation 1852 to receive another data entry. If the entry is within the available range 1854, process 1800 proceeds YES to update the setting 1856 according to the received value. In an embodiment, query 1854 is optional, and process 1800 proceeds directly to update the setting 1856 according to the received value.

Figure 18A:
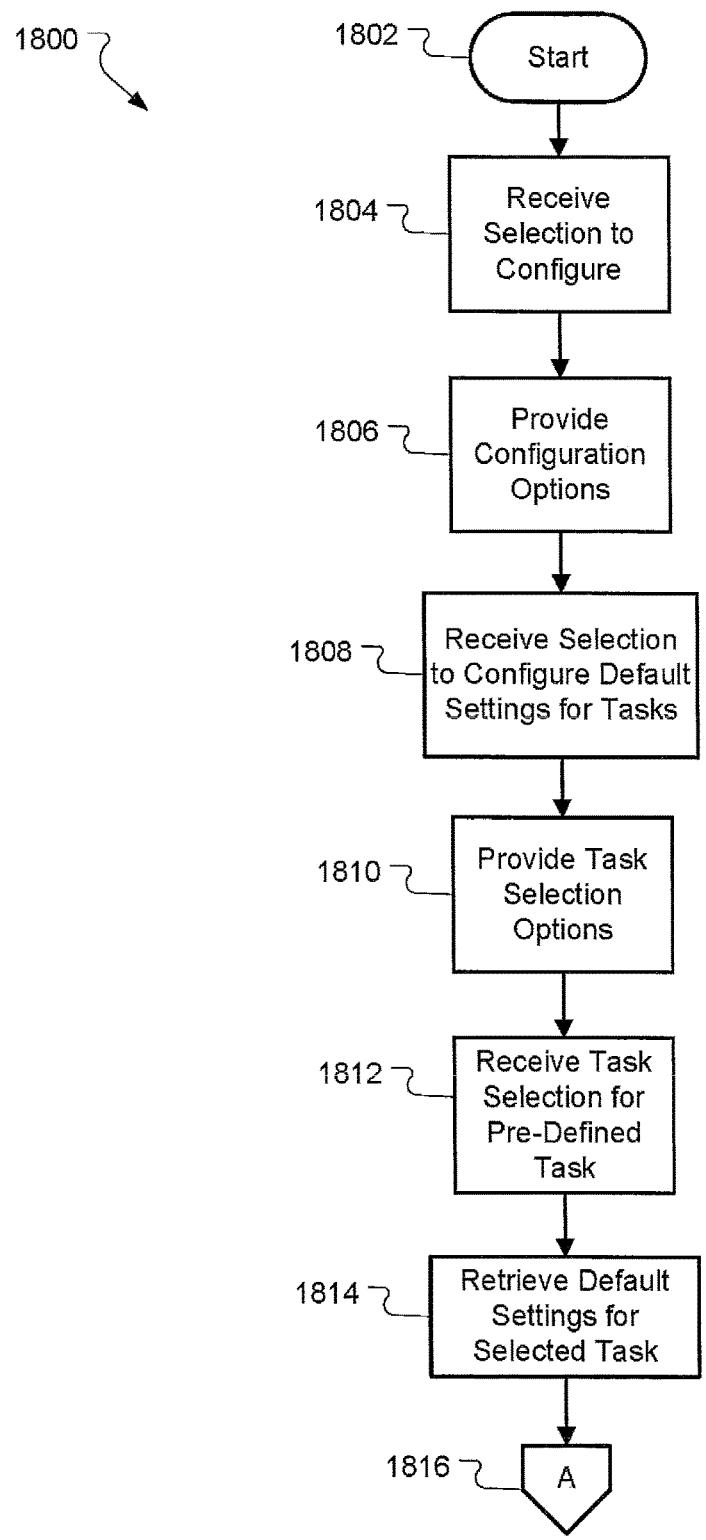
FIGS. 18A, 18B, 18C, and 18D illustrate a flow diagram showing the operational characteristics of a process for configuring the settings of a protocol used with the cell expansion system in accordance with embodiments of the present disclosure.
Figure 18B:
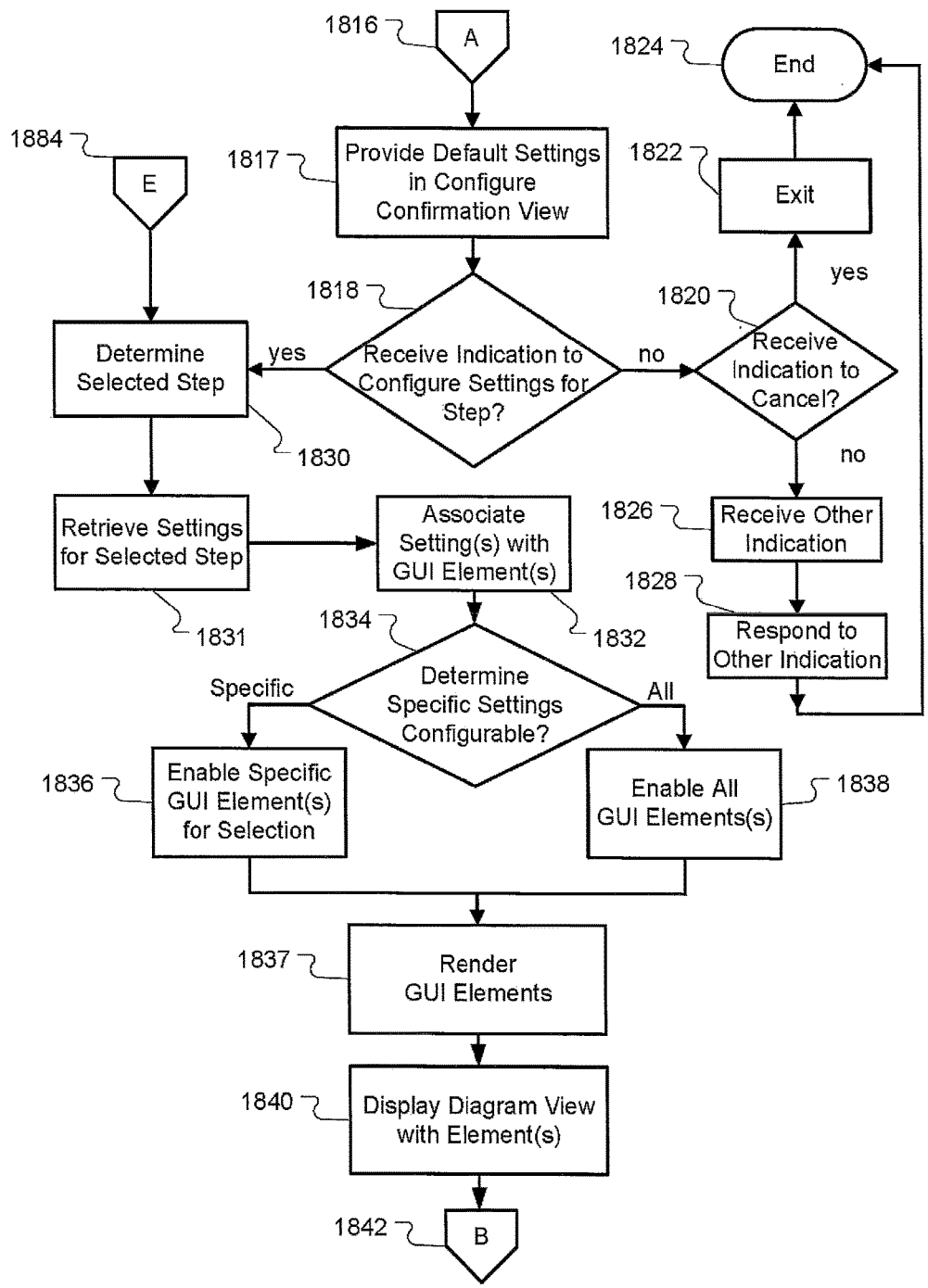
Figure 18C:
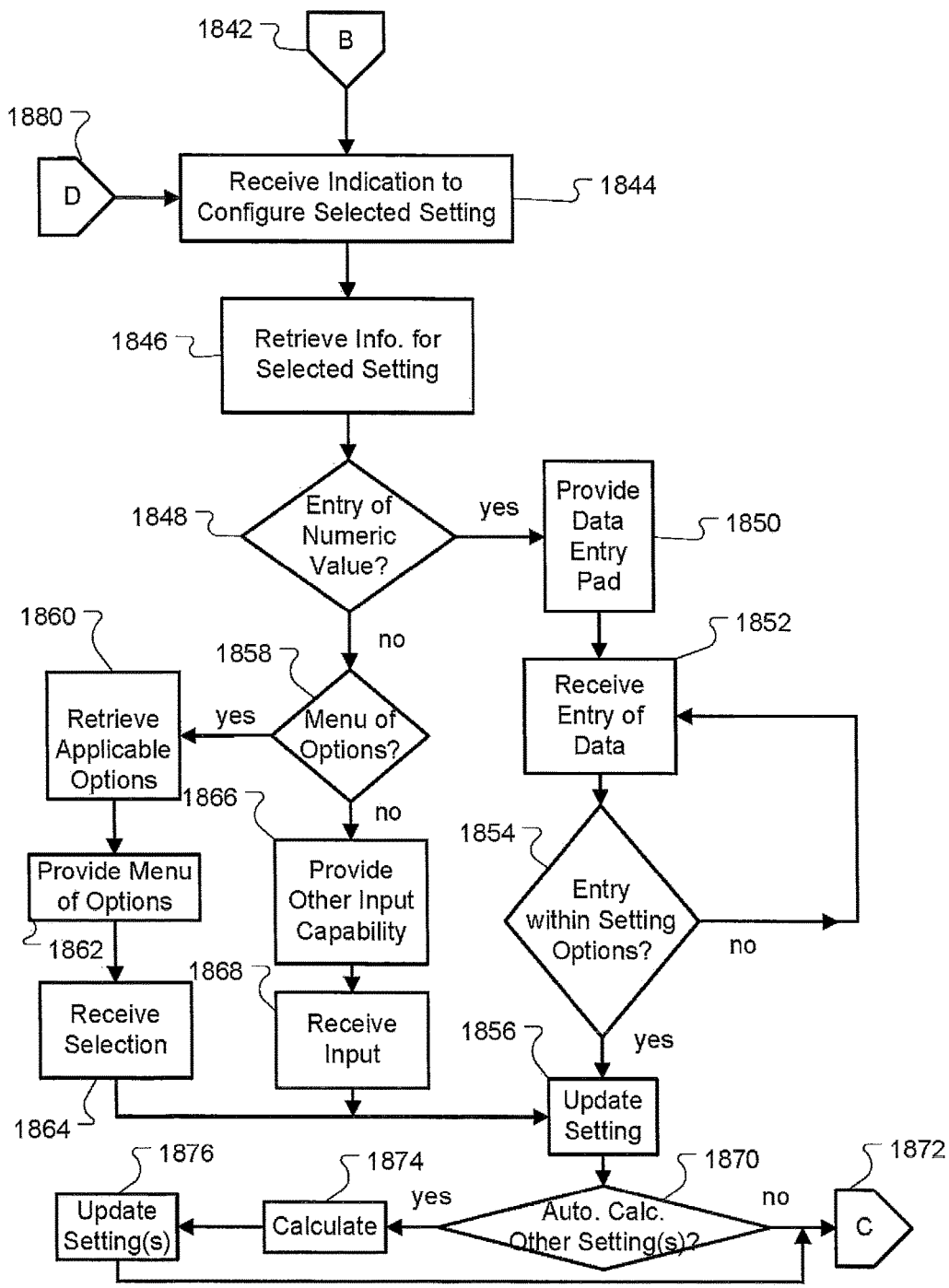

In an embodiment, where a value for a first configured setting is received, another setting may be automatically calculated by the system based on the received first value. In an embodiment, a task may include a pump rate, such as the IC Circulation Rate, that the system automatically calculates based on another pump rate for the task, such as the IC Inlet Rate. In an embodiment, a user or operator may override an automatically calculated pump rate. In another embodiment, a user or operator may not be permitted to override the automatically calculated pump rate. In embodiments, setting options indicate whether it is possible to override an automatically calculated value. As shown in FIG. 18C, after updating a setting 1856 based on receiving an entry of data, for example, the system determines whether to automatically calculate any other settings in query 1870. Where no automatic calculation occurs, process 1800 proceeds NO to off-page reference C 1872, and process 1800 continues to query 1873 of FIG. 18D. Where another setting is automatically calculated based on configuration of the first setting, process 1800 proceeds YES to calculate the value for the second setting 1874 and update the second setting 1876. Process 1800 then proceeds through off-page reference C 1872 to query 1873 of FIG. 18D. In embodiments, query 1870 is optional, in which process 1800 provides for updating the setting operation 1856 and proceeding through off-page reference C 1872 to query 1873 of FIG. 18D.

Returning to query 1848, if it is determined that the selected setting is not associated with a numeric value, process 1800 proceeds NO to query 1858 to determine if a menu, list, or window, for example, of selection options is associated with the selected setting. In an embodiment, such selection options are predetermined or pre-defined. In an embodiment, such selection options comprise text, such as "Wash." In another embodiment, the selection options include a numeric value. If a window or menu of selection options is associated with the selected setting, process 1800 proceeds YES to retrieve the applicable options 1860. The menu or window of options is then provided 1862, and a selection of an option is received 1864. For example, "Wash" is selected 1864 from a menu of options 1862 for the IC Inlet setting, according to an embodiment of the present disclosure. The selected setting is then updated 1856. Process 1800 then proceeds to query 1870 to determine if any other settings are automatically calculated based on the selection received at operation 1864. Where no other settings are automatically calculated based on the received selection at operation 1864, process 1800 proceeds NO through off-page reference C 1872 to query 1873 of FIG. 18D. In embodiments, query 1870 is optional, in which process 1800 provides for updating the setting operation 1856 and proceeding through off-page reference C 1872 to query 1873 of FIG. 18D.

Next, returning to query 1858, where a menu or window of selection options is not associated with the selected setting, process 1800 proceeds to operation 1866 for providing another input/selection capability, such as a field, radio button, control, checkbox, etc., according to embodiments of the present disclosure. Input is received at operation 1868, and the selected setting is updated 1856. Process 1800 then proceeds to query 1870. Where no other settings are automatically calculated based on the received selection at operation 1864, process 1800 proceeds NO through off-page reference C 1872 to query 1873 of FIG. 18D. In embodiments, query 1870 is optional, in which process 1800 provides for updating the setting operation 1856 and proceeding through off-page reference C 1872 to query 1873 of FIG. 18D.

Figure 18D:
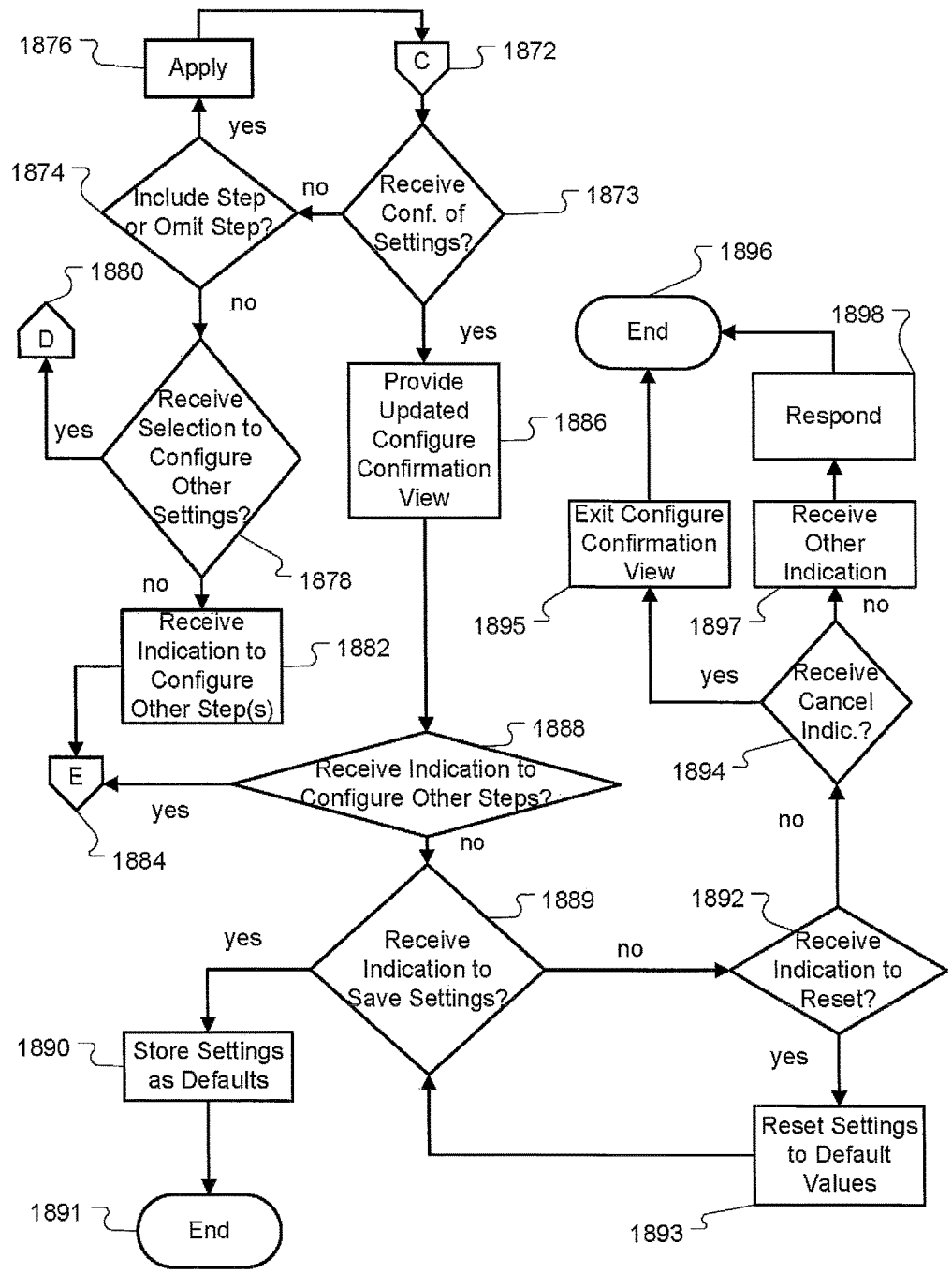

At query 1873 of FIG. 18D, it is determined whether a confirmation of the configured setting(s) is received. If no confirmation is received, process 1800 proceeds NO to determine whether a selection to include or omit a step is received 1874. If such a selection is received, the appropriate application of the request occurs 1876, and process 1800 then proceeds to query 1873. If no steps are included or omitted at query 1874, process 1800 proceeds NO to query 1878 for determining whether a selection to configure other settings 1878 is received. If other settings are desired to be configured, process 1800 proceeds YES to off-page reference D 1880, in which process 1800 continues to operation 1844 of FIG. 18C. If no selection is received to configure another setting(s), process 1800 proceeds NO to receive an indication to configure another step(s) of the selected task 1882, such as by selecting a button(s) with the applicable functionality, for example. Process 1800 then proceeds through off-page reference E 1884 to operation 1830 of FIG. 18B. Returning to query 1873, if a confirmation of the configuration is received, process 1800 proceeds YES to provide an updated configure confirmation view 1886, in which the settings, including any configured settings, are provided in the updated view 1886. In an embodiment, the configure confirmation view comprises a table format. Query 1888 next determines whether an indication is received in the table view of the settings to configure any other step(s). If a selection for configuring other step(s) is received, process 1800 proceeds YES through off-page reference E 1884 to operation 1830 of FIG. 18B. If no other configuration of steps is desired, process 1800 proceeds NO to query 1889 to determine whether the configurations are to be stored. If an indication to save the configuration(s) is received, process 1800 proceeds YES to store the settings as defaults 1890, in which the previous default settings, including previously configured default settings, if any, are replaced with the newly configured settings. In an embodiment, such configurations are stored through the use of Extensible Markup Language (XML) files. However, any type of storage capabilities understood by those of skill in the art may be used without departing from the spirit and scope of the present disclosure. Process 1800 then terminates at END operation 1891, in which the configure task settings UI is closed, according to embodiments.

Returning to query 1889, if an indication to store the configurations is not received, process 1800 proceeds NO to receive an indication to reset the settings query 1892, in which it is determined whether a selection to reset the settings to the factory default settings is received 1892. If a selection to reset the settings is received, process 1800 proceeds YES to reset the settings to the default values 1893. Process 1800 then continues to query 1889. If no indication to reset at query 1892 is received, process 1800 proceeds NO to query 1894 to determine whether an indication to cancel the configuration is received. If an indication to cancel is received, process 1800 proceeds YES to exit the configure confirmation table view 1895, and process 1800 then terminates at END operation 1896. If no indication to cancel is received at query 1894, process 1800 proceeds NO to receive another indication 1897, such as an indication to move to another screen, for example, through the selection of a button, control, or other icon, according to an embodiment. The system responds 1898 to the selection of the other indication 1897, as applicable, e.g., moving to another screen in an embodiment selecting the next screen, for example, and process 1800 terminates at END operation 1896.

While FIGS. 18A, 18B, 18C, and 18D depict example process 1800 for configuring a pre-defined task, FIGS. 19A, 19B, 19C, and 19D illustrate example operational steps 1900 for configuring a custom or user-defined task, in accordance with embodiments of the present disclosure. Start operation 1902 is initiated, and process 1900 proceeds to operation 1904 for receiving a selection to configure. Configuration selection options, including GUI elements to select to configure system settings, display settings, task settings, etc., are provided 1906. A selection to configure the default settings for tasks is then received 1908. The types of tasks for selection are then provided 1910, and a selection of a custom task, e.g., Custom Task 1, is received 1912. The default settings for the selected custom task are then retrieved 1914 from storage, for example. The default settings are then provided in a configure confirmation view 1916, in accordance with an embodiment. In further embodiments, the configure confirmation view comprises a table format for listing the settings. Next, query 1918 determines whether a selection is received to add a step to the custom task. In an embodiment, a custom task includes a single step by default. If a selection to add a step is received, process 1900 proceeds YES to add the step and retrieve the default settings for the added step 1920. Process 1900 then continues to operation 1916 for providing the default settings in the configure confirmation table view, according to embodiments. If no step is desired to be added at query 1918, process 1900 proceeds NO through off-page reference A 1922 to query 1924 of FIG. 19B. While query 1918 determines whether a step is to be added, other embodiments provide for a user or operator to select to add a step at a later time, for example, in another UI, e.g., in the diagram view or window for configuring, etc. Embodiments provide for numerous types of windows to provide the functionality to add a step(s). Query 1918 is offered as an example for determining whether to add a step in process 1900. As noted, other embodiments provide for a step(s) to be added before or after query 1918, etc.

Figure 19A:
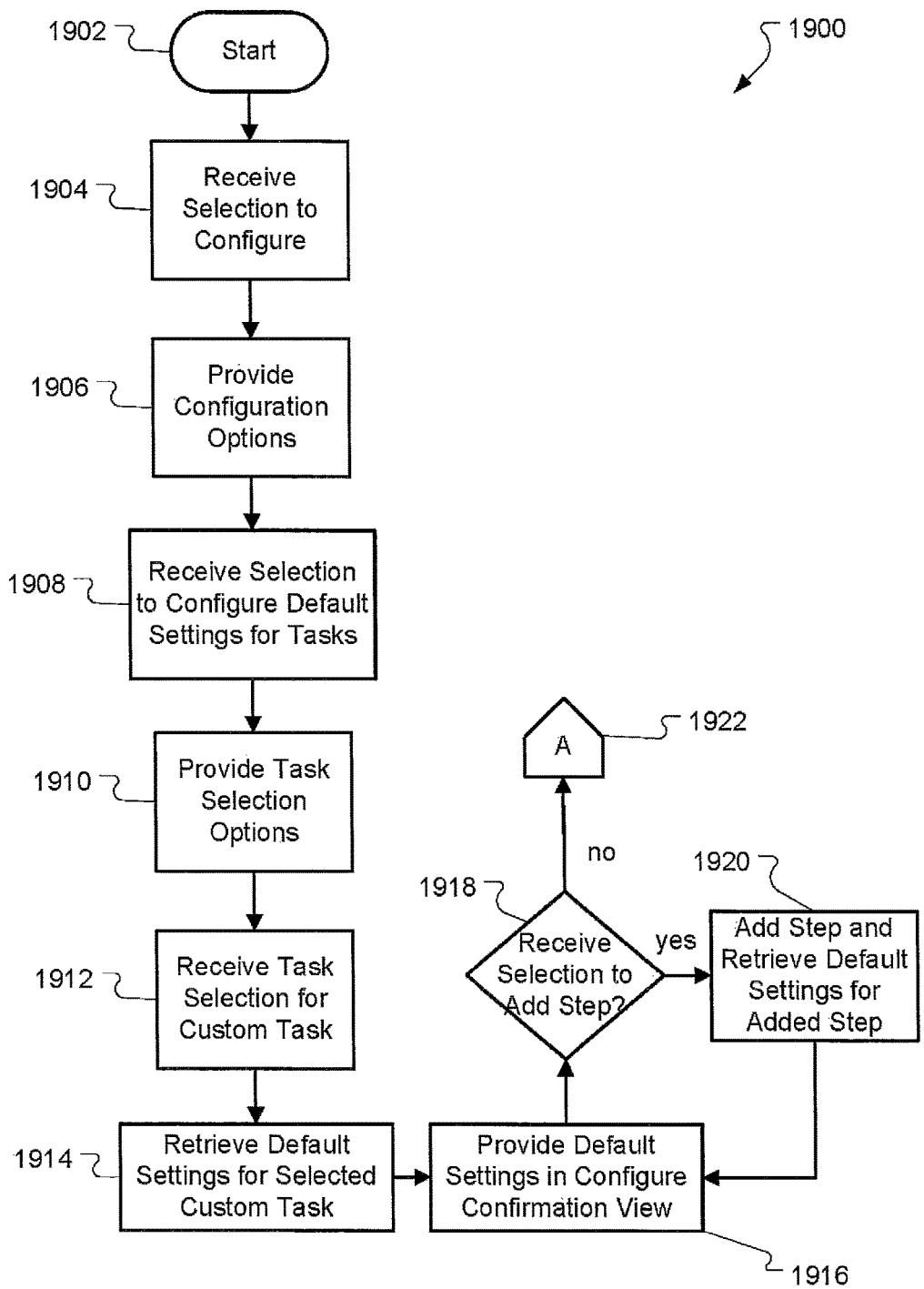
FIGS. 19A, 19B, 19C, and 19D depict a flow diagram illustrating the operational characteristics of a process for configuring the settings of a custom or user-defined task used with the cell expansion system in accordance with embodiments of the present disclosure.
Figure 19B:
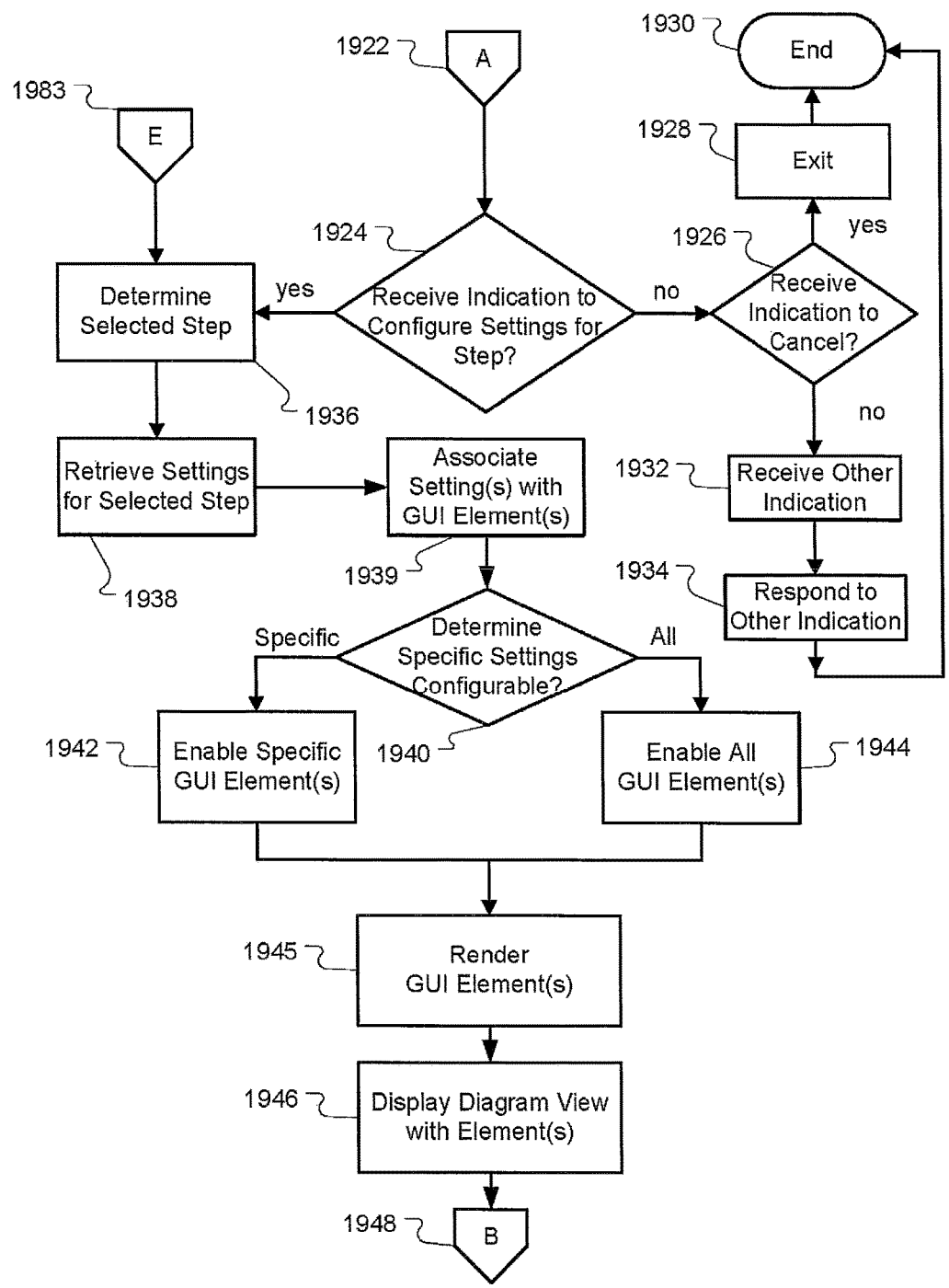

As process 1900 continues through off-page reference A 1922 to query 1924 of FIG. 19B, it is determined whether an indication is received to configure the settings for a step or process associated with the selected task and displayed in the configure confirmation UI. If a selection to configure the settings for a step is not received, process 1900 proceeds NO to query 1926, in which it is determined whether a selection to cancel the configuration is received. If an indication to cancel is received, process 1900 proceeds YES to close the configuration window 1928 and exit the configuration screen. Process 1900 then terminates at END operation 1930, in which a home screen of the cell expansion system may appear, according to embodiments. If an indication to cancel is not received at query 1926, process 1900 proceeds NO to receive another indication 1932, such as to switch to another screen through a selection of a next screen button, control, or icon, for example. The indication received is responded to 1934, and process 1900 then terminates at END operation 1930.

Returning to query 1924, if an indication to configure settings for a step is received, process 1900 proceeds YES to determine the step selected 1936, and the setting(s) associated with the selected step are retrieved 1938. The retrieved setting(s) are associated with GUI element(s) 1939. For example, the system associates 1939 a setting, e.g., a first setting, with a GUI element, e.g., a first GUI element. The GUI element may be further associated with data associated with the setting, e.g., default data, according to embodiments. For example, a GUI element may be associated with a numeric value, a media type, e.g., Cells, Reagent, etc., depending on the associated setting type. In embodiments, a first GUI element displayed in the diagram view shows the default data associated with the first GUI element, for example.

Query 1940 next determines if specific settings are available for configuration, e.g., a determination is made as to whether specific settings are configurable, in which the configurable settings are identified by the system. As discussed above, settings may be configured only for those settings that are available for configuration, according to embodiments of the present disclosure. If a setting cannot be configured, the button, or other GUI element, associated with the setting is not enabled for selection, in accordance with embodiments. For example, enabling the first GUI element for selection includes showing that the first GUI element is capable of selection by the use of one or more visual indicia showing such selection capabilities. In embodiments, a GUI element that is not enabled is a first color, while a GUI element that is enabled is a second color. A visual indicia change comprising a color change is offered for purposes of illustration. Numerous types of visual indicia changes may be used to designate a GUI element as being enabled without departing from the spirit and scope of the present disclosure. For example, text may be used to show whether a GUI element is enabled or not enabled, such as by labels designating "Enabled" or "Not Enabled," for example. Further embodiments also include using any type of indicia change without departing from the spirit and scope of the present disclosure, in which such indicia changes are not limited to visual indicia changes.

Returning to query 1940, in response to determining that all settings associated with the selected step are configurable, process 1900 proceeds "All" to enable for selection all GUI element(s) associated with the setting(s) 1944. On the other hand, in response to determining that only specific settings are available for configuration, process 1900 branches "Specific" at query 1940 to enable specific GUI elements for selection 1942. A diagram view or window showing the enabled and/or non-enabled settings is then provided, in which such providing includes: rendering the GUI element(s) 1945 and displaying the diagram view or window with the enabled and/or non-enabled GUI element(s) 1946. Process 1900 then proceeds through off-page reference B 1948 to operation 1950 of FIG. 19C.

Figure 19C:
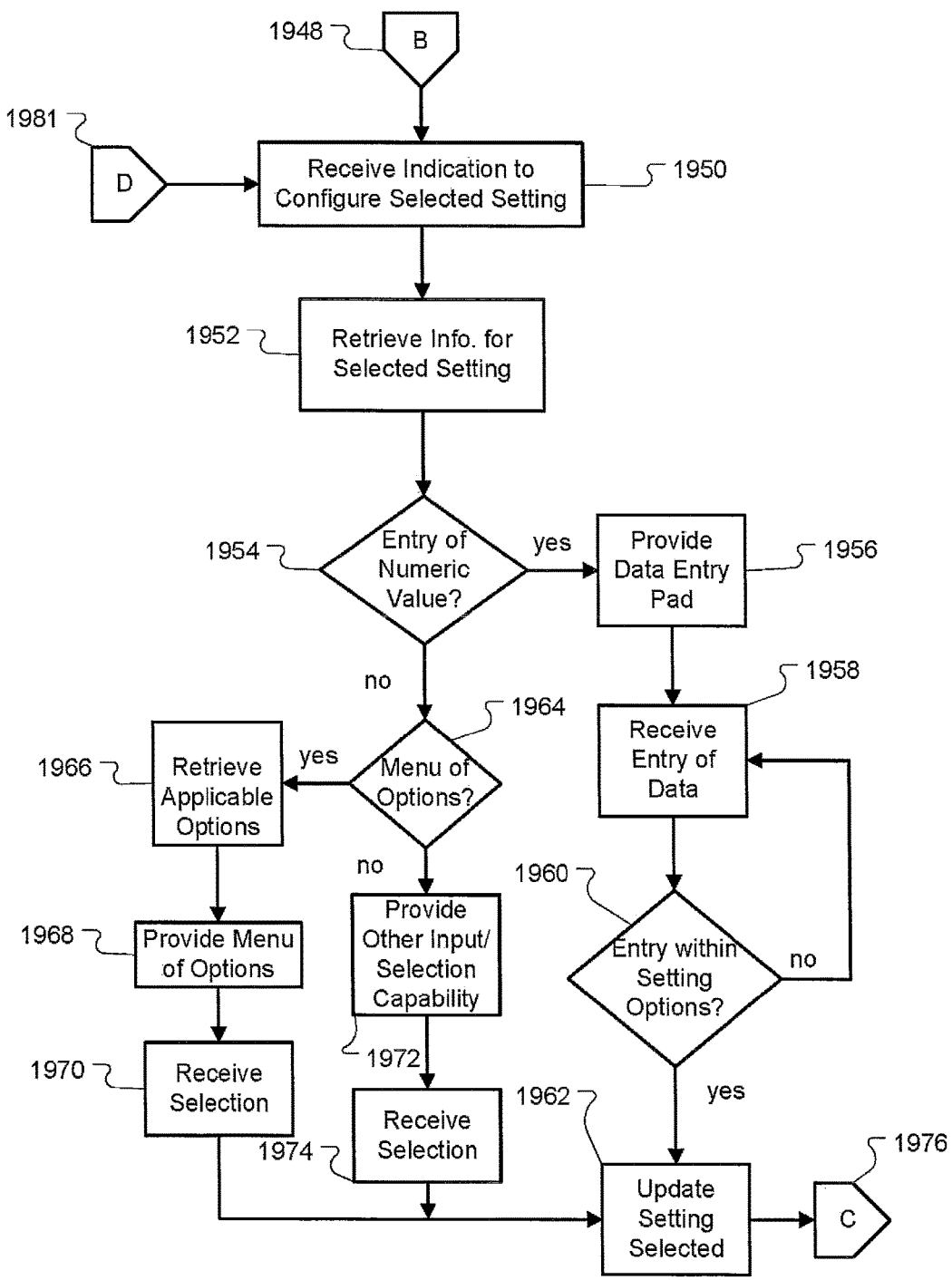

At operation 1950 of FIG. 19C, an indication to configure a selected setting is received, such as by receiving a selection of a GUI element associated with the selected setting. Information related to the selected setting is then retrieved 1952, including information such as whether the setting is associated with a numeric value, for example. Query 1954 determines whether the setting is associated with entry of a numeric value. If entry of a numeric value is associated with the setting, process 1900 proceeds YES to provide data entry pad or window 1956 for receiving an entry of data 1958. In embodiments, it may be determined whether the numeric value entered is within the available setting options 1960, for example. If the entry is not within the acceptable range, process 1900 proceeds to operation 1958 to receive another data entry. If the entry is within the available range 1960, process 1900 proceeds YES to update the setting 1962 according to the received value. In an embodiment, query 1960 is optional, and process 1900 proceeds to update the setting 1962 according to the received value.

Further, in updating the selected setting 1962, or after such updating, for example, embodiments may provide for a second setting to be automatically calculated based on the value received for the first setting. In an embodiment, such calculations occur automatically. In another embodiment, such calculations are optional. As an example, a task may include a pump rate, such as the IC Circulation Rate, that the system automatically calculates based on another pump rate for the task, such as the IC Inlet Rate. A user or operator may override an automatically calculated pump rate, according to an embodiment of the present disclosure. In another embodiment, a user or operator may not be permitted to override the automatically calculated pump rate. In embodiments, setting options indicate whether an automatically calculated value may be overridden. Process 1900 then proceeds through off-page reference C 1976 to query 1977 of FIG. 19D.

Returning to query 1954, if it is determined that the selected setting is not associated with a numeric value, process 1900 proceeds NO to query 1964 to determine if a menu, list, or window, for example, of selection options is associated with the selected setting. If a window, list, or menu, for example, of selection options is associated with the selected setting, process 1900 proceeds YES to retrieve the applicable options 1966. In an embodiment, such selection options are predetermined or pre-defined. The menu, list, or window of selection options is then provided 1968, and a selection of an option is received 1970. For example, "Wash" is selected for the IC Inlet setting, according to an embodiment of the present disclosure. In another embodiment, a numeric value is selected, for example. The selected setting is then updated 1962. In an embodiment, any automatically calculated settings (based on any received data for the selected setting, for example) are also updated at update setting operation 1962. In another embodiment, any automatically calculated settings are updated after update setting operation 1962. Process 1900 next proceeds through off-page reference C 1976 to query 1977 of FIG. 18D.

Returning to query 1964, where a menu, list, or window, for example, of selection options is not associated with the selected setting, process 1900 proceeds to operation 1972 for providing another input/selection capability, such as a field, radio button, control, checkbox, etc., according to embodiments of the present disclosure. Input or a selection is received at operation 1974, and the selected setting is updated 1962. In an embodiment, any automatically calculated settings (based on any received data for the selected setting, for example) are also updated at update setting operation 1962. In another embodiment, any automatically calculated settings are updated after update setting operation 1962. Process 1900 then proceeds through off-page reference C 1976 to query 1977 of FIG. 18D.

Figure 19D:
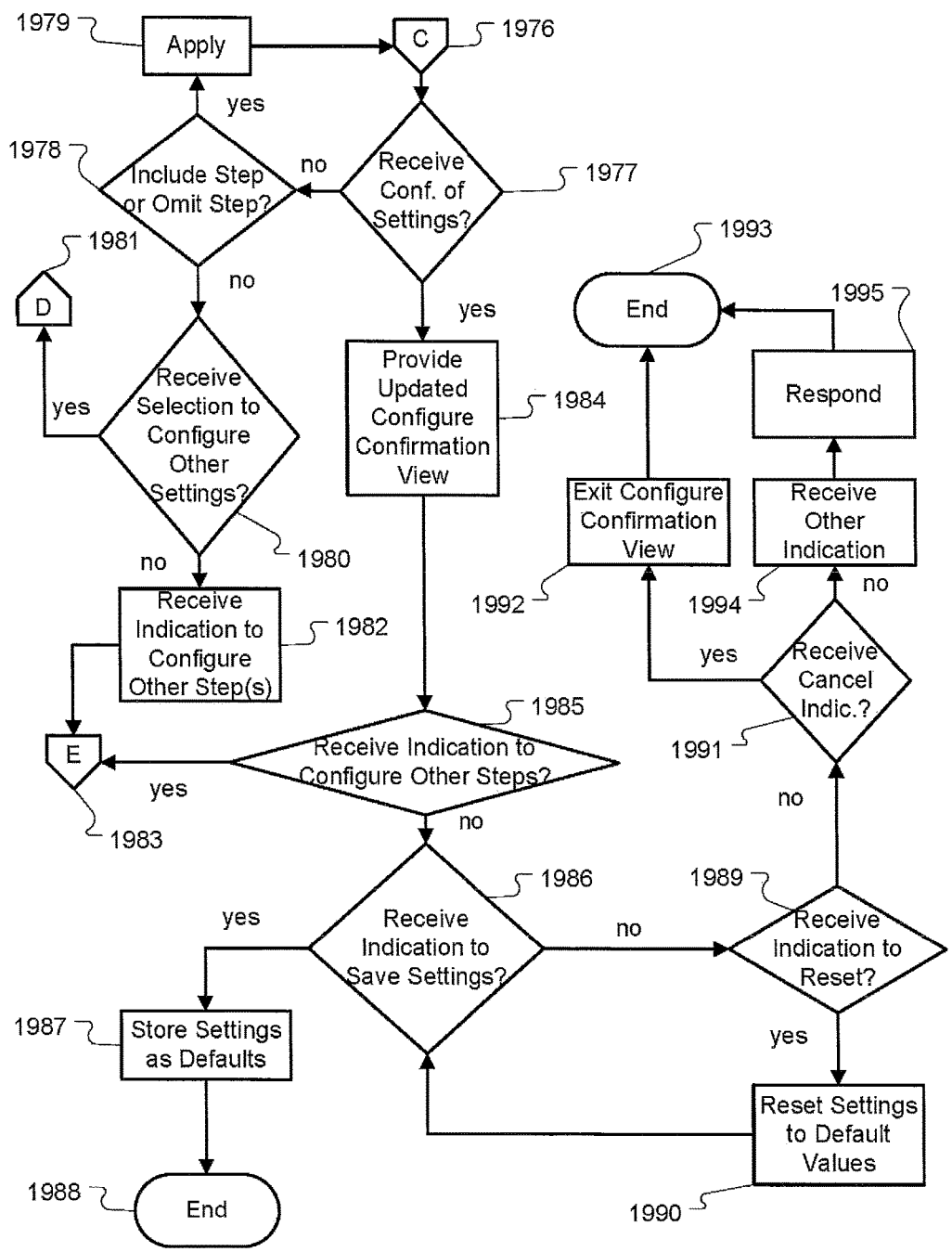

At query 1977 of FIG. 19D, it is determined whether a confirmation of the configured setting(s) is received. If no confirmation is received, process 1900 proceeds NO to determine whether a selection to include or omit a step is received 1978. If such a selection is received, the appropriate application of the request occurs 1979, and process 1900 then proceeds to query 1977. If no steps are included or omitted at query 1978, process 1900 proceeds NO to query 1980 for determining whether a selection to configure other settings is received. If other settings are desired to be configured, process 1900 proceeds YES to off-page reference D 1981, in which process 1900 continues to operation 1950 of FIG. 19C. If no selection is received to configure another setting(s), process 1900 proceeds NO to receive an indication to configure another step(s) of the selected task 1982. Process 1900 then proceeds through off-page reference E 1983 to operation 1936 of FIG. 19B. Returning to query 1977, if a confirmation of the configuration is received, process 1900 proceeds YES to provide an updated configure confirmation view 1984, in which the settings, including any configured settings, are provided in the updated view 1984. In embodiments, the updated configure confirmation view comprises a table format. Query 1985 next determines whether an indication is received in the updated configure confirmation view of the settings to configure any other step(s). If a selection for configuring other step(s) is received, process 1900 proceeds YES through off-page reference E 1983 to operation 1936 of FIG. 19B. If no other configuration of steps is desired, process 1900 proceeds NO to query 1986 to determine whether the configurations are to be stored. If an indication to save the configuration(s) is received, process 1900 proceeds YES to store the settings as defaults 1987, in which the previous default settings, including previously configured default settings, if any, are replaced with the newly configured settings. Process 1900 then terminates at END operation 1988, in which the configure task settings UI is closed, according to embodiments.

Returning to query 1986, if an indication to store the configurations is not received, process 1900 proceeds NO to receive an indication to reset the settings query 1989, in which it is determined whether a selection to reset the settings to the factory default settings is received 1989. If a selection to reset the settings is received, process 1900 proceeds YES to reset the settings to the default values 1990. Process 1900 then continues to query 1986. If no indication to reset is received, process 1900 proceeds NO to query 1991 to determine whether an indication to cancel the configuration is received. If an indication to cancel is received, process 1900 proceeds YES to exit the configure confirmation view 1992, and process 1900 then terminates at END operation 1993. If no indication to cancel is received at query 1991, process 1900 proceeds NO to receive another indication 1994, such as an indication to move to another screen through the use of a button, control, or icon, according to an embodiment. The system responds 1995 to the selection of the other indication 1994, as applicable, e.g., moving to another screen in an embodiment selecting the next screen, for example, and process 1900 terminates at END operation 1993.

Figure 20A:
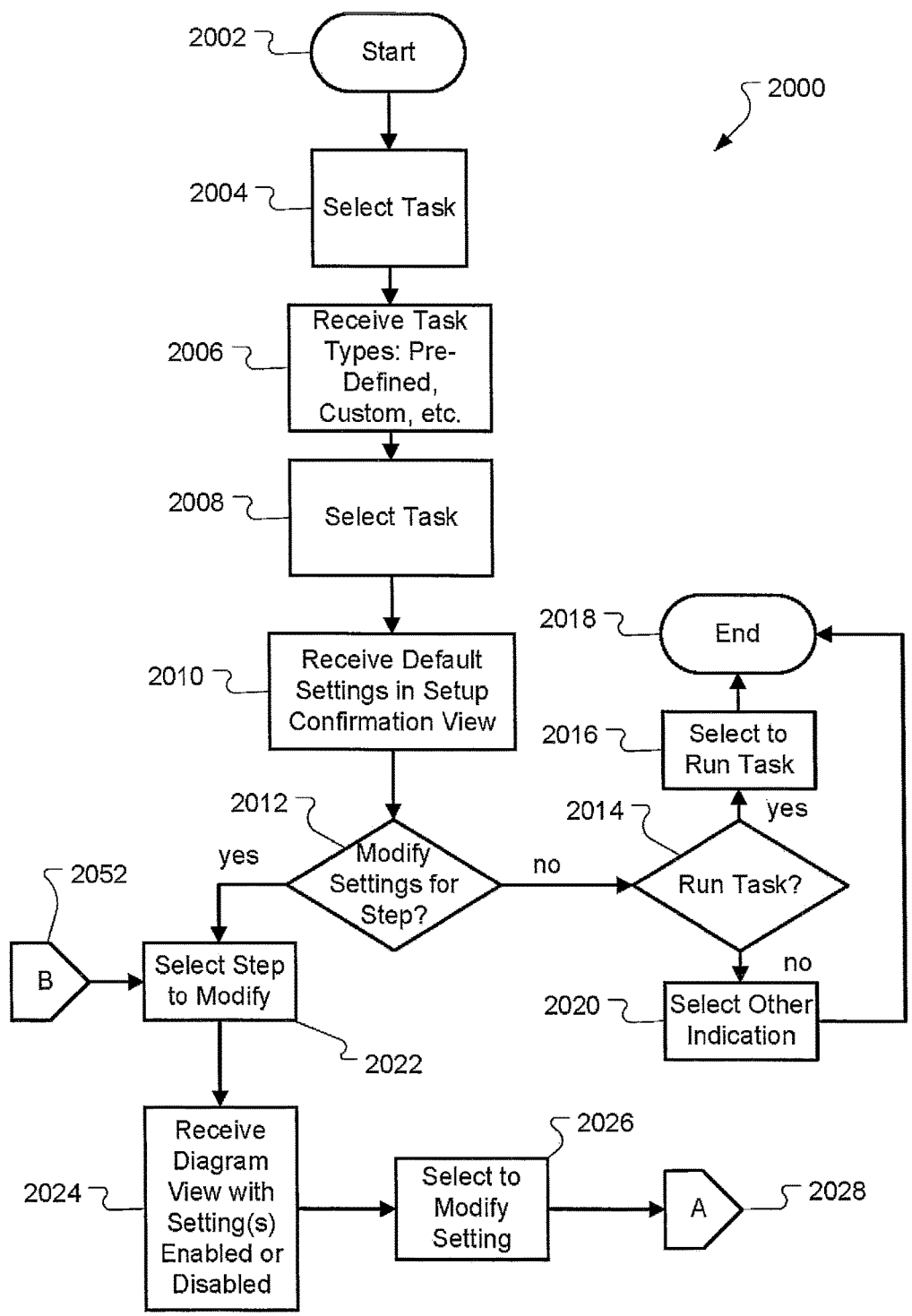
FIGS. 20A and 20B illustrate a flow diagram depicting the operational characteristics of a process for modifying a protocol, from the perspective of a user or operator, for example, for use with the cell expansion system in accordance with embodiments of the present disclosure.
Figure 20B:
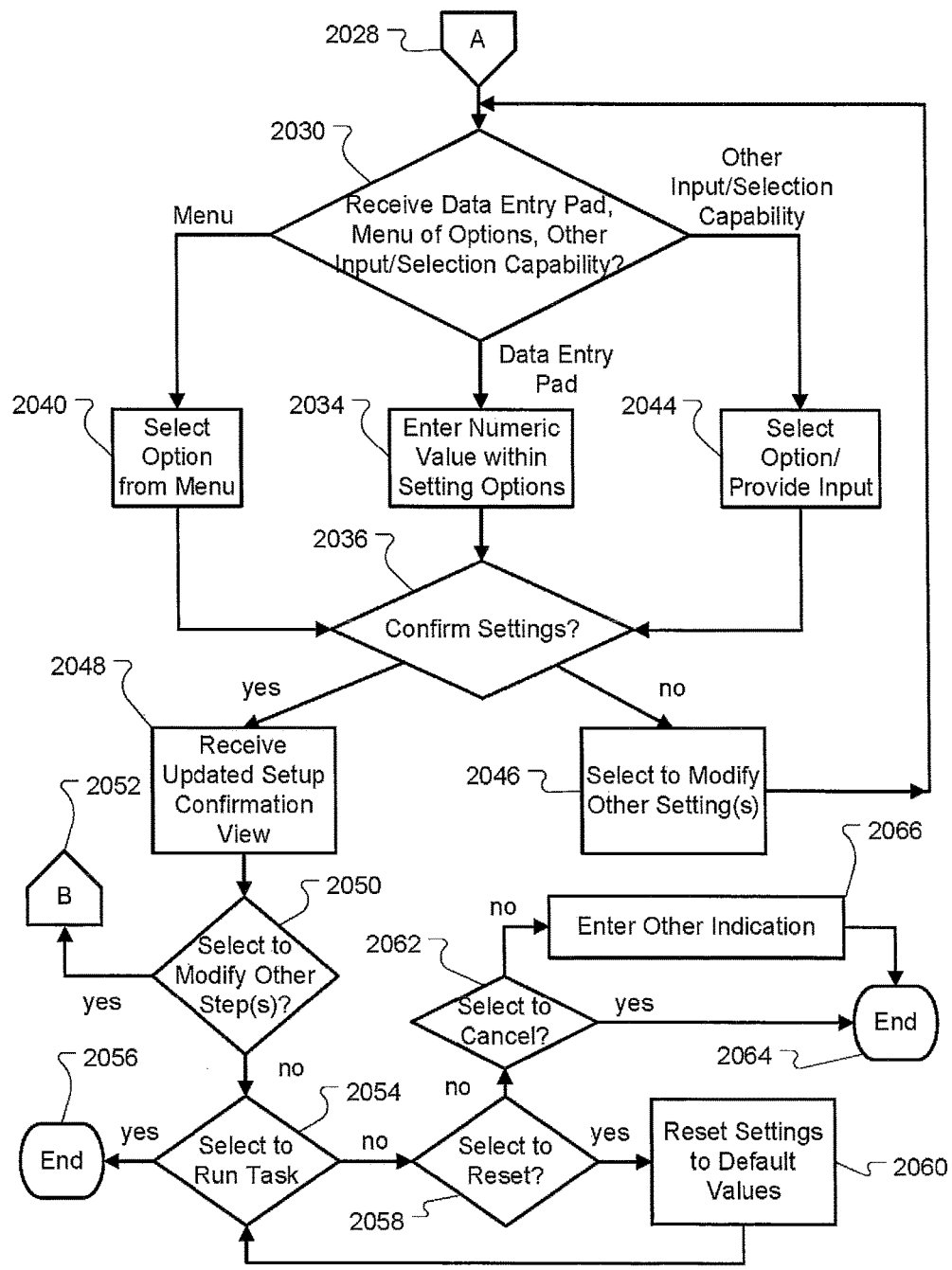

While FIGS. 19A, 19B, 19C, and 19D depict example steps for receiving, such as by the system, for example, configuration settings, FIGS. 20A and 20B illustrate example operational steps 2000 for modifying, from the perspective of a user or operator, device, program, etc., for example, a protocol or task for use with the system, in accordance with embodiments of the present disclosure. Start operation 2002 is initiated, and process 2000 proceeds to select a task or protocol 2004 for use with the cell expansion system. The types of tasks or protocols are received 2006, including pre-defined and/or custom task types, in accordance with embodiments disclosed herein. A task type is then selected 2008, and the default settings for the selected task are received 2010. In an embodiment, the default settings for the selected task are displayed in a setup confirmation view 2010, in which the setup confirmation view comprises a table view in embodiments. A determination 2012 is made as to whether to modify a process, or step, for the selected task or protocol. If it is not desired to modify a setting for a process or step, process 2000 proceeds NO to query 2014 to determine if the selected task or protocol should be executed. If it is desired to run the task or protocol, process 2000 proceeds YES to select to execute the task 2016. In an embodiment, an indication to execute the task comprises selecting a "Start" button or other UI element indicating to run the task. The task or protocol is then executed, and process 2000 terminates at END operation 2018. If it is not desired to execute the task, another indication is selected 2020, such as an indication to cancel, for example, in which the current view or window is closed, and a home screen appears, according to an embodiment. Process 2000 then terminates at END operation 2018.

Returning to query 2012, if it is desired to modify a setting(s) for a process, or step, process 2000 proceeds YES to select the step to modify 2022. In an embodiment, selecting the step to modify comprises selecting a "Modify" button or other type of GUI element designating modification functionalities for a particular step in the setup view, in which the setup view, in embodiments, comprises a table format. Process 2000 then proceeds to receive a diagram view or window with those settings capable of being modified shown as enabled GUID elements in the diagram view or window 2024. A selection of an enabled GUI element associated with the desired setting to modify is made 2026, and process 2000 then proceeds through off-page reference A 2028 to query 2030 of FIG. 20B.

At query 2030 of FIG. 20B, it is determined if a data entry pad or window, a menu, list, or window, for example, of selection options, or another input/selection capability is received. If a data entry pad is received, process 2000 proceeds to operation 2034, in which a numeric value is entered. In an embodiment, the numeric value entered is within setting options for the associated setting. In another embodiment, the numeric value entered is not within the setting options for the associated setting, and another numeric value or other input data is then provided. Next, process 2000 proceeds to query 2036 to determine if the settings can be confirmed as those that are desired.

Returning to query 2030, if a menu, list, or window, for example, of selection options is received, process 2000 proceeds to select an option from the menu or window 2040. Next, process 2000 proceeds to query 2036 to determine if the settings can be confirmed as those that are desired. If, at query 2030, another input/selection capability is received, including means to provide data or make a selection through means other than a data entry pad/window or a menu/window of options, process 2000 proceeds to select an option or provide input 2044. Next, process 2000 proceeds to query 2036 to determine if the settings can be confirmed as those that are desired.

If the settings are not confirmed, process 2000 proceeds NO, in which another setting(s) is selected for modification 2046, and process 2000 then continues to query 2030. If, at query 2036, the modified settings are confirmed, process 2000 proceeds YES to receive an updated setup confirmation view including the modified setting(s) 2048. In an embodiment, the updated setup confirmation view comprises data for the settings in a table format. In the setup confirmation view, a selection may be made to select another step(s) to modify 2050. If such a selection is made, process 2000 proceeds YES through off-page reference B 2052 to operation 2022 of FIG. 20A. If it is not desired to modify any other step(s), process 2000 proceeds to query 2054 to determine whether to select to execute the task. If it is desired to execute the task 2054, the selection to run the protocol is made. The system then performs the selected protocol, and process 2000 terminates at END operation 2056. If a selection to execute the task is not made at query 2054, process 2000 proceeds NO to query 2058 to select to reset the modified setting(s) to the factory default settings. If it is desired to reset the setting(s), process 2000 proceeds YES to select to reset the settings to the default values 2060. If it is not desired to reset the settings, process 2000 proceeds NO to query 2062 to determine whether to cancel the modifying of any setting(s). If it is desired to cancel and exit the current screen, process 2000 proceeds YES to terminate process 2000 at END operation 2064, in which the current screen is closed, according to an embodiment. If it is not desired to cancel, process 2000 proceeds NO to enter another indication 2066, in which entering another indication comprises, for example, selecting a button, control, or icon to switch between the current page and another page. Other types of indications may be made in accordance with other embodiments. Process 2000 then terminates at END operation 2064.

Figure 21:
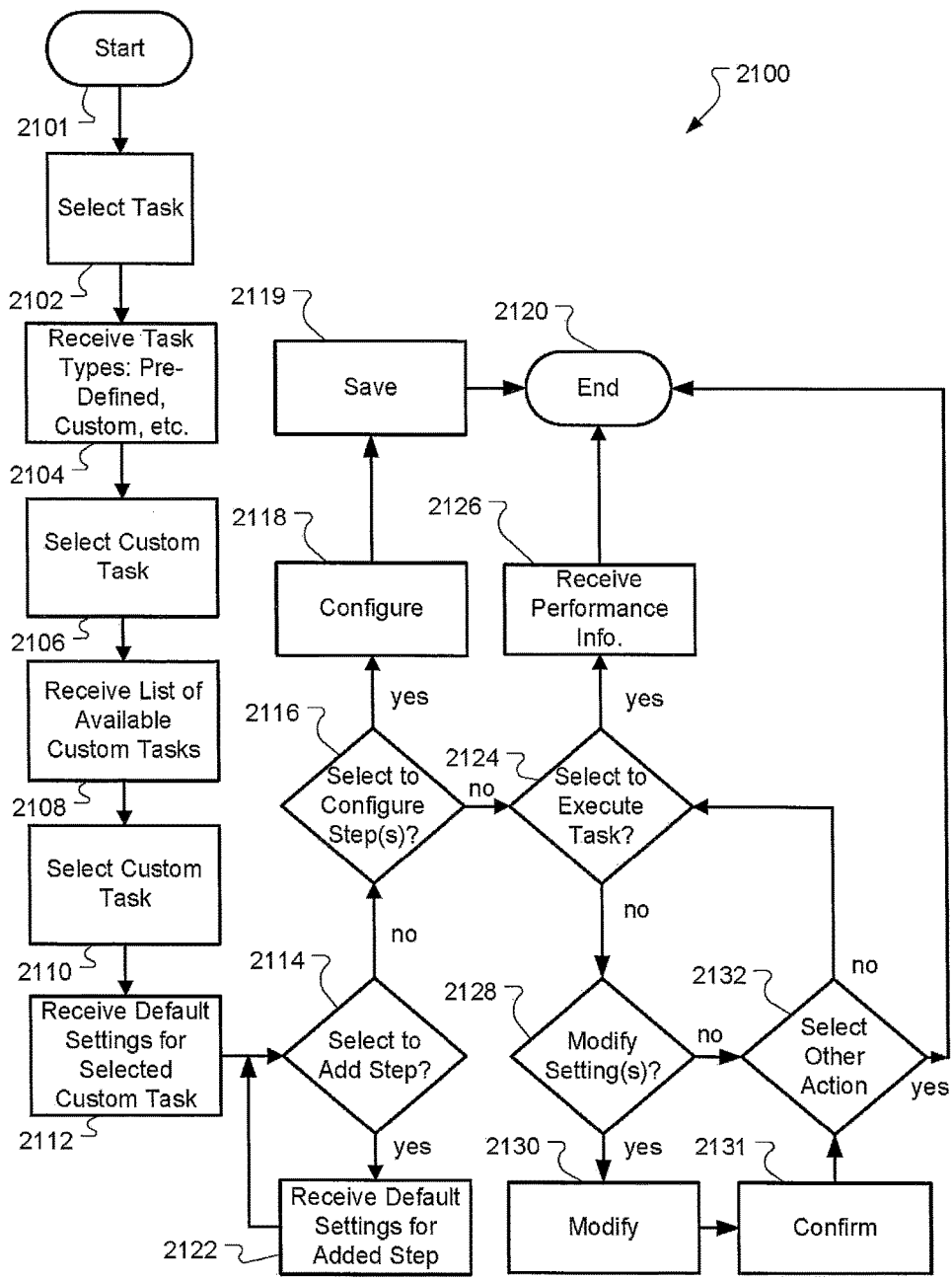
FIG. 21 depicts a flow diagram showing the operational characteristics of a process for creating a custom or user-defined task, from the perspective of a user or operator, for example, for use with the cell expansion system in accordance with embodiments of the present disclosure.

While FIGS. 20A and 20B provide example steps for selecting to modify a setting of a task or protocol, from a user or operator perspective, for example, FIG. 21 depicts example operational steps 2100 for creating a custom or user-defined task from the perspective of a user or operator, according to embodiments of the present disclosure. Start operation 2101 is initiated, and process 2100 proceeds to select a task 2102, in which a "task" button or other GUI element is selected, for example. Protocol or task types are then received 2104, in which such task types include a pre-defined task type and a custom task type, according to embodiments. A custom task is selected 2106, and a list of available custom tasks, e.g., Custom Task 1, Custom Task 2, Custom Task 3, Custom Task 4, Custom Task 5, etc., is received 2108. A specific custom task, e.g., Custom Task 1, is then selected 2110, and default settings for the selected custom task are received 2112. In an embodiment, such default settings include the factory default settings for the selected custom task. In another embodiment, the default settings include settings previously configured and stored for the selected custom task.

Next, query 2114 determines whether it is desired to add a step(s) to the custom task. For example, the following step(s) may be selected: Wash Out Lines, Wash Out Lines Through Membrane, Wash Rapidly, Harvest Cells, Add Bolus, and Custom, according to embodiments. If a selection is made to add a step(s), process 2100 proceeds YES to receive default settings for the selected additional step(s) 2122. Process 2100 then continues to query 2114. If no other steps are desired to be added, process 2100 proceeds NO to determine whether it is desired to select to configure a step(s) 2116. If it is desired to configure a step(s), process 2100 proceeds YES to configure operation 2118, in which a desired configuration is provided for the selected step(s). A selection is made to save the configuration(s) 2119. The system stores the configuration, and process 2100 then terminates at END operation 2120. Returning to query 2116, if it is not desired to configure a step(s), process 2100 proceeds NO to select to execute the task query 2124. If it is desired to execute the task, process 2100 proceeds to operation 2126, in which information regarding the performance of the task is received after task execution. Process 2100 then terminates at END operation 2120. However, if it is not desired to execute the task at query 2124, process 2100 proceeds to query 2128 to determine whether to modify a setting(s) of the custom task. If it is desired to modify a setting(s), process 2100 proceeds YES to provide the desired modification 2130. Following modify operation 2130, process 2100 proceeds to confirm the modification(s) 2131. In embodiments, process 2100 then proceeds to query 2132 to determine if another action, such as to cancel, move to another screen through selection of a button, control, or icon, for example, is selected. If no other action is selected, process 2100 proceeds to query 2124 to determine whether to execute the task. Returning to query 2132, if another action is selected, process 2100 proceeds YES, in which the system responds to the selected action, and process 2100 then terminates at END operation 2120. Further, returning to query 2128, if it is not desired to modify a setting, process 2100 proceeds NO to determine whether to select another action 2132. If no other action is selected, process 2100 proceeds to query 2124 to determine whether to execute the task. On the other hand, if another action is selected at query 2132, process 2100 proceeds YES, in which the system responds to the selected action, and process 2100 then terminates at END operation 2120.

Figure 22A:
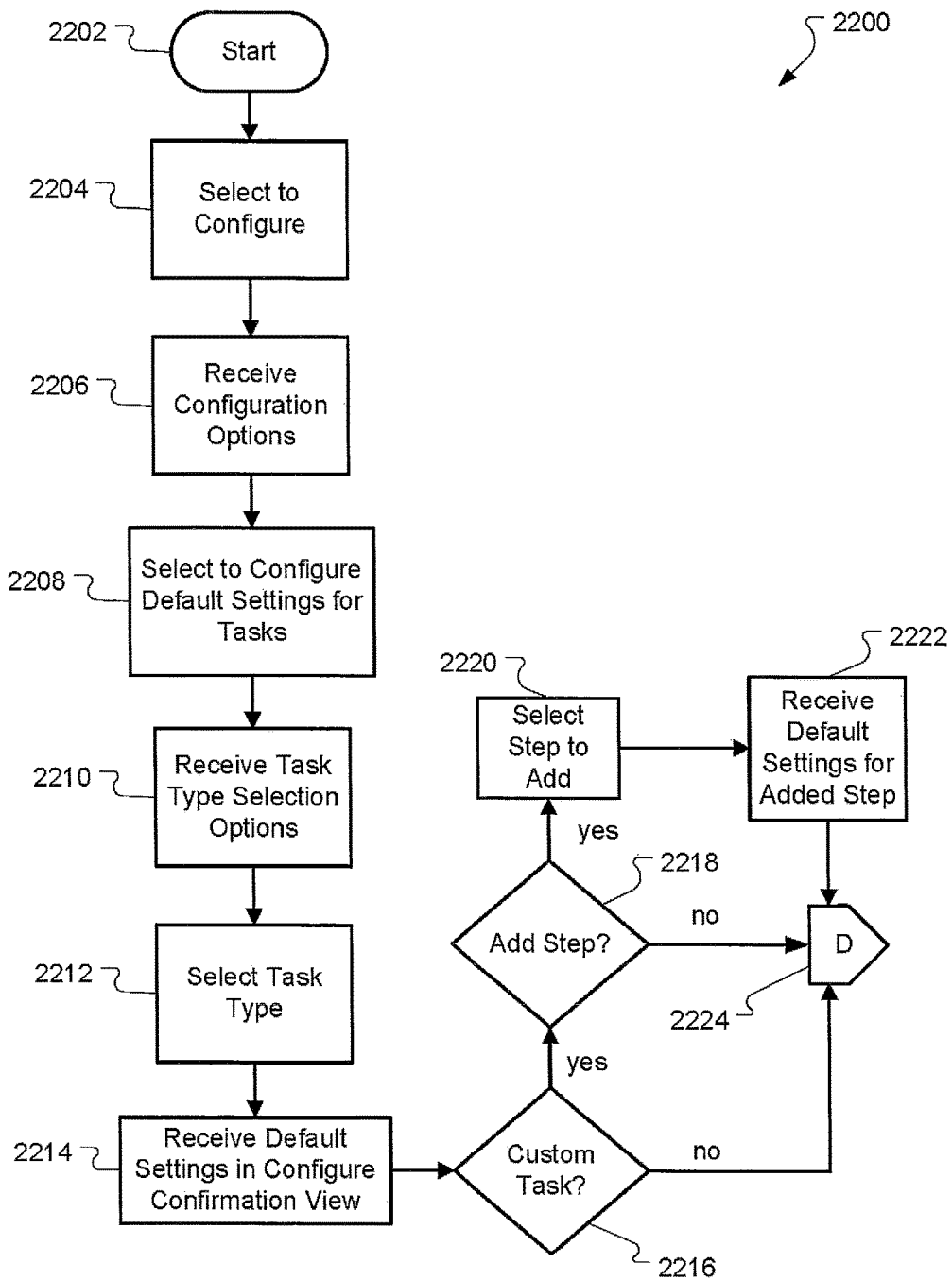
FIGS. 22A, 22B, and 22C illustrate a flow diagram depicting the operational characteristics of a process for configuring a protocol for use with the cell expansion system, from the perspective of a user or operator, for example, in accordance with embodiments of the present disclosure.
Figure 22B:
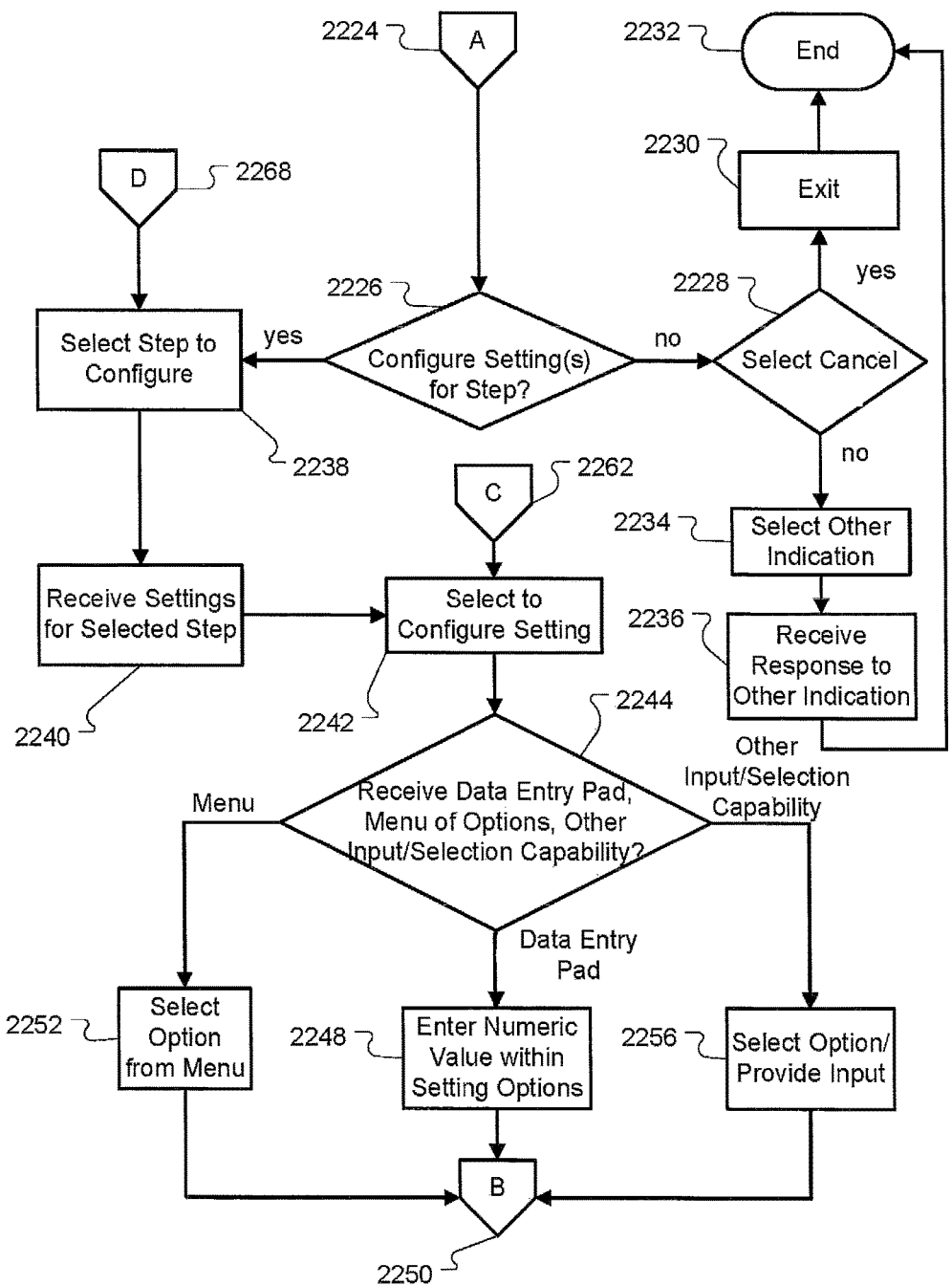
Figure 22C:
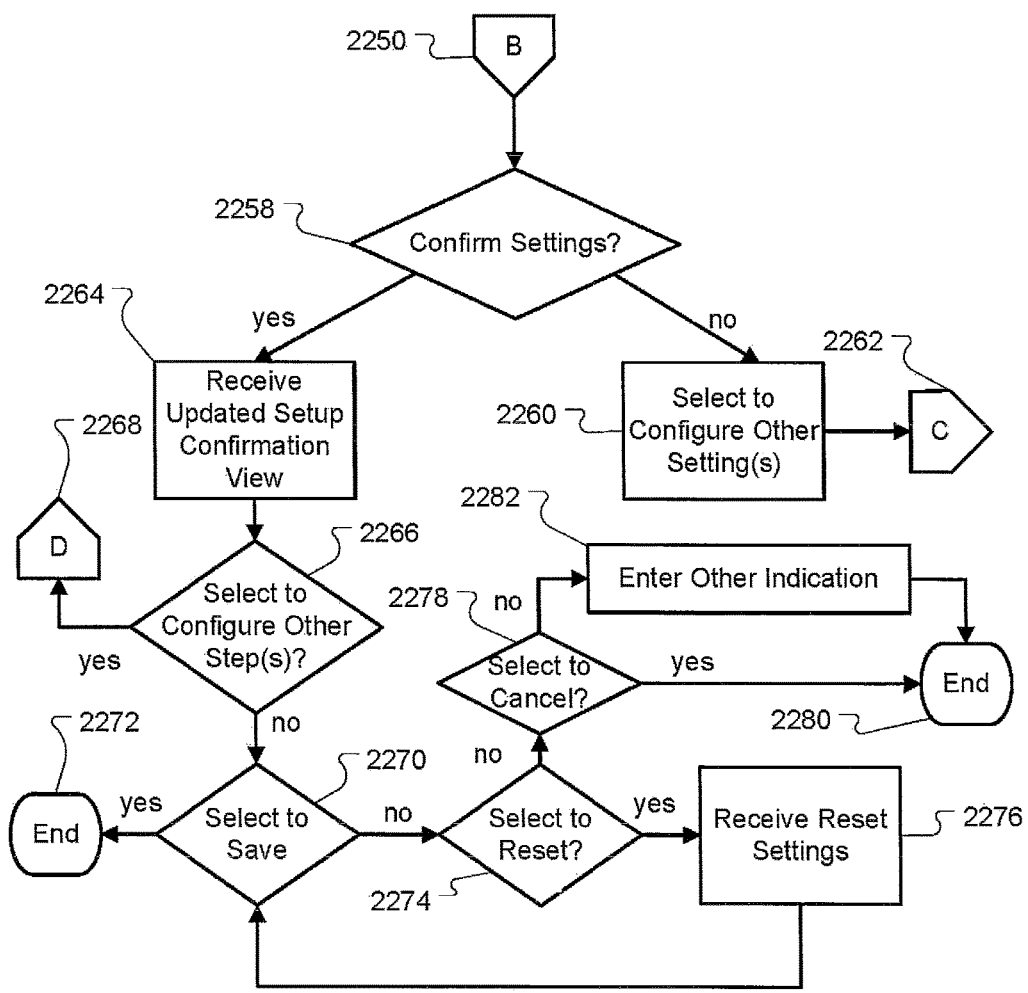

While FIG. 21 provides for creating a custom task, from the perspective of a user or operator, for example, FIGS. 22A, 22B, and 22C illustrate example operational steps 2200 for configuring a task, from the perspective of a user or operator, for example, in accordance with embodiments of the present disclosure. Start operation 2202 is initiated, and process 2200 then proceeds to select to configure operation 2204, in which a selection of a "Configuration" GUI element, e.g., button, may be made according to an embodiment. In response to the configuration selection, configuration options are received 2206, in which such configuration options include system settings, display settings, and/or protocol or task default settings, for example. A selection is then made to configure the default settings for a task 2208, and the task type options are received 2210. A type of task is then selected 2212, and default settings for the selected task type are received 2214. In an embodiment, such default settings are received in a configure confirmation view, in which the configure confirmation view includes settings and data for the settings. According to an embodiment, the settings and associated data in the configure confirmation view are displayed in a table format. Next, it is determined whether the selected task is a custom or user-defined task at query 2216. If a custom task selection is made at operation 2212, process 2200 proceeds YES to query 2218 to determine if a step is desired to be added. If adding a step is desired, process 2200 proceeds YES to select a step to add 2220. Default settings for the added step are then received 2222. Process 2200 the continues through off-page reference A 2224 to query 2226 of FIG. 22B. If it is not desired to add a step to the custom task, process 2200 proceeds NO to off-page reference A 2224, and process 2200 then proceeds to query 2226. Returning to query 2216, if a pre-defined task is selected instead of a custom task at operation 2212, process 2200 proceeds NO through off-page reference A 2224 to query 2226.

Next, at query 2226, it is determined whether to configure a setting(s) of a step. If it is desired to configure a setting(s) of a step, process 2200 proceeds YES to select a step to configure 2238. The settings associated with the selected step are then received 2240. In an embodiment, the setting(s) associated with a step(s) are received in a diagram view of the cell expansion system. A selection to configure a first setting is made 2242. Depending on the type of setting selected to be configured, a data entry pad or window; menu, list, or window, for example, of selection options; or other input/selection capability is received 2244. In an embodiment, selection options in a menu, list, or window, for example, are predetermined or pre-defined. Where a data entry pad or window is received 2246, process 2200 proceeds to enter a numeric value 2248. In an embodiment, the entered numeric value is within the setting options. In another embodiment, the entered numeric value is not within the setting options, e.g., range of acceptable values, and another numeric value is entered 2248. In yet another embodiment, it is optional to determine whether the entered numeric value is within the setting options. Process 2200 then proceeds through off-page reference B 2250 to query 2258 of FIG. 22C. Returning to query 2244, where a menu, list, or window of selection options is received, process 2200 proceeds to select an option from the selection choices 2252. Process 2200 then proceeds through off-page reference B 2250 to query 2258 of FIG. 22C. In another embodiment, if another input or selection capability is received, process 2200 proceeds to select the option or provide input 2256, and process 2200 then proceeds through off-page reference B 2250 to query 2258 of FIG. 22C.

Turning to FIG. 22C, a selection may be made to confirm the configured setting(s) 2258. If no confirmation is made, process 2200 proceeds NO to select to configure other setting(s) 2260. Process 2200 then proceeds through off-page reference C 2262 to operation 2242 of FIG. 22B. If the settings are confirmed at query 2258, process 2200 proceeds YES to receive an updated setup confirmation view 2264. In an embodiment, the updated setup confirmation view 2264 includes the step(s) or process(es) and setting(s) associated with the protocol or task in a table format. Within the setup confirmation screen 2264, if a selection is made to configure another step(s) 2266, process 2200 then proceeds YES through off-page reference D 2268 to operation 2238 of FIG. 22B. If no other steps are selected to configure, process 2200 proceeds NO to query 2270, in which it is determined whether to select to save the configuration(s). If it is indicated to save the configuration(s), process 2200 proceeds YES to END operation 2272, and process 2200 terminates. In an embodiment, process 2200 terminates by storing, by the system, the configuration(s) made, and closing the current screen. If a selection to save is not made at query 2270, process 2200 proceeds NO to query 2274 to determine whether to select to reset a configured setting(s) to the factory default setting(s). If a selection is made to reset the setting(s), process 2200 proceeds YES to receive reset settings 2276. Process 2200 then proceeds to query 2270 to determine whether to save the setting(s). If, at query 2274, a selection is not made to reset the settings, process 2200 proceeds NO to query 2278 to determine if a selection is made to cancel the configuration. If a selection is made to cancel, process 2200 proceeds YES to END operation 2280, in which process 2200 is terminated, such as by closing the current screen, according to an embodiment. If a selection is not made to cancel at query 2278, process 2200 proceeds NO to enter another indication 2282, such as selecting a button, control, or icon to move to another page, for example. In embodiments, the system responds to the selected action, and process 2200 then terminates at END operation 2280.

With respect to the processes illustrated in FIGS. 14A, 14B, 14C, 14D, 15A, 15B, 16, 17, 18A, 18B, 18C, 18D, 19A, 19B, 19C, 19D, 20A, 20B, 21, 22A, 22B, and 22C, the operational steps depicted are offered for purposes of illustration and may be rearranged, combined into other steps, used in parallel with other steps, etc., according to embodiments of the present disclosure. Where queries are depicted as operational steps, such queries may be determined by event-based interactions, polling, and/or other means or processes, according to embodiments. Further, fewer or additional steps may be used in embodiments without departing from the spirit and scope of the present disclosure.

Figure 23:
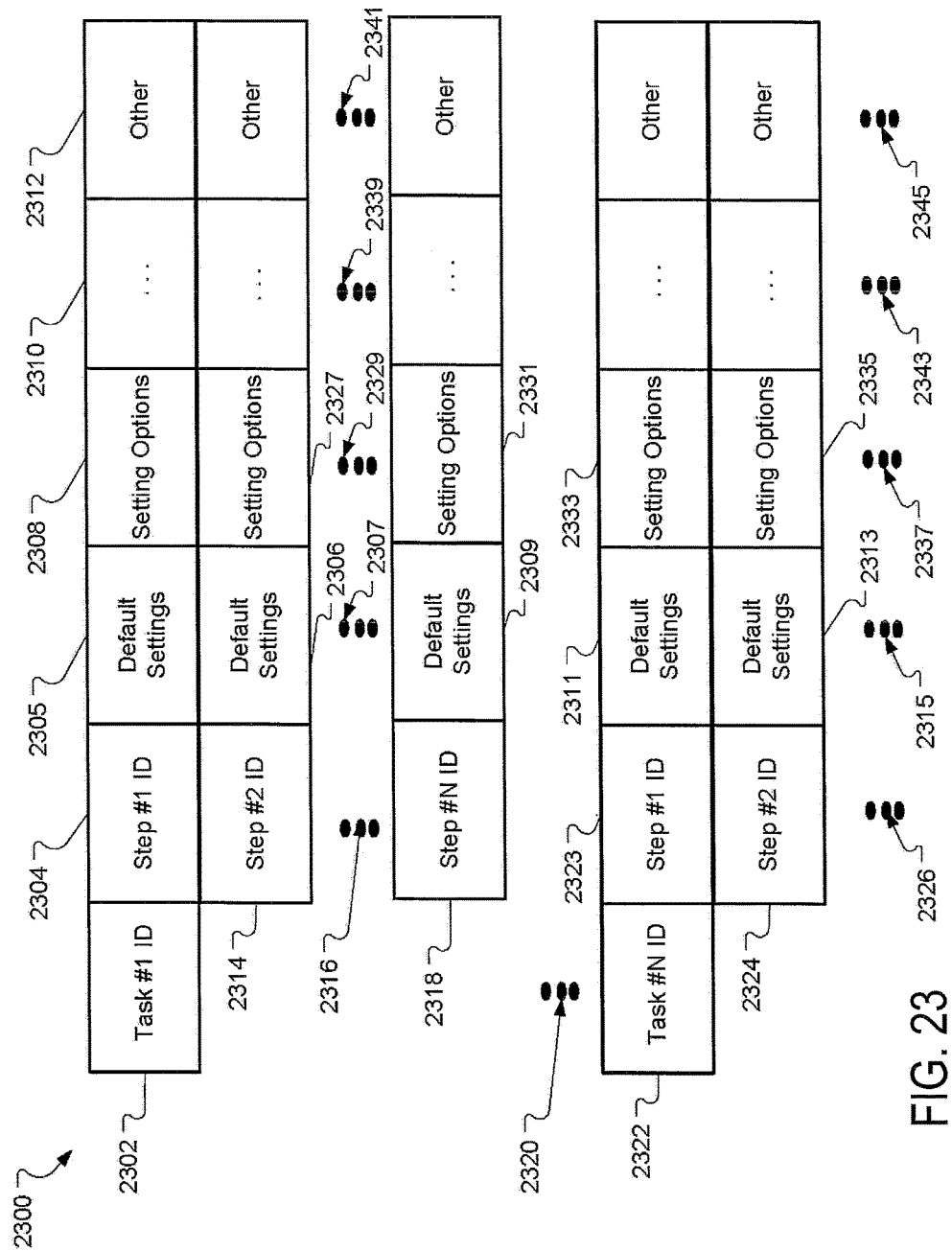
FIG. 23 depicts an example data structure associated with a setting of a protocol step for use with the cell expansion system in accordance with embodiments of the present disclosure.

Turning to FIG. 23, an example data structure 2300 having attributes, fields, and/or portions storing data is provided in accordance with embodiments disclosed herein. The data structure may be part of any storage system. The data structure includes a task or protocol, and, in embodiments, the task or protocol data further comprises identifying data 2302. One or more tasks or protocols may be included, as shown by ellipsis 2320 and additional task identifying data 2322. Embodiments further provide for each protocol or task to have a step or process associated with the protocol or task, in which embodiments provide for the step or process to further comprise identifying data 2304. Further, each protocol or task 2302 and/or 2322, for example, may have one or more additional steps or processes associated therewith, as shown by step identifying data 2314, ellipsis 2316, and additional step 2318 for protocol or task 2302, and step identifying data 2323, 2324, and ellipsis 2326 for protocol or task 2322.

In embodiments, each process or step may comprise data including default settings 2305, 2306, 2307, 2309, 2311, 2313, and 2315. In an embodiment, the default settings 2306 comprise data associated with particular settings, including, for example, the IC Inlet, IC Inlet Rate, etc. In an embodiment, default settings 2306 comprise the factory default settings stored by the system. In another embodiment, the default settings comprise previously configured and saved settings, in which such previously configured settings replaced the factory default settings as the new default settings. In yet another embodiment, even where the default settings are configured, the factory default settings are also saved with data 2306, or, in another embodiment, as other data in data structure 2300, as an embodiment provides for resetting configured settings to the factory default settings. Where such resetting of the settings is desired, data for the factory default settings are retrieved.

In embodiments, data structure 2300 further comprises data for setting options 2308, 2327, 2329, 2331, 2333, 2335, and 2337, in which the setting options comprise ranges, for example, of possible data that may be provided for one or more settings. For example, embodiments involving a custom or user-defined task include setting options for the IC Inlet Rate of: 0 to 500 mL/min. Other data, including additional or fewer data, associated with data structure 2300 may be included as shown by ellipses 2310, 2339, and 2343 and Other data 2312, 2341, and 2345, according to embodiments. For example, other data associated with a protocol or task may include, according to an embodiment, data indicating the type of GUI element used to represent a setting in a diagram view or window of the cell expansion system, for example.

The data types depicted in the example data structure 2300 of FIG. 23 are offered for purposes of illustration. The order of the data types may be rearranged, according to embodiments. Further, fewer or additional data attributes, fields, and/or portions may be used in embodiments without departing from the spirit and scope of the present disclosure. Further, numerous types of names referring to the data attributes, fields, and/or portions may be used without departing from the spirit and scope of the present disclosure.

Figure 24:
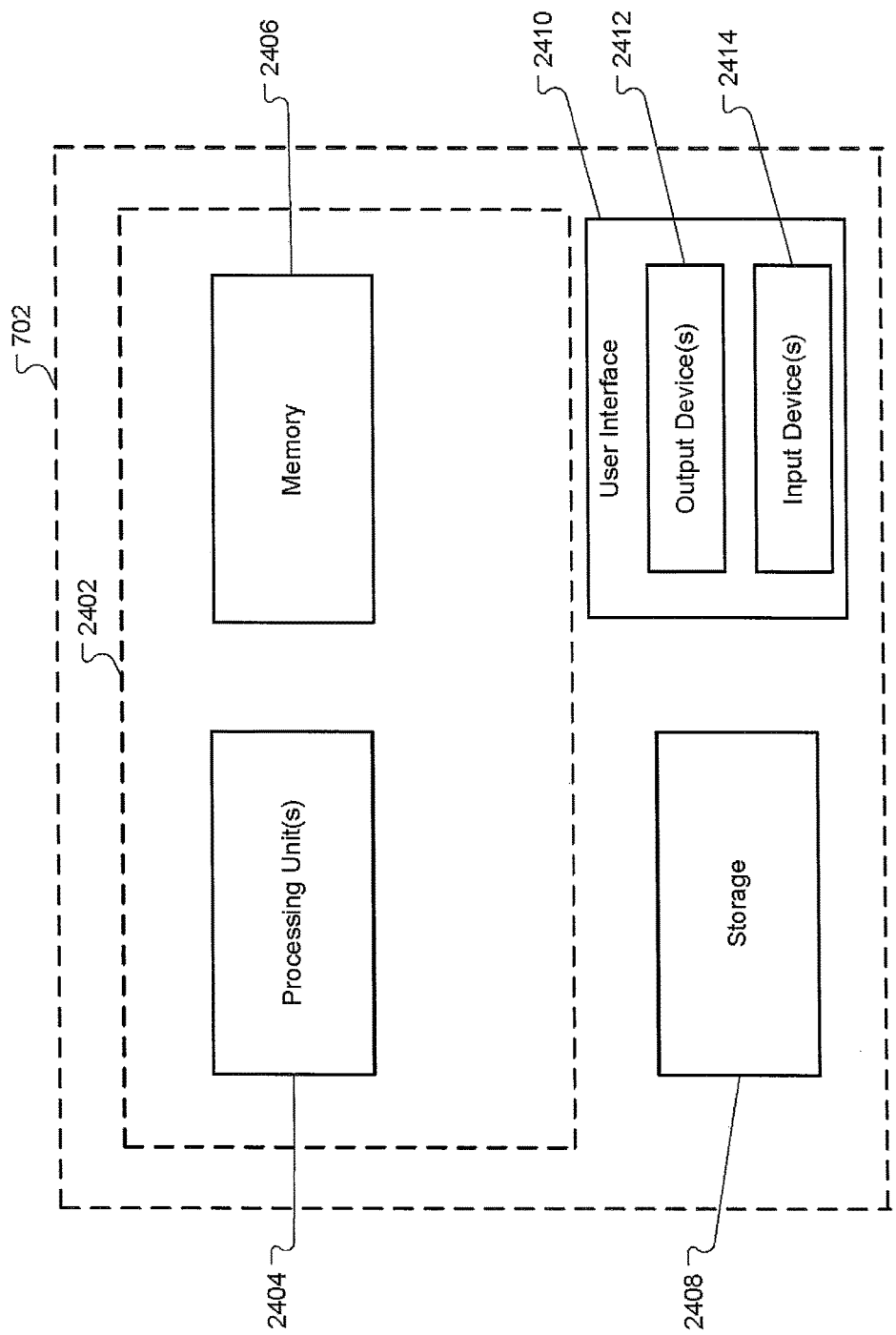
FIG. 24 illustrates an example processing system of the cell expansion system upon which embodiments of the present disclosure may be implemented.

Finally, FIG. 24 illustrates example components of a cell expansion system 702 upon which embodiments of the present disclosure may be implemented. The cell expansion system 702 may include a user interface 2410, a processing system 2402, and/or storage 2408. The user interface 2410 may include output device(s) 2412, and/or input device(s) 2414 as understood by a person of skill in the art. Output device(s) 2412 may include one or more touch screens, in which the touch screen may comprise a display area for providing one or more application windows. The touch screen may also be an input device 2414 that can receive and/or capture physical touch events from a user or operator, for example. The touch screen may comprise a liquid crystal display (LCD) having a capacitance structure that allows the processing system 2402 to deduce the location(s) of touch event(s), as understood by those of skill in the art. The processing system 2402 may then map the location of touch events to UI elements rendered in predetermined locations of an application window. The touch screen may also receive touch events through one or more other electronic structures, according to embodiments. Other output devices 2412 may include a printer, speaker, etc. Other input devices 2414 may include a keyboard, other touch input devices, mouse, voice input device, etc., as understood by a person of skill in the art.

Processing system 2402 may include a processing unit 2404 and/or a memory 2406, according to embodiments of the present disclosure. The processing unit 2404 may be a general purpose processor operable to execute instructions stored in memory 2406. Processing unit 2404 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 2406 may include any short-term or long-term storage for data and/or processor executable instructions, according to embodiments. The memory 2406 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 2408 may be any long-term data storage device or component. Storage 2408 may include one or more of the systems described in conjunction with the memory 2406, according to embodiments. The storage 2408 may be permanent or removable. In embodiments, storage 2408 stores data generated or provided by the processing system 2402.

It will be apparent to those skilled in the art that various modifications can be made to the apparatus, systems, and methods described herein. Thus, it should be understood that the embodiments are not limited to the subject matter discussed in the Specification. Rather, the present disclosure is intended to cover modifications, variations, and/or equivalents. The acts, features, structures, and/or media are disclosed as illustrative embodiments for implementation of the claims. The invention is defined by the appended claims.

What is claimed is:

1. A method for customizing a task for use with a cell expansion system, the method comprising:
   providing a bioreactor in the cell expansion system;
   providing a user interface, wherein the user interface is operable to display data and receive user input;
   providing a memory;
   providing a processor in communication with the user interface and the memory;

the processor receiving, through the user interface, a first selection to create a first custom task for expanding a plurality of cells in the bioreactor;

in response to the receiving the first selection, the processor:
  providing, through the user interface, one or more types of steps to add for the first custom task;
  receiving, through the user interface, a second selection of a first step for the first custom task;
  in response to the receiving the second selection, retrieving, from the memory, one or more settings for the first step;
  displaying, through the user interface, the one or more settings for the first step;
  receiving, through the user interface, a third selection to modify the one or more settings for the first step;
  in response to the third selection, providing, through the user interface, a diagram view of the cell expansion system for customizing the first step, comprising:
    associating the diagram view with the first step in the user interface;
    providing a first setting of the one or more settings as a first graphical user interface element for selection in the user interface;
    receiving, through the user interface, a fourth selection of the first graphical user interface element;
    receiving, through the user interface, a value for the first graphical user interface element;
  receiving an indication to execute the first custom task; and
  executing the first custom task using the received value for the first setting to expand the plurality of the cells.

2. The method as defined in claim 1, wherein the user interface is a touch screen, and wherein the receiving, through the user interface, a first selection to create the first custom task comprises:
  receiving a touch event on the touch screen, wherein the touch screen comprises a display area;
  determining a location of the touch event;
  mapping the location of the touch event to the first graphical user interface element; and
  determining the first graphical user interface element is associated with the first setting.

3. The method as defined in claim 2, wherein the touch screen comprises an input device that can receive one or more touch events.

4. The method as defined in claim 1, further comprising:
  determining whether the first setting is associated with a numeric value; and
  if the first setting is associated with the numeric value, providing a data entry pad in the diagram view to receive the numeric value.

5. The method as defined in claim 4, further comprising:
  if the first setting is not associated with the numeric value, determining if the first setting is associated with a menu of selection options; and
  if the first setting is associated with the menu of selection options, providing the menu of selection options in the diagram view.

6. The method as defined in claim 4, further comprising:
  receiving, through the data entry pad, the numeric value for modifying the first setting; and
  storing the received numeric value for modifying the first setting.

7. The method as defined in claim 1, wherein the first setting comprises one or more from the group consisting of: intracapillary inlet, intracapillary inlet rate, intracapillary circulation rate, extracapillary inlet, extracapillary inlet rate, extracapillary circulation rate, rocker, and stop condition.

8. The method as defined in claim 1, wherein the providing the first setting of the one or more settings as the first graphical user interface element for selection comprises:
  enabling the first graphical user interface element for selection.

9. The method as defined in claim 1, wherein the one or more types of steps to add for the first custom task comprises one or more from the group consisting of: wash out lines, wash out lines through membrane, wash rapidly, harvest cells, add bolus, and custom.

10. The method as defined in claim 1, further comprising:
  receiving a fifth selection to add a second step to the first custom task.

11. The method as defined in claim 10, the processor further:
  providing, through the user interface, a second diagram view of the cell expansion system for customizing the second step, comprising:
    associating the second diagram view with the second step in the user interface.

12. The method as defined in claim 8, wherein the enabling the first graphical user interface element for selection comprises:
  associating a first visual indicator with the first graphical user interface element; and
  in response to determining the first setting can be modified, associating a second visual indicator with the first graphical user interface element.

13. The method as defined in claim 1, wherein the bioreactor comprises a hollow fiber membrane.

14. The method as defined in claim 13, wherein the providing, through the user interface, the diagram view of the cell expansion system for customizing the first step further comprises:
  depicting an intracapillary space of the bioreactor in the diagram view; and
  depicting an extracapillary space of the bioreactor in the diagram view.

* * * * *